United States Patent
Salk et al.

(10) Patent No.: US 11,739,367 B2
(45) Date of Patent: Aug. 29, 2023

(54) REAGENTS AND ADAPTERS FOR NUCLEIC ACID SEQUENCING AND METHODS FOR MAKING SUCH REAGENTS AND ADAPTERS

(71) Applicant: TwinStrand Biosciences, Inc., Seattle, WA (US)

(72) Inventors: Jesse J. Salk, Seattle, WA (US); Scott R. Kennedy, Seattle, WA (US)

(73) Assignee: TwinStrand Biosciences, Inc., Seattle, WA (US)

( * ) Notice: Subject to any disclaimer, the term of this patent is extended or adjusted under 35 U.S.C. 154(b) by 478 days.

(21) Appl. No.: 16/758,726

(22) PCT Filed: Nov. 8, 2018

(86) PCT No.: PCT/US2018/059908
§ 371 (c)(1),
(2) Date: Apr. 23, 2020

(87) PCT Pub. No.: WO2019/094651
PCT Pub. Date: May 16, 2019

(65) Prior Publication Data
US 2020/0362390 A1 Nov. 19, 2020

Related U.S. Application Data

(60) Provisional application No. 62/583,462, filed on Nov. 8, 2017.

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01)

(58) Field of Classification Search
CPC .. C12Q 1/6806; C12Q 1/6869; C12Q 1/6855; C12Q 2525/191
See application file for complete search history.

(56) References Cited

U.S. PATENT DOCUMENTS

| | | | |
|---|---|---|---|
| 5,308,751 A | 5/1994 | Ohkawa et al. |
| 5,589,337 A | 12/1996 | Farr |
| 6,251,610 B1 | 6/2001 | Gupte et al. |
| 6,258,539 B1 | 7/2001 | Hunkapiller et al. |
| 6,498,023 B1 | 12/2002 | Abarzua |
| 6,582,908 B2 | 6/2003 | Fodor et al. |
| 6,958,225 B2 | 10/2005 | Dong |
| 7,214,490 B2 | 5/2007 | Su et al. |
| 7,267,966 B2 | 9/2007 | Dong et al. |
| 7,297,778 B2 | 11/2007 | Matsuzaki et al. |
| 7,406,385 B2 | 7/2008 | Sorenson |
| 7,452,699 B2 | 11/2008 | Makrigiorgos |
| 7,459,273 B2 | 12/2008 | Jones et al. |
| 7,476,503 B2 | 1/2009 | Turner et al. |
| 7,741,463 B2 | 6/2010 | Gormley et al. |
| 8,029,993 B2 | 10/2011 | Mikawa |
| 8,148,068 B2 | 4/2012 | Brenner |
| 8,153,375 B2 | 4/2012 | Travers et al. |
| 8,318,434 B2 | 11/2012 | Cuppens |
| 8,715,967 B2 | 5/2014 | Casbon et al. |
| 8,741,606 B2 | 6/2014 | Casbon et al. |
| 9,080,210 B2 | 7/2015 | Van Eijk et al. |
| 9,085,798 B2 | 7/2015 | Chee |
| 9,249,460 B2 | 2/2016 | Pushkarev et al. |
| 9,260,753 B2 | 2/2016 | Xie et al. |
| 9,476,095 B2 | 10/2016 | Vogelstein et al. |
| 9,598,731 B2 | 3/2017 | Talasaz |
| 9,745,627 B2 | 8/2017 | Van Eijk et al. |
| 9,752,188 B2 | 9/2017 | Schmitt |
| 9,783,847 B2 | 10/2017 | Chee |
| 9,834,822 B2 | 12/2017 | Talasaz |
| 9,862,995 B2 | 1/2018 | Patel |
| 9,898,577 B2 | 2/2018 | Van Eijk et al. |
| 9,920,366 B2 | 3/2018 | Eltoukhy et al. |
| 10,000,800 B2 | 6/2018 | Chee |
| 10,011,871 B2 | 7/2018 | Bielas |
| 10,023,907 B2 | 7/2018 | Van Eijk et al. |
| 10,119,165 B2 | 11/2018 | Chee |
| 10,202,646 B2 | 2/2019 | Fodor et al. |
| 10,266,883 B2 | 4/2019 | Chee |
| 10,266,884 B2 | 4/2019 | Chee |
| 10,287,630 B2 | 5/2019 | Xie et al. |
| 10,287,631 B2 | 5/2019 | Salk et al. |
| 10,370,713 B2 | 8/2019 | Salk et al. |

(Continued)

FOREIGN PATENT DOCUMENTS

| | | |
|---|---|---|
| CN | 102877136 B | 3/2014 |
| CN | 106367485 A | 2/2017 |

(Continued)

OTHER PUBLICATIONS

Ahn, E.H., et al., "Decreased Mitochondrial Mutagenesis during Transformation of Human Breast Stem Cells into Tumorigenic Cells," Cancer Research 76(15):4569-4578, American Association of Cancer Research, United States (Aug. 2016).

Akogwu, I., et al., "A Comparative Study of K-Spectrum-Based Error Correction Methods for Next-Generation Sequencing Data Analysis Human Genomics," Human Genomics 2(20):50-59, BioMed Central, England (Jul. 2016).

Ameur, A., et al., "Ultra-Deep Sequencing of Mouse Mitochondrial DNA: Mutational Patterns and Their Origins," PLoS Genetics 7(3):e1002028, Public Library of Science, United States (Mar. 2011).

Bainbridge, N.M., et al., "Whole Exome Capture in Solution With 3 Gbp of Data," Genome Biology 11(6): R62, BioMed Central Ltd, England (2010).

(Continued)

*Primary Examiner* — David C Thomas
(74) *Attorney, Agent, or Firm* — Sterne, Kessler, Goldstein & Fox P.L.L.C.

(57) ABSTRACT

Methods for making and using reagents and adapters for use in nucleic acid sequencing applications are disclosed herein. In several embodiments, adapters and reagents and the methods of making such adapters and reagents can be used for Duplex Sequencing applications.

15 Claims, 21 Drawing Sheets

(56) References Cited

U.S. PATENT DOCUMENTS

| | | |
|---|---|---|
| 10,385,393 B2 | 8/2019 | Salk et al. |
| 10,501,793 B2 | 12/2019 | Chee |
| 10,570,451 B2 | 2/2020 | Salk et al. |
| 10,689,700 B2 | 6/2020 | Salk et al. |
| 10,711,304 B2 | 7/2020 | Salk et al. |
| 10,752,951 B2 | 8/2020 | Salk et al. |
| 10,760,127 B2 | 9/2020 | Salk et al. |
| 10,844,428 B2 | 11/2020 | Gnerre et al. |
| 10,870,882 B2 | 12/2020 | Otwinowski et al. |
| 11,118,225 B2 | 9/2021 | Salk et al. |
| 11,198,907 B2 | 12/2021 | Salk et al. |
| 11,242,562 B2 | 2/2022 | Salk et al. |
| 2003/0165923 A1 | 9/2003 | Li et al. |
| 2004/0209299 A1 | 10/2004 | Pinter et al. |
| 2005/0100900 A1 | 5/2005 | Kawashima et al. |
| 2007/0020640 A1 | 1/2007 | McCloskey et al. |
| 2007/0128624 A1 | 6/2007 | Gormley et al. |
| 2007/0172839 A1 | 7/2007 | Smith et al. |
| 2007/0172873 A1 | 7/2007 | Brenner et al. |
| 2008/0167195 A1 | 7/2008 | Li et al. |
| 2008/0261204 A1 | 10/2008 | Lexow |
| 2009/0298075 A1 | 12/2009 | Travers et al. |
| 2010/0069263 A1 | 3/2010 | Shendure et al. |
| 2010/0222238 A1 | 9/2010 | Smith et al. |
| 2010/0331204 A1 | 12/2010 | Jeddeloh et al. |
| 2011/0160078 A1 | 6/2011 | Fodor et al. |
| 2011/0301042 A1 | 12/2011 | Steinmann et al. |
| 2012/0058468 A1 | 3/2012 | McKeown |
| 2012/0071331 A1 | 3/2012 | Casbon et al. |
| 2012/0094847 A1 | 4/2012 | Warthmann et al. |
| 2012/0165202 A1 | 6/2012 | Porreca et al. |
| 2012/0208724 A1 | 8/2012 | Steemers et al. |
| 2012/0220494 A1 | 8/2012 | Samuels et al. |
| 2012/0238738 A1 | 9/2012 | Hendrickson |
| 2012/0244525 A1 | 9/2012 | Hendrickson |
| 2012/0322666 A1 | 12/2012 | Pham et al. |
| 2013/0079231 A1 | 3/2013 | Pushkarev et al. |
| 2013/0303461 A1 | 11/2013 | Iafrate et al. |
| 2014/0030704 A1 | 1/2014 | Mikawa |
| 2014/0057799 A1 | 2/2014 | Johnson et al. |
| 2014/0134610 A1 | 5/2014 | Pham et al. |
| 2014/0155274 A1 | 6/2014 | Xie et al. |
| 2014/0329282 A1 | 11/2014 | Nelson et al. |
| 2014/0329698 A1 | 11/2014 | Bignell et al. |
| 2015/0024950 A1 | 1/2015 | Bielas et al. |
| 2015/0044687 A1 | 2/2015 | Schmitt et al. |
| 2015/0119261 A1 | 4/2015 | Richard |
| 2015/0197786 A1 | 7/2015 | Osborne et al. |
| 2015/0275289 A1 | 10/2015 | Otwinowski et al. |
| 2015/0284803 A1 | 10/2015 | Lindley |
| 2016/0026758 A1 | 1/2016 | Jabara et al. |
| 2016/0130649 A1 | 5/2016 | Xie et al. |
| 2016/0153039 A1 | 6/2016 | Amorese et al. |
| 2016/0319345 A1 | 11/2016 | Gnerre et al. |
| 2016/0362751 A1 | 12/2016 | Shin et al. |
| 2017/0107560 A1 | 4/2017 | Peter et al. |
| 2017/0136433 A1 | 5/2017 | Sun et al. |
| 2017/0211140 A1 | 7/2017 | Schmitt et al. |
| 2017/0247687 A1 | 8/2017 | Shendure et al. |
| 2018/0023135 A1 | 1/2018 | Van Eijk et al. |
| 2018/0291438 A1 | 10/2018 | Jamshidi et al. |
| 2018/0363048 A1 | 12/2018 | Bielas |
| 2018/0363049 A1 | 12/2018 | Bielas |
| 2018/0363051 A1 | 12/2018 | Schmitt et al. |
| 2018/0363052 A1 | 12/2018 | Schmitt et al. |
| 2018/0363053 A1 | 12/2018 | Schmitt et al. |
| 2019/0093160 A1 | 3/2019 | Schmitt et al. |
| 2019/0093161 A1 | 3/2019 | Schmitt et al. |
| 2019/0093162 A1 | 3/2019 | Schmitt et al. |
| 2019/0119748 A1 | 4/2019 | Schmitt et al. |
| 2019/0119749 A1 | 4/2019 | Schmitt et al. |
| 2019/0271040 A1 | 9/2019 | Salk et al. |
| 2019/0284626 A1 | 9/2019 | Salk et al. |
| 2019/0284627 A1 | 9/2019 | Salk et al. |
| 2019/0292597 A1 | 9/2019 | Salk et al. |
| 2019/0323082 A1 | 10/2019 | Salk et al. |
| 2019/0338358 A1 | 11/2019 | Salk et al. |
| 2019/0352714 A1 | 11/2019 | Salk et al. |
| 2020/0048701 A1 | 2/2020 | Chee |
| 2020/0048702 A1 | 2/2020 | Chee |
| 2020/0048703 A1 | 2/2020 | Chee |
| 2020/0131561 A1 | 4/2020 | Kennedy et al. |
| 2020/0318185 A1 | 10/2020 | Salk et al. |
| 2020/0362390 A1 | 11/2020 | Salk et al. |
| 2020/0392580 A1 | 12/2020 | Salk et al. |
| 2021/0002711 A1 | 1/2021 | Otwinowski et al. |
| 2021/0010065 A1 | 1/2021 | Salk et al. |
| 2021/0207210 A1 | 7/2021 | Otwinowski et al. |
| 2021/0269873 A1 | 9/2021 | Salk et al. |
| 2021/0277461 A1 | 9/2021 | Glezer et al. |
| 2021/0292836 A1 | 9/2021 | Salk et al. |
| 2021/0324470 A1 | 10/2021 | Salk et al. |
| 2021/0355532 A1 | 11/2021 | Salk et al. |
| 2021/0371920 A1 | 12/2021 | Salk et al. |
| 2021/0371921 A1 | 12/2021 | Salk et al. |
| 2021/0371922 A1 | 12/2021 | Salk et al. |
| 2021/0371923 A1 | 12/2021 | Salk et al. |
| 2021/0371924 A1 | 12/2021 | Salk et al. |
| 2021/0381048 A1 | 12/2021 | Salk et al. |
| 2022/0010376 A1 | 1/2022 | Salk et al. |
| 2022/0017961 A1 | 1/2022 | Salk et al. |
| 2022/0195523 A1 | 6/2022 | Salk et al. |

FOREIGN PATENT DOCUMENTS

| | | |
|---|---|---|
| GB | 2533882 B | 10/2016 |
| WO | WO-2006113422 A2 | 10/2006 |
| WO | WO-2010112821 A1 | 10/2010 |
| WO | WO-2010148115 A1 | 12/2010 |
| WO | WO-2011021102 A2 | 2/2011 |
| WO | WO-2012042374 A2 | 4/2012 |
| WO | WO-2012061832 A1 | 5/2012 |
| WO | WO-2012129363 A2 | 9/2012 |
| WO | WO-2012142213 A2 | 10/2012 |
| WO | WO-2013123442 A1 | 8/2013 |
| WO | WO-2013142389 A1 | 9/2013 |
| WO | WO-2013181170 A1 | 12/2013 |
| WO | WO-2014142850 A1 | 9/2014 |
| WO | WO-2015075056 A1 | 5/2015 |
| WO | WO-2015100427 A1 | 7/2015 |
| WO | WO-2015117040 A1 | 8/2015 |
| WO | WO-2016040901 A1 | 3/2016 |
| WO | WO-2017037656 A1 | 3/2017 |
| WO | WO-2017100441 A1 | 6/2017 |
| WO | WO-2018013598 A1 | 1/2018 |
| WO | WO-2018031588 A1 | 2/2018 |
| WO | WO-2019094651 A1 | 5/2019 |
| WO | WO-2020014693 A1 | 1/2020 |

OTHER PUBLICATIONS

Bentley, R.D., et al., "Accurate Whole Human Genome Sequencing Using Reversible Terminator Chemistry," Nature 456(7218):53-59, Nature Publishing Group, England (Nov. 2008).

Besaratinia, A., et al., "A High-throughput Next-Generation Sequencing-based Method for Detecting the Mutational Fingerprint of Carcinogens," Nucleic Acids Research 40(15):e116, Oxford University Press, England (Aug. 2012).

Bielas, H.J., et al., et al., "Quantification of Random Genomic Mutations," Nature Methods 2(4):285-290, Nature Publishing Group, United States (Apr. 2005).

Borodina, T., et al., "A Strand-Specific Library Preparation Protocol for RNA Sequencing," Methods in Enzymology 500:79-98, Academic Press, United States (2011).

Boyd, S.D, et al., "Measurement and Clinical Monitoring of Human Lymphocyte Clonality by Massively Parallel Vdj Pyrosequencing," Science Translational Medicine 1(12):12ra23, American Association for the Advancement of Science, United States (Dec. 2009).

Campbell, J.P., et al., "Subclonal Phylogenetic Structures in Cancer Revealed by Ultra-Deep Sequencing," Proceedings of the National Academy of Sciences of the United States of America 105(35):13081-13086, National Academy of Sciences, United States (Aug. 2008).

(56) References Cited

OTHER PUBLICATIONS

Carlson, C.A., "Decoding Cell Lineage From Acquired Mutations Using Arbitrary Deep Sequencing," Nature Methods 9:78-80, Nature Publication Group, United States (2012).
Casbon, A.J., et al., "A Method for Counting PCR Template Molecules With Application to Next-Generation Sequencing," Nucleic Acids Research 39(12):e81, Oxford University Press, England (Jul. 2011).
Cervantes, B.R., et al., "Embryonic Stem Cells and Somatic Cells Differ in Mutation Frequency and Type," Proceedings of the National Academy of Sciences of the United States of America 99(6):3586-3590, National Academy of Sciences United States (Mar. 2002).
Chen, L., et al., "DNA Damage Is a Pervasive Cause of Sequencing Errors, Directly Confounding Variant Identification," Science 355(6326):752-756, American Association for the Advancement of Science, United States (Feb. 2017).
Chiu, R.W.K., et al., "Non-Invasive Prenatal Assessment of Trisomy 21 by Multiplexed Maternal Plasma DNA Sequencing: Large Scale Validity Study," BMJ (Clinical research ed.) 342:c7401, British Medical Association, England (Jan. 2011).
Chiu, R.W.K., et al., "Non-Invasive Prenatal Diagnosis of Fetal Chromosomal Aneuploidy by Massively Parallel Genomic Sequencing of DNA in Maternal Plasma," Proceedings of the National Academy of Sciences of the United States of America 105(51):20458-20463, National Academy of Sciences, United States (Dec. 2008).
Clark, T.A, et al., "Direct Detection and Sequencing of Damaged DNA Bases," Genome Integrity 2:10, Medknow, England (Dec. 2011).
Craig, D.W., et al., "Identification of Genetic Variants Using Barcoded Multiplexed Sequencing," Nature 5(10):887-893, Nature Publishing Group, England (Oct. 2008).
De Grassi, A., et al., "Ultradeep Sequencing of a Human Ultraconserved Region Reveals Somatic and Constitutional Genomic Instability," PLoS Biology 8(1):e1000275, Public Library of Science, United States (Jan. 2010).
Diehl, F., et al., "Analysis of Mutations in DNA Isolated From Plasma and Stool of Colorectal Cancer Patients," Gastroenterology 135(2):489-498, W.B. Saunders, United States (Aug. 2008).
Diehl, F., et al., "Detection and Quantification of Mutations in the Plasma of Patients With Colorectal Tumors," Proceedings of the National Academy of Sciences of the United States of America 102(45):16368-16373, National Academy of Sciences, United States (Nov. 2005).
Ding, L., et al., "Analysis of Next-Generation Genomic Data in Cancer: Accomplishments and Challenges," Human Molecular Genetics 19(R2):R188-R196, IRL Press at Oxford University Press, England (Oct. 2010).
Ding, L., et al., "Clonal Evolution in Relapsed Acute Myeloid Leukaemia Revealed by Whole-Genome Sequencing," Nature 481;(7382):506-510, Nature Publishing Group, England (Jan. 2012).
Druley, E.T., et al., "Quantification of Rare Allelic Variants From Pooled Genomic DNA," Nature Methods 6(4):263-265, Nature Publication Group, United States (Apr. 2009).
Ehrich, M., et al., "Noninvasive Detection of Fetal Trisomy 21 by Sequencing of DNA in Maternal Blood: A Study in a Clinical Setting," American Journal of Obstetrics and Gynecology 204(3):205. e1-11, Elsevier, United States (Mar. 2011).
Evans et al., "NEB Expressions" New England BioLabs (2007) (IPR2022-00816 Ex. 1014).
Ewing, B. and Green, P., "Base-calling of Automated Sequencer Traces Using Phred. II. Error Probabilities," Genome Research 8(3):186-194, Cold Spring Harbor Laboratory Press, United States (Mar. 1998).
Fan, C.H., et al., "Noninvasive Diagnosis of Fetal Aneuploidy by Shotgun Sequencing DNA From Maternal Blood," Proceedings of the National Academy of Sciences of the United States of America 105(42):16266-16271, National Academy of Sciences, United States (Oct. 2008).

Flaherty, P., et al., "Ultrasensitive Detection of Rare Mutations Using Next-Generation Targeted Resequencing," Nucleic Acids Research 40(1):e2, Oxford University Press, England (Jan. 2012).
Fleischhacker, M and Schmidt, B., Circulating Nucleic Acids (CNAs) and Cancer—a Survey, Biochimica Et Biophysica Acta 1775(1):181-232, Elsevier Pub. Co, Netherlands (Jan. 2007).
Fong, L.S., et al., "Comparison of 7 Methods for Extracting Cell-Free DNA From Serum Samples of Colorectal Cancer Patients," Clinical Chemistry 55(3):587-589, Oxford University Press, England (Mar. 2009).
Fordyce, L.S., et al., "High-throughput Sequencing of Core Str Loci for Forensic Genetic Investigations Using the Roche Genome Sequencer Fix Platform," BioTechniques 51(2):127-133, Future Science, England (Aug. 2011).
Forshew, T., et al., "Noninvasive Identification and Monitoring of Cancer Mutations by Targeted Deep Sequencing of Plasma DNA," Science Translational Medicine 4(136):136ra68, American Association for the Advancement of Science, United States (May 2012).
Fu, K.G., et al., "Counting Individual DNA Molecules by the Stochastic Attachment of Diverse Labels," Proceedings of the National Academy of Sciences 108(22):9026-9031, National Academy of Sciences, United States (May 2011).
Garcia-Garcerà, M., et al., "Fragmentation of Contaminant and Endogenous DNA in Ancient Samples Determined by Shotgun Sequencing; Prospects for Human Palaeogenomics," Plos One 6(8):e24161, Public Library of Science, United States (2011).
Goodwin, S., et al., "Coming of Age: Ten Years of Next-Generation Sequencing Technologies," Nature Reviews. Genetics 17(6):333-351, Nature Publishing Group, England (May 2016).
Gordon, J.D., et al., "Causes and Consequences of Aneuploidy in Cancer," Nature Reviews 13(3):189-203, Nature Pub. Group, England (Jan. 2012).
Greaves, C.L., et al., "Quantification of Mitochondrial DNA Mutation Load," Aging Cell 8(5):566-572, Blackwell Pub, England (Sep. 2009).
Haag-Liautard, H.C., et al., "Direct Estimation of the Mitochondrial DNA Mutation Rate in *Drosophila melanogaster*," PLoS Biology 6(8):e204, Public Library of Science, United States (Aug. 2008).
Hartung, T., "Thresholds of Toxicological Concern—Setting a Threshold for Testing Below Which There is Little Concern," ALTEX 34(3):331-351, Spektrum Akademischer Verlag, Germany (Jan. 2017).
Havens, J., "The technology and clinical applications of hybrid capture," NGSMedical Laboratory Observer retrieved from: https://www.mlo-online.com/home/article/13008809/the-technology-and-clinical-applications-of-hybrid-capture-ngs, published Jul. 2016, 5 pages.
He, Y., et al., "Heteroplasmic Mitochondrial DNA Mutations in Normal and Tumour Cells," Nature 464(7288):610-614, Nature Publishing Group, England (Mar. 2010).
Hiatt, J.B., et al., "Single Molecule Molecular Inversion Probes for Targeted, High-Accuracy Detection of Low-Frequency Variation," Genome Research 23(5):843-854, Cold Spring Harbor Laboratory Press, United States (May 2013).
Hodges, E., et al., "Genome-wide in Situ Exon Capture for Selective Resequencing," Nature Genetics 39(12):1522-1527, Nature Pub, United States (Dec. 2007).
Hodgkinson, A., et al., "Variation in the Mutation Rate Across Mammalian Genomes," Nature Reviews 12(11):756-766, Nature Publication Group, England (Oct. 2011).
Howell, N., et al., "How Rapidly Does the Human Mitochondrial Genome Evolve?," American Journal of Human Genetics 59(3):501-509, American Society of Human Genetics, United States (Sep. 1996).
Hyman, W.R., et al., "The Dynamics of the Vaginal Microbiome During Infertility Therapy With in Vitro Fertilization-Embryo Transfer," Journal of Assisted Reproduction and Genetics 29(2):105-115, Springer, Netherlands (Feb. 2012).
Illumina, Complete Secondary Analysis Workflow for the Genome Analyzer, Technical Note: Illumina Systems and Software (2009) (IPR2022-00816 Ex. 1011).
Illumina, Preparing Samples for Sequencing Genomic DNA (2007) (IPR2022-00816 Ex. 1008).

(56) References Cited

OTHER PUBLICATIONS

Illumina, TruSeq RNA and DNA Sample Preparation Kits, Data Sheet: Illumina Sequencing (2010) ((IPR2022-00816 Ex. 1012).
International Search Report and Written Opinion for Application No. PCT/US2013/032665, dated Jul. 9, 2013, 15 pages.
International Search Report and Written Opinion for PCT/US2018/024194 dated Jul. 7, 2018. 10 pages.
Jabara, B.C., et al., "Accurate Sampling and Deep Sequencing of the HIV-1 Protease Gene Using a Primer Id," Proceedings of the National Academy of Sciences of the United States of America 108(50):20166-20171, National Academy of Sciences, United States (Dec. 2011).
Jazin, E.E., et al., "Human Brain Contains High Levels of Heteroplasmy in the Noncoding Regions of Mitochondrial DNA," Proceedings of the National Academy of Sciences of the United States of America 93(22):12382-123827, National Academy of Sciences, United States (Oct. 1996).
Jiang, H., et al., "Seqmap: Mapping Massive Amount of Oligonucleotides to the Genome," Bioinformatics 24(20):2395-2396, Oxford University Press, England (Oct. 2008).
Jung, H., et al., "The DNA Integrity Number (DIN) Provided by the Genomic DNA Screen Tape Assay Allows for Streamlining of NGS of FFPE Tissue Samples Application Note Nucleic Acid Analysis," Agilent Technologies, 4 pages, Korea (Dec. 2015).
Kanagawa, T., "Bias and Artifacts in Multitemplate Polymerase Chain Reactions (Pcr)," Journal of Bioscience and Bioengineering 96(4):317-323, Society for Biotechnology, Japan (2003).
Kao, C.W., et al., "Bayescall: A Model-based Base-Calling Algorithm for High-throughput Short-Read Sequencing," Genome Research 19(10):1884-1895, Cold Spring Harbor Laboratory Press, United States (Oct. 2009).
Kasai, H., et al., "Formation, Inhibition of Formation, and Repair of Oxidative 8-hydroxy guanine DNA Damage," Basic Life Sciences 61:257-262, Plenum Press, United States (1993).
Kaur, M. and Makrigiorgos, G.M, "Novel Amplification of DNA in a Hairpin Structure: Towards a Radical Elimination of PCR Errors From Amplified DNA," Nucleic Acids Research 31(6):e26, Oxford University Press, England (Mar. 2003).
Kebschull, J.M and Zador, A.M., "Sources of PCR-Induced Distortions in High-throughput Sequencing Data Sets," Nucleic Acids Research 43(21):e143, Oxford University Press, England (Dec. 2015).
Kennedy, S. R., et al., "Ultra-sensitive sequencing reveals an age-related increase in somatic mitochondrial mutations that are inconsistent with oxidative damage," PLoS Genet 9(9):e1003794, Public Library of Science, United States (2013).
Kennedy, S. R., et al., "Detecting ultralow-frequency mutations by Duplex Sequencing," Nat Protoc 9(11):2586-2606, Nature Publishing Group, United Kingdom (2014).
Kennedy, R.S., et al., "Somatic Mutations in Aging, Cancer and Neurodegeneration," Mechanisms of Ageing and Development 133(4):118-126, Elsevier Science Ireland, Ireland (Apr. 2012).
Khaidakov, M., et al., "Accumulation of Point Mutations in Mitochondrial DNA of Aging Mice," Mutation Research 526(1-2):1-7, Elsevier, Netherlands (May 2003).
Kinde, I., et al., "Detection and Quantification of Rare Mutations With Massively Parallel Sequencing," Proceedings of the National Academy of Sciences of the United States of America 108(23):9530-9535, National Academy of Sciences, United States (Jun. 2011).
Kircher, M., et al., "Improved Base Calling for the Illumina Genome Analyzer Using Machine Learning Strategies," Genome Biology 10(8):R83, BioMed Central Ltd, England (2009).
Kirsch, S., and Klein, A.C., "Sequence Error Storms and the Landscape of Mutations in Cancer," Proceedings of the National Academy of Sciences of the United States of America 109(36):14289-14290, National Academy of Sciences, United States (Sep. 2012).
Kivioja, T., et al., "Counting Absolute Numbers of Molecules Using Unique Molecular Identifiers," Nature Methods 9(1):72-74, Nature Publication Group, United States (Nov. 2011).
Kozarewa, I., et al., Amplification-Free Illumina Sequencing-Library Preparation Facilitates Improved Mapping and Assembly of (G+c)-biased Genomes, Nature Methods 6(4):291-295, Nature Pub. Group, United States (Apr. 2009).
Kraytsberg, Y., et al., "Single Molecule PCR inMtDNA Mutational Analysis: Genuine Mutations Vs. Damage Bypass-derived Artifacts," Methods 46(4):269-273, Academic Press, United States (Dec. 2008).
Krimmel, J.D., et al., "Ultra-Deep Sequencing Detects Ovarian Cancer Cells in Peritoneal Fluid and Reveals Somatic TP53 Mutations in Noncancerous Tissues," Proceedings of the National Academy of Sciences of the United States of America 113(21):6005-6010, United States National Academy of the Sciences, United States (May 2016).
Kunkel, A.T., "Mutational Specificity of Depurination," Proceedings of the National Academy of Sciences of the United States of America 81(5):1494-1498, National Academy of Sciences, United States (Mar. 1984).
Latuga, S.M., et al., "Beyond Bacteria: A Study of the Enteric Microbial Consortium in Extremely Low Birth Weight Infants," PLoS One 6(12):e27858, Public Library of Science, United States (2011).
Lecroq, B., et al., "Ultra-Deep Sequencing of Foraminiferal Microbarcodes Unveils Hidden Richness of Early Monothalamous Lineages in Deep-Sea Sediments," Proceedings of the National Academy of Sciences of the United States of America 108(32):13177-13182, National Academy of Sciences,United States (Aug. 2011).
Ledergerber, C., and Dessimoz, C., "Base-Calling for Next-Generation Sequencing Platforms," Briefings in Bioinformatics 12(5):489-497, Stewart Publications, England (Sep. 2011).
Li, H., and Durbin, R., "Fast and Accurate Long-Read Alignment With Burrows-wheeler Transform," Bioinformatics 26(5):589-595, Oxford University Press, England (Mar. 2010).
Li, H., and Durbin, R., "Fast and Accurate Short Read Alignment With Burrows-wheeler Transform," Bioinformatics 25(14):1754-1760, Oxford University Press, England (Jul. 2009).
Li, H., et al., "Mapping Short DNA Sequencing Reads and Calling Variants Using Mapping Quality Scores," Genome Research 18(11):1851-1858, Cold Spring Harbor Laboratory Press, United States (Nov. 2008).
Liang, K.C, et al., "Bayesian Basecalling for DNA Sequence Analysis Using Hidden Markov Models," IEEE/ACM Transactions on Computational Biology and Bioinformatics 4(3):430-440, IEEE Computer Society, United States (Sep. 2007).
Liao, W.J.G., et al "Targeted Massively Parallel Sequencing of Maternal Plasma DNA Permits Efficient and Unbiased Detection of Fetal Alleles," Clinical Chemistry 57(1):92-101, Oxford University Press, England (Jan. 2011).
Lin, T.M., et al., "High Aggregate Burden of Somatic MtDNA Point Mutations in Aging and Alzheimer's Disease Brain," Human Molecular Genetics 11(2):133-145, Press at Oxford University Press, England (Jan. 2002).
Lindahl, T., Wood, D.R., "Quality Control by DNA Repair," Science 286(5446):1897-1905, American Association for the Advancement of Science, United States (Dec. 1999).
Lo, M.Y., et al., Quantitative Analysis of Fetal DNA in Maternal Plasma and Serum: Implications for Noninvasive Prenatal Diagnosis, American Journal of Human Genetics 62(4):768-775, Cell Press, United States (Apr. 1998).
Lou, D.I., et al., "High-Throughput DNA Sequencing Errors Are Reduced by Orders of Magnitude Using Circle Sequencing," Proceedings of the National Academy of Sciences of the United States of America 110(49):19872-19877, National Academy of Sciences, United States (Dec. 2013).
Lunter, G and Goodson, M., "Stampy: A Statistical Algorithm for Sensitive and Fast Mapping of Illumina Sequence Reads," Genome Research 21(6):936-939, Cold Spring Harbor Laboratory Press, United States (Jun. 2011).
Lynch, A.M., et al., "New and Emerging Technologies for Genetic Toxicity Testing," Environmental and Molecular Mutagenesis 52(3):205-223, Wiley-Liss, United States (Apr. 2011).
Lynch, M., "Rate, Molecular Spectrum, and Consequences of Human Mutation," Proceedings of the National Academy of Sci-

(56) References Cited

OTHER PUBLICATIONS ences of the United States of America 107(3):961-968, National Academy of Sciences, United States (Jan. 2010).

MacKelprang, R., et al., "Metagenomic Analysis of a Permafrost Microbial Community Reveals a Rapid Response to Thaw," Nature 480(7377):368-71, Nature Publishing Group, England (Nov. 2011).

Makarova, K.S., "Annotation and Classification of CRISPR-Cas Systems," Methods in Molecular Biology 1311:47-75, Humana Press, United States (2015).

Mattox, A.K., et al., "Bisulfite-converted Duplexes for the Strand-specific Detection and Quantification of Rare Mutations," Proceedings of the National Academy of Sciences of the United States of America 114(18):4733-4738, National Academy of Sciences, United States (May 2017).

McBride, J.T., et al., Mutagenic Spectrum Resulting From DNA Damage by Oxygen Radicals, Biochemistry 30(1):207-213, American Chemical Society, United States (Jan. 1991).

McCarthy, A., "Third Generation DNA Sequencing: Pacific Biosciences' Single Molecule Real Time Technology," Chemistry & Biology 17(7):675-676, Elsevier, United States (Jul. 2010).

McCloskey, L.M., et al., "Encoding Pcr Products With Batch-stamps and Barcodes," Biochemical Genetics 45(11-12):761-767, Kluwer Academic/PlenumPublishers, United States (Dec. 2007).

McKernan, J.K., et al., "Sequence and Structural Variation in a Human Genome Uncovered by Short-read, Massively Parallel Ligation Sequencing Using Two-base Encoding," Genome Research 19(9):1527-1541, Cold Spring Harbor Laboratory Press, United States (Sep. 2009).

Mertes, F., et al., "Targeted Enrichment of Genomic DNA Regions for Next-generation Sequencing," Briefings in Functional Genomics 10(6):374-386, Oxford University Press, England (Nov. 2011).

Metzker, M.L., "Sequencing Technologies—The Next Generation," Nature Reviews: Genetics 11(1):31-46, Nature Pub. Group, England (Jan. 2010).

Meyer, M., et al., "Targeted High-throughput Sequencing of Tagged Nucleic Acid Samples," Nucleic Acids Research 35(15):e97, Oxford University Press, England (2007).

Meyerhans, A., et al., "DNA Recombination During Pcr," Nucleic Acids Research 18(7):1687-1691,Oxford University Press, England (Apr. 1990).

Meyerson, M., et al., "Advances in Understanding Cancer Genomes Through Second-generation Sequencing," Nature Reviews 11(10):685-696, Nature Pub. Group, England (Oct. 2010).

Miner, B.E., et al., Molecular Barcodes Detect Redundancy and Contamination in Hairpin-Bisulfite PCR Nucleic Acids Research 32(17):e135, Oxford University Press, England (Sep. 2004).

Minoche, A.E., et al., "Evaluation of Genomic High-throughput Sequencing Data Generated on Illumina HiSeq and Genome Analyzer Systems," Genome Biology 12(11):R112, BioMed Central Ltd, England (Nov. 2011).

Minot, S., et al., "The Human Gut Virome: Inter-Individual Variation and Dynamic Response to Diet," Genome Research 21(10):1616-1625, Cold Spring Harbor Laboratory Press, United States (Oct. 2011).

Mitchell, P.S., et al., "Circulating Micrornas as Stable Blood-Based Markers for Cancer Detection," Proceedings of the National Academy of Sciences of the United States of America 105(30):10513-10518, National Academy of Sciences, United States (Jul. 2008).

Nachmanson, D., et al., "Targeted Genome Fragmentation With Crispr/Cas9 Improves Hybridization Capture, Reduces PCR Bias, and Enables Efficient High-accuracy Sequencing of Small Targets," Genome Research 28(10):1589-1599, Cold Spring Harbor Laboratory Press, United States (Oct. 2017).

Narayan, A., et al., "Ultrasensitive Measurement of Hotspot Mutations in Tumor DNA in Blood Using Error-suppressed Multiplexed Deep Sequencing," Cancer Research 72(14):3492-3498, American Association for Cancer Research, United States (Jul. 2012).

Nasu, A., et al., "Genetic Heterogeneity of Hepatitis C Virus in Association With Antiviral Therapy Determined by Ultra-deep Sequencing," PloS One 6(9):e24907, Public Library of Science, United States (2011).

NEB Expressions, New England BioLabs, https://web.archive.org/web/20080321144426/http://www.neb.com/nebecomm/tech_reference/neb_transcripts.asp (Feb. 23, 2022) (IPR2022-00816 Ex. 1015).

Nielsen, R., et al., "Genotype and Snp Calling From Next-Generation Sequencing Data," Nature Reviews. Genetics 12(6):443-451, Nature Publishing Group, England (Jun. 2011).

Nisha, K. and Deshwal, R.K., "Antioxidants and Their Protective Action Against DNA Damage," International Journal of Pharmacology and Pharmaceutical Sciences 3(Suppl. 4):28-32 (May 2011).

Out, A. A., et al., "Deep Sequencing to Reveal New Variants in Pooled DNA Samples," Human Mutation 30(12):1703-1712, Wiley-Liss, United States (Dec. 2009).

Ozsolak, F., et al., "Direct RNA Sequencing," Nature 461(7265):814-818, Macmillan Publishers Limited, United States (Sep. 2009).

Park, G., et al., "Characterization of Background Noise in Capture-based Targeted Sequencing Data," Genome Biology 18(136):1-13, Biomed Central Ltd, England (Jul. 2017).

Parsons, T.J., et al., "A High Observed Substitution Rate in the Human Mitochondrial DNA Control Region," Nature Genetics 15(4):363-368, Nature Publishing Co, United States (Apr. 1997).

Pecuchet, N., et al., "Analysis of Base-Position Error Rate of Next-Generation Sequencing to Detect Tumor Mutations in Circulating DNA," Clinical Chemistry 62(11):1492-1503, Oxford University Press, England (Nov. 2016).

Perakis, S., et al., "Chapter 3: Advances in Circulating Tumor DNA Analysis," Advances in Clinical Chemistry 80:73-153, Elsevier, Netherlands (2017).

Quail, M.A., et al., "A Large Genome Center's Improvements to the Illumina Sequencing System," Nature Methods 5(12):1005-1010, Nature Publication Group, United States (Dec. 2008).

Quinlan, A.R., et al., "Pyrobayes: an Improved Base Caller for Snp Discovery in Pyrosequences," Nature Methods 5(2):179-181, Nature Publication Group, United States (Jan. 2008).

Ran, F.A., et al., "Genome Engineering using the CRISPR-Cas9 System," Nature Protocols 8(11):2281-2308, Nature Pub. Group, England (Nov. 2013).

Redon, R., et al., "Global Variation in Copy Number in the Human Genome," Nature 444(7118):444-454, Nature Publishing Group, England (Nov. 2006).

Rizzo, J.M and Buck, M.J., "Key Principles and Clinical Applications of "Next-Generation" DNA Sequencing," Cancer Prevention Research 5(7):887-900, American Association for Cancer Research, United States (Jul. 2012).

Roberts, C.H., et al., "Short Template Amplicon and Multiplex Megaprimer-enabled Relay (Stammer) Sequencing, a Simultaneous Approach to Higher Throughput Sequence-based Typing of Polymorphic Genes," Immunogenetics 62(4):253-260, Springer Verlag, United States (Apr. 2010).

Robinson, J.T., et al., "Integrative Genomics Viewer," Nature Biotechnology 29(1):24-26, Nature America Publishing, United States (Jan. 2011).

Salk, J. J., and Kennedy, S. R., "Next-Generation Genotoxicology: Using Modern Sequencing Technologies to Assess Somatic Mutagenesis and Cancer Risk," Environ Mol Mutagen 61(1):135-151, Wiley Online Library, United States (published online Nov. 2019, published in print Jan. 2020).

Salk, J.J., et al., "Mutational Heterogeneity in Human Cancers: Origin and Consequences," Annual Review of Pathology 5:51-75, Annual Reviews, United States (2010).

Salk, J.J., et al., "Passenger Mutations as a Marker of Clonal Cell Lineages in Emerging Neoplasia," Seminars in Cancer Biology 20(5):294-303, Academic Press, England (Oct. 2010).

Schmitt, M. W., et al., "Detection of ultra-rare mutations by next-generation sequencing," Proc Natl Acad Sci USA 109(36):14508-14513, National Academy of Science, United States (2012).

Schmitt, M. W., et al., "Sequencing small genomic targets with high efficiency and extreme accuracy," Nature Methods 12(5):423-425, Nature Publishing Group, United States (May 2015).

(56) References Cited

OTHER PUBLICATIONS

Schwarzenbach, H., et al., "Cell-free Nucleic Acids as Biomarkers in Cancer Patients," Nature Reviews. Cancer 11(6):426-437, Nature Publishing Group, England (2011).

Schweiger, M.R., et al., "Genome-wide Massively Parallel Sequencing of Formaldehyde Fixed-paraffin Embedded (FFPE) Tumor Tissues for Copy-number- and Mutation-analysis," PloS One 4(5):e5548, Public Library of Science, United States (2009).

Sehnert, A. J., et al., "Optimal Detection of Fetal Chromosomal Abnormalities by Massively Parallel DNA Sequencing of Cell-free Fetal DNA From Maternal Blood," Clinical Chemistry 57(7):1042-1049, Oxford University Press, England (Jul. 2011).

Shen, Y., et al., "A Snp Discovery Method to Assess Variant Allele Probability From Next-generation Resequencing Data," Genome Research 20(2):273-280, Cold Spring Harbor Laboratory Press, United States (Feb. 2010).

Shendure, J and Ji, H., "Next-Generation DNA Sequencing," Nature Biotechnology 26(10):1135-1145, Nature America Publishing, United States (Oct. 2008).

Shibutani, S., et al., "Insertion of Specific Bases During DNA Synthesis Past the Oxidation-damaged Base 8-oxodg," Nature 349(6308):431-434, Nature Publishing Group, England (Jan. 1991).

Shin, G., et al., "CRISPR-Cas9-Targeted Fragmentation and Selective Sequencing Enable Massively Parallel Microsatellite Analysis," Nature Communications 8:14291, Nature Publishing Group, England (Feb. 2017).

Shiroguchi, K., et al., "Digital RNA Sequencing Minimizes Sequence-Dependent Bias and Amplification Noise With Optimized Single-molecule Barcodes," Proceedings of the National Academy of Sciences of the United States of America 109(4):1347-1352, National Academy of Sciences, United States (Jan. 2012).

Song, C.X., et al., "Sensitive and Specific Single-molecule Sequencing of 5-hydroxymethylcytosine," Nature Methods 20;9(1):75-77, Nature Pub, United States (Nov. 2011).

Song, S., et al., "DNA Precursor Asymmetries in Mammalian Tissue Mitochondria and Possible Contribution to Mutagenesis Through Reduced Replication Fidelity," Proc Natl Acad Sci USA 102(14):4990-4995, National Academy of Sciences, United States (Apr. 2005).

Sparks, A.B., et al., "Selective Analysis of Cell-free DNA in Maternal Blood for Evaluation of Fetal Trisomy," Prenatal Diagnosis 32(1):3-9, New York, England (Jan. 2012).

Stiller, M., et al., "Patterns of Nucleotide Misincorporations During Enzymatic Amplification and Direct Large-scale Sequencing of Ancient DNA," Proceedings of the National Academy of Sciences of the United States of America 103(37):13578-13584, National Academy of Sciences, United States (Sep. 2006).

Stoneking, M., et al., "Hypervariable Sites in the MtDNA Control Region Are Mutational Hotspots," American Journal of Human Genetics 67(4):1029-1032, Cell Press, United States (Oct. 2000).

Summerer, D., "Enabling technologies of genomic-scale sequence enrichment for targeted high-throughput sequencing," Genomics 94(6):363-368, Academic Press, United States (Dec. 2009).

Supporting Information for Kinde, I., et al., "Detection and Quantification of Rare Mutations With Massively Parallel Sequencing," Proc Natl Acad Sci USA 108(23):9530-9535, National Academy of Sciences, United States, 10 pages (Jun. 2011). Accessed at URL:[https://www.pnas.org/doi/suppl/10.1073/pnas.1105422108/suppl_file/pnas.201105422si.pdf] on Mar. 10, 2022, 10 pages.

Supporting Information for Schmitt, M. W., et al., "Detection of Ultra-Rare Mutations by Next-Generation Sequencing," Proc Natl Acad Sci USA 109(36):14508-14513, National Academy of Science, United States (2012). Corrected Mar. 27, 2013. Accessed from URL:[https://www.pnas.org/doi/suppl/10.1073/pnas.1208715109/suppl_file/pnas.201208715si.pdf] on May 10, 2022, 3 pages.

Supporting Information for Shiroguchi, K., et al., "Digital RNA Sequencing Minimizes Sequence-Dependent Bias and Amplification Noise With Optimized Single-molecule Barcodes," Proc Natl Acad Sci USA109(4):1347-1352, National Academy of Sciences, United States (Jan. 2012). Accessed at URL:[https://www.pnas.org/doi/suppl/10.1073/pnas.1118018109/suppl_file/pnas.201118018si.pdf] on Mar. 10, 2022, 8 pages.

Teer, J. K., et al, "Systematic comparison of three genomic enrichment methods for massively parallel DNA sequencing," Genome Research 20:1420-1431, Cold Spring Harbor Laboratory Press, United States (2010).

Thomas, D.C., et al., "Fidelity of Mammalian DNA Replication and Replicative DNA Polymerases," Biochemistry 30(51):11751-11759, American Chemical Society, United States (Dec. 1991).

Travers, K.J., et al., "A Flexible and Efficient Template Format for Circular Consensus Sequencing and SNP Detection," Nucleic Acids Research 38(15):e159, Oxford University Press, England (Aug. 2010).

Vandenbroucke, I., et al., "Minor Variant Detection in Amplicons Using 454 Massive Parallel Pyrosequencing: Experiences and Considerations for Successful Applications," Biotechniques 51(3):167-177, Future Science, England (Sep. 2011).

Vermulst, M., et al., "Mitochondrial Point Mutations Do Not Limit the Natural Lifespan of Mice," Nature Genetics 39(4):540-543, Nature Publication Co, United States (Apr. 2007).

Wagle, N., et al., "High-throughput Detection of Actionable Genomic Alterations in Clinical Tumor Samples by Targeted, Massively Parallel Sequencing," Cancer Discovery 2(1):82-93, American Association for Cancer Research, United States (Jan. 2012).

Wang, C., et al., "Characterization of Mutation Spectra With Ultra-Deep Pyrosequencing: Application to HIV-1 Drug Resistance," Genome Research 17(8):1195-201, Cold Spring Harbor Laboratory Press, United States (Aug. 2007).

Wiemann, S., et al., "Simultaneous on-line DNA Sequencing on Both Strands With Two Fluorescent Dyes," Analytical Biochemistry 224(1):117-121, Elsevier, United States (Jan. 1995).

Winters, M., et al., "Are We Fishing or Catching? Evaluating the Efficiency of Bait Capture of Codis Fragments," Forensic Science International. Genetics 29:61-70, Elsevier, Netherlands (Jul. 2017).

Yang, J., et al., "Unbiased Parallel Detection of Viral Pathogens in Clinical Samples by Use of a Metagenomic Approach," Journal of Clinical Microbiology 49(10):3463-3469, American Society for Microbiology, United States (Oct. 2011).

Yuan, B., et al., "High-throughput Analysis of the Mutagenic and Cytotoxic Properties of DNA Lesions by Next-generation Sequencing," Nucleic Acids Research 39(14):5945-5954, Oxford University Press, England (Aug. 2011).

Zagordi, O., et al., "Error Correction of Next-Generation Sequencing Data and Reliable Estimation of HIV Quasispecies," Nucleic Acids Research 38(21):7400-7409, Oxford University Press, England (Nov. 2010).

Zheng, Z., et al., "Anchored Multiplex PCR for Targeted Next-Generation Sequencing," Nature Medicine 20(12):1479-1484, Nature Publishing Company, United States (Dec. 2014).

International Search Report and Written Opinion dated Jan. 16, 2019 in International Application No. PCT/US2018/059908, ISA, United States, 9 pages.

Salk, J.J., et al., "Enhancing the accuracy of next-generation sequencing for detecting rare and subclonal mutations," Nature Reviews Genetics 19:269-285, Nature Publishing Group, United Kingdom (May 2018).

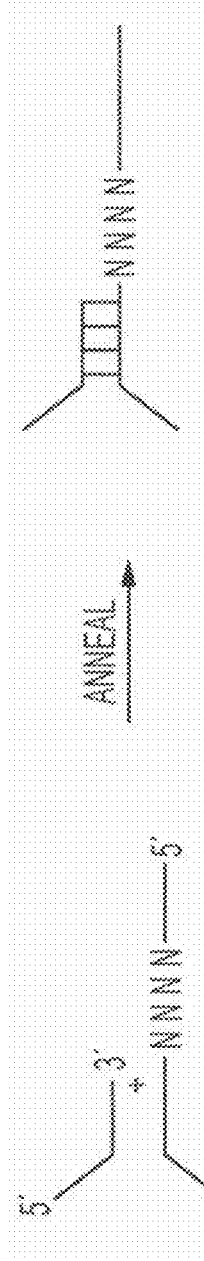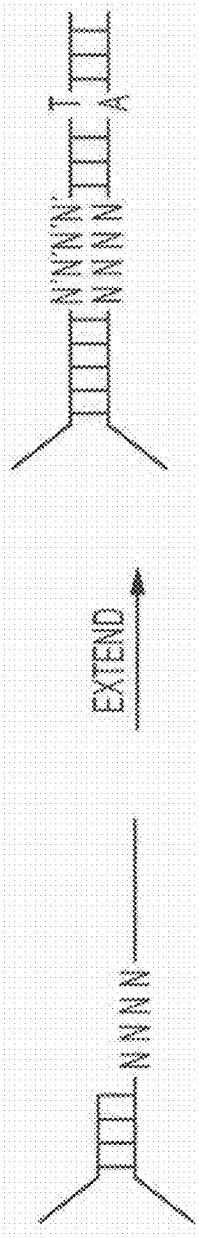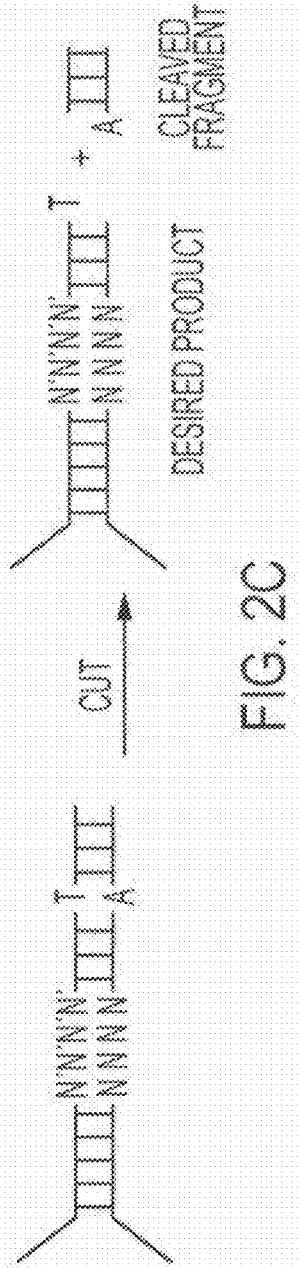

REAGENTS AND ADAPTERS FOR NUCLEIC ACID SEQUENCING AND METHODS FOR MAKING SUCH REAGENTS AND ADAPTERS

CROSS-REFERENCE TO RELATED APPLICATIONS

This application claims priority to U.S. provisional patent application No. 62/583,462, filed Nov. 8, 2017, the disclosures of which are hereby incorporated by reference in their entirety.

BACKGROUND

Duplex Sequencing is a method for producing error-corrected nucleic acid sequence reads from double-stranded nucleic acid molecules. In certain aspects of the technology, Duplex Sequencing can be used to independently sequence both strands of individual nucleic acid molecules in such a way that the derivative sequence reads can be recognized as having originated from the same double-stranded nucleic acid parent molecule during massively parallel sequencing, but also differentiated from each other as distinguishable entities following sequencing. The resulting sequence reads from each strand are then compared for the purpose of obtaining an error-corrected sequence of the original double-stranded nucleic acid molecule, known as a Duplex Consensus Sequence. The process of Duplex Sequencing makes it possible to confirm whether one or both strands of an original double-stranded nucleic acid molecule are represented in the generated sequencing data used to form a Duplex Consensus Sequence.

The high degree of error-correction provided by the strand-comparison technology of Duplex Sequencing reduces sequencing errors of double-stranded nucleic acid molecules by multiple orders of magnitude as compared with standard next-generation sequencing methods. The reduction in sequencing errors improves the accuracy of sequencing reads in nearly all types of double-stranded nucleic acid molecules, however the utility of this is greatest where the molecular population being sequenced is heterogeneous (i.e. a minor subset of the molecules carry a sequence variant that others do not). The error rate of standard next-generation sequencing is on the approximate order of $1/100$-$1/1000$ and when fewer than $1/100$-$1/1000$ of the molecules carry a sequence variant, the presence of it is obscured by the background error rate of the sequencing process. Duplex Sequencing, on the other hand can accurately detect extremely low frequency variants due to the high degree of error correction obtained.

In addition to low frequency variant detection applications, Duplex Sequencing is also well suited for accurate genotyping of difficult-to-sequence regions of the genome (homopolymers, microsatellites, G-tetraplexes etc.) where the error rate of standard sequencing is especially high. In highly damaged DNA (oxidation, deamination, etc.), which occur through fixation processes (i.e. FFPE in clinical pathology) or ancient DNA or in forensic applications where material has been exposed to harsh chemicals or environments, Duplex Sequencing is particularly useful to reduce the high resulting level of error that damage confers. Additional non-limiting examples of the utility of Duplex Sequencing can be found in Salk et al, Nature Reviews Genetics 2018, PMID 29576615, which is incorporated by reference herein its entirety.

Methods incorporating Duplex Sequencing may include ligation of one or more sequencing adapters to a target double-stranded nucleic acid molecule, comprising a first strand target nucleic acid sequence and a second strand nucleic acid sequence, to produce a double-stranded target nucleic acid complex. The use of highly pure sequencing adapters for Duplex Sequencing, or any next-generation sequencing technology, is important for obtaining reproducible data of high quality and maximizing sequence yield of a sample (i.e., the relative percentage of inputted molecules that are converted to independent sequence reads). It is particularly important with Duplex Sequencing because of the need to successfully recover both strands of the original duplex molecules. Current basic methods of adapter synthesis may lead to the accumulation of incomplete intermediates and byproducts among the desired adapter product creating inefficiencies in nucleic acid library preparation and loss of sequencing information. This is particularly true of certain forms of Duplex Sequencing adaptors which are made in a way that involve a polymerase extension and other enzymatic or chemical steps that may not be 100% efficient. Accordingly, an unmet need exists for enhanced methods and reagents for synthesizing purified sequencing adapters, and especially for use with Duplex Sequencing.

SUMMARY

Herein are described a variety of methods and reagents for producing sequencing adapters for use in nucleic acid sequencing applications, such as Duplex Sequencing. These specific embodiments are directed at improving adapter purity, manufacturing efficiency, reproducibility, cost, and flexibility of design.

In a first aspect, the present invention provides methods for preparing a duplex adapter, including the steps of annealing an elongation strand and a template strand at a complementary region, wherein the template strand comprises an identifier sequence and a capture label to form a first intermediate duplex adapter product, extending the elongation strand to at least partially duplicate the identifier sequence to form a second intermediate duplex adapter product, cutting the second intermediate duplex adapter product to form the duplex adapter and a cleaved by-product comprising the capture label, and removing undesired products to form a duplex adapter.

In some embodiments, the capture label is at a 5' end of the template strand such that non-annealed template strands, first and second intermediate duplex adapter products and by-products comprise the capture label. In some embodiments, undesired products include non-annealed template strands, first and second intermediate duplex adapter products and by-products. In some embodiments, provided methods further comprise providing a surface comprising an extraction moiety configured to bind the capture label. In some embodiments, the annealing, extending, and/or cutting steps occur in a liquid solution, and wherein the liquid solution is exposed to the surface following the cutting step. In some embodiments, the template strand is bound to the surface prior to the annealing step. In some embodiments, the template strand is bound to the surface via the capture label during the annealing and extending steps. In some embodiments, provided methods further comprise collecting a purified duplex adapter product. In some embodiments, the capture label is a first capture label at a 5' end of the template strand, and wherein the template strand comprises a second capture label at a 3' end, and the method further includes the steps of providing a second surface comprising a second extraction moiety, and cutting a 3' region of the template strand to release the duplex adapter from the second surface. In some embodiments, the first and second capture labels are different. In some embodiments, the first and second capture labels are the same. In some embodiments, the template strand and the elongation strand are linked by a linker domain. In some embodiments, the linker domain comprises nucleotides. In some embodiments, the linker domain forms a loop comprising single-stranded nucleotides. In some embodiments, the linker domain contains one or more modified nucleotides or non-nucleotide molecules. In some embodiments, extending the elongation strand comprises extending the elongation strand from a 3' end of the elongation strand by enzymatic reaction. In some embodiments, the first and second cut sites comprise at least one of a modified nucleotide or non-nucleotide molecule, and a restriction endonuclease recognition site. In some embodiments, the template strand comprises a hairpin loop structure having the capture label.

In a second aspect, the present disclosure provides methods for preparing a duplex adapter including the steps of annealing an elongation strand and a template strand at a complementary region, wherein the template strand comprises an identifier sequence, a first capture label, a first cut site, a second capture label, and a second cut site to form a first intermediate duplex adapter product, wherein the first capture label is attached to the template strand via the first cut site, extending the elongation strand to at least partially duplicate the identifier sequence to form a second intermediate duplex adapter product, cutting the second intermediate duplex adapter product at the second cut site to form the duplex adapter and a cleaved by-product comprising the second capture label, and removing undesired products, cutting the first cut site to release the duplex adapter, and removing additional undesired products.

In some embodiments, provided methods further comprise providing at least one extraction moiety configured to bind the first capture label, and capturing undesired products that include the first capture label. In some embodiments, provided methods further comprise providing at least one extraction moiety configured to bind the second capture label, and capturing undesired products that include the second capture label. In some embodiments, the extraction moiety is bound to a surface. In some embodiments, undesired products comprise one or more of excess template strand, excess elongation strand, non-extended or incompletely extended pre-adapter complexes, and cleavage fragment byproducts.

In a third aspect, the present disclosure provides methods for preparing a set of duplex sequencing adapters having a double-stranded identifier sequence including the steps of providing oligonucleotide synthesis solid supports comprising a plurality of template strands bound thereto, wherein the template strands comprise a nucleotide sequence extending from the oligonucleotide synthesis solid support to a 5' terminal end, and wherein a portion of the nucleotide sequence includes an identifier sequence that distinguishes each template strand from the other template strands, annealing an elongation strand to each template strand at a complementary region to form a plurality of preliminary sequencing adapters, extending each elongation strand in a 5' to 3' direction such that the identifier sequence is present on each strand of each preliminary sequencing adapter, and releasing the preliminary sequencing adapters from the oligonucleotide synthesis solid supports to provide a set of duplex sequencing adapters having a double-stranded identifier sequence.

In some embodiments, each preliminary sequencing adapter comprises two single-stranded arms proximal to the oligonucleotide synthesis solid support. In some embodiments, provided methods further comprise enzymatically cutting a 3' end of the duplex sequencing adapters to form a 3' ligateable end. In some embodiments, provided methods further comprise synthesizing the plurality of template strands on the oligonucleotide synthesis solid supports. In some embodiments, the oligonucleotide synthesis solid supports are controlled pore glass (CPG) beads or macroporous polystyrene (MPPS) beads.

In a fourth aspect, the present disclosure provides methods for making a duplex adapter including the steps of providing a template strand having an identifier sequence, a first hairpin loop structure at a 5' region and a second hairpin loop structure at a 3' region, wherein the first hairpin loop structure comprises a first single-stranded nucleotide loop having a first cut site and a 5' double-stranded stem portion, the second hairpin loop structure comprises a second single-stranded nucleotide loop having a capture label and a 3' double-stranded stem portion having a second cut site, and the template strand further comprises an identifier sequence in a mid-region between the 5' double-stranded stem portion and the 3' double-stranded stem portion, enzymatically extending the template strand from a 3' terminal end to meet the 5' terminal end such that the identifier sequence is double-stranded, and cutting the first and second cut sites to provide a duplex adapter having a single stranded portion at a 5' end of the duplex adapter, and having a ligation domain at a 3' end of the duplex adapter.

In a fifth aspect, the present disclosure provides methods for making a duplex adapter, including the steps of providing a template strand comprising, in a 5' to 3' direction, a single-stranded portion having a modified nucleotide or non-nucleotide molecule and an identifier sequence, a double-stranded stem portion having a cut site, and a single-stranded nucleotide loop having a capture label, wherein the stem portion comprises a region of complementary sequence between the 3' region of the template strand and a mid-region of the template strand, thereby forming the single-stranded nucleotide loop, immobilizing the template strand via the capture label, extending the single-stranded portion having the identifier sequence by from a 3' terminal end, cleaving the template strand at the modified nucleotide, removing a 5' region of the template strand to generate a 3' single-stranded region of the template strand, providing a second strand having a sequence at least partially complementary to the 3' single-stranded region of the template strand, annealing the second strand to the 3' single-stranded region of the template strand to generate a pre-adapter complex, and cutting the cut site to provide a duplex adapter having a double-stranded identifier sequence.

In a sixth aspect, the present disclosure provides methods for making a duplex adapter, including the steps of providing a template strand comprising, in a 5' to 3' direction, a single-stranded portion at a 5' region, a first hairpin loop structure, an identifier sequence, and a second hairpin loop structure, wherein the first hairpin loop structure comprises (a) a 5' double-stranded stem portion having a region of complementary sequence between the 5' region of the template strand and a mid-region of the template strand and forming a first single-stranded nucleotide loop between the region of complementarity sequence and (b) a single stranded nucleotide loop having a modified nucleotide or non-nucleotide molecule, the second hairpin loop structure comprises (a) a 3' double-stranded stem portion having a region of complementarity sequence between the 3' region of the template strand a mid-region of the template strand and forming a second single-stranded nucleotide loop between the region of complementarity sequence, (b) a cut site, and (c) a single stranded nucleotide loop having a capture label, enzymatically extending the template strand from a 3' terminal end over the 5' double-stranded stem portion of the first hairpin loop structure such that the identifier sequence and the single-stranded portion are made double-stranded, cutting the modified nucleotide or non-nucleotide molecule to create a single-stranded nick allowing for release of a single-stranded byproduct, releasing the single-stranded byproduct, and cutting the cut site to provide a duplex adapter having a single stranded portion at a 5' end of the duplex adapter, and having a ligation domain at a 3' end of the duplex adapter.

In a seventh aspect, the present disclosure provides methods for making a purified duplex sequencing adapter having a physical unique molecular identifier (UMI) on each strand, including the steps of providing a preliminary sequencing adapter comprising a double-stranded hybridized region, two single-stranded arms, an overhang comprising the physical UMI at an end of the double-stranded hybridized region that is further away from the two single stranded arms, and a capture label at 5' end of the overhang, extending one strand of the double-stranded hybridized region using the overhang as a template, thereby producing an extension product, cutting the extension product in a double-stranded region 3' to the physical UMI at a cleavage site, thereby producing a duplex sequencing adapter and a byproduct comprising nucleotides 3' of the cleavage site and the capture label, and separating the duplex sequencing adapter from undesired products to provide a purified duplex sequencing adapter having a physical UMI on each strand.

In some embodiments, a template strand comprises an index sequence.

In some embodiments, extending by enzymatic reaction comprises DNA polymerase activity. In some embodiments, the DNA polymerase is selected from Pol I, Pol II, Pol III, Pol IV, Pol V, Taq polymerase, polymerase alpha, polymerase beta, polymerase delta, polymerase lambda, polymerase sigma, polymerase epsilon, polymerase mu, polymerase zeta, polymerase nu, and polymerase theta.

In some embodiments, provided methods further comprise ligating the duplex adapter to a double stranded nucleic acid molecule. In some embodiments, the double stranded nucleic acid molecule is a double stranded DNA molecule or a double stranded RNA molecule. In some embodiments, the double stranded nucleic acid molecule comprises at least one modified nucleotide or non-nucleotide molecule.

In some embodiments, ligating comprises activity of at least one ligase. In some embodiments, the at least one ligase is selected from a DNA ligase and a RNA ligase. In some embodiments, ligating comprises ligase activity at a ligation domain. In some embodiments, the ligation domain is a nucleotide sequence from one or more degenerate or semi-degenerate nucleotides. In some embodiments, the ligation domain is a nucleotide sequence from one or more non-degenerate nucleotides. In some embodiments, the ligation domain contains one or more modified nucleotides. In some embodiments, the ligation domain comprises a T-overhang, an A-overhang, a CG-overhang, a blunt end, a recombination sequence, a restriction digest overhang, or another ligateable region. In some embodiments, at least one strand of the ligation domain is phosphorylated. In some embodiments, the ligation domain comprises a restriction endonuclease cleavage sequence.

In some embodiments, the restriction endonuclease cleavage sequence is cleaved by a restriction endonuclease to yield a blunt end, or overhang ligateable region. In some embodiments, the ligation domain is 3' to the identifier sequence. In some embodiments, the ligation domain is 5' to the identifier sequence.

In some embodiments, an identifier sequence is or comprises a single molecule identifier (SMI) sequence. In some embodiments, a SMI sequence is an endogenous SMI sequence. In some embodiments, the endogenous SMI sequence is related to shear point. In some embodiments, the SMI sequence comprises at least one degenerate or semi-degenerate nucleic acid. In some embodiments, the SMI sequence is non-degenerate. In some embodiments, the SMI sequence is a nucleotide sequence of one or more degenerate or semi-degenerate nucleotides. In some embodiments, the SMI sequence is a nucleotide sequence of one or more non-degenerate nucleotides. In some embodiments, the SMI sequence of the template strand and the SMI of the elongation strand are complementary. In some embodiments, the SMI sequence of the template strand and the SMI of the elongation strand are at least partially non-complementary. In some embodiments, the SMI sequence of the template strand and the SMI of the elongation strand are non-complementary. In some embodiments, the SMI sequence comprises at least one modified nucleotide or non-nucleotide molecule. In some embodiments, the SMI sequence comprises a primer binding domain.

In some embodiments, a modified nucleotide or non-nucleotide molecule is selected from 2-Aminopurine, 2,6-Diaminopurine (2-Amino-dA), 5-Bromo dU, deoxyUridine, Inverted dT, Inverted Dideoxy-T, Dideoxy-C, 5-Methyl dC, deoxyInosine, Super T®, Super G®, Locked Nucleic Acids, 5-Nitroindole, 2'-O-Methyl RNA Bases, Hydroxymethyl dC, Iso-dG, Iso-dC, Fluoro C, Fluoro U, Fluoro A, Fluoro G, 2-MethoxyEthoxy A, 2-MethoxyEthoxy MeC, 2-MethoxyEthoxy G, 2-MethoxyEthoxy T, 8-oxo-A, 8-oxoG, 5-hydroxymethyl-2'-deoxycytidine, 5'-methylisocytosine, tetrahydrofuran, iso-cytosine, iso-guanosine, uracil, methylated nucleotide, RNA nucleotide, ribose nucleotide, 8-oxo-G, BrdU, Loto dU, Furan, fluorescent dye, azide nucleotide, abasic nucleotide, 5-nitroindole nucleotide, and digoxenin nucleotide.

In some embodiments, a cut site is or comprises a restriction endonuclease recognition sequence.

In some embodiments, a capture label is or comprises at least one of Acrydite, azide, azide (NHS ester), digoxigenin (NHS ester), I-Linker, Amino modifier C6, Amino modifier C12, Amino modifier C6 dT, Unilink amino modifier, hexynyl, 5-octadiynyl dU, biotin, biotin (azide), biotin dT, biotin TEG, dual biotin, PC biotin, desthiobiotin TEG, thiol modifier C3, dithiol, thiol modifier C6 S-S, and succinyl groups.

In some embodiments, an extraction moiety is or comprises at least one of amino silane, epoxy silane, isothiocyanate, aminophenyl silane, aminopropyl silane, mercapto silane, aldehyde, epoxide, phosphonate, streptavidin, avidin, a hapten recognizing an antibody, a particular nucleic acid sequence, magnetically attractable particles (Dynabeads), and photolabile resins.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

Many aspects of the present disclosure can be better understood with reference to the following drawings. The components in the drawings are not necessarily to scale. Instead, emphasis is placed on illustrating various principles of the present disclosure. All examples below are to be taken as non-limiting representative embodiments of concepts described herein.

FIG. 1 depicts an Oligonucleotide Annealing (OA) method for making Duplex Adapters in accordance with the prior art.

FIG. 2 depicts an Enzymatic Extension (EE) method for making Duplex Adapters in accordance with the prior art. FIG. 2A illustrates annealing an elongation strand to a template strand at an at least partially complementary region. FIG. 2B illustrates extension of the elongation strand by an enzymatic reaction, such as involving a polymerase, resulting in the formation of a double-stranded sequence having a double-stranded SMI. FIG. 2C illustrates enzymatic, chemical or other forms of cleavage at a region (e.g., a ligation domain) of the double-stranded sequence resulting in a ligateable end on the desired adapter product, and a cleaved fragment.

FIG. 10 depicts another embodiment of a method for an adapter synthesis scheme using single or double capture labels and a cleavable linker.

FIG. 11 depicts incorporation of an index sequence during adapter synthesis.

FIG. 13 depicts other embodiments of methods of a reverse adapter synthesis scheme. FIGS. 13A and 13B illustrate variations of embodiments using modified or non-standard base incorporation to release the adapter from a functionalized surface while forming a ligateable end, and/or to cleave the 5' hairpin feature to form a Y-shaped adapter complex.

DEFINITIONS

Figure 1A:
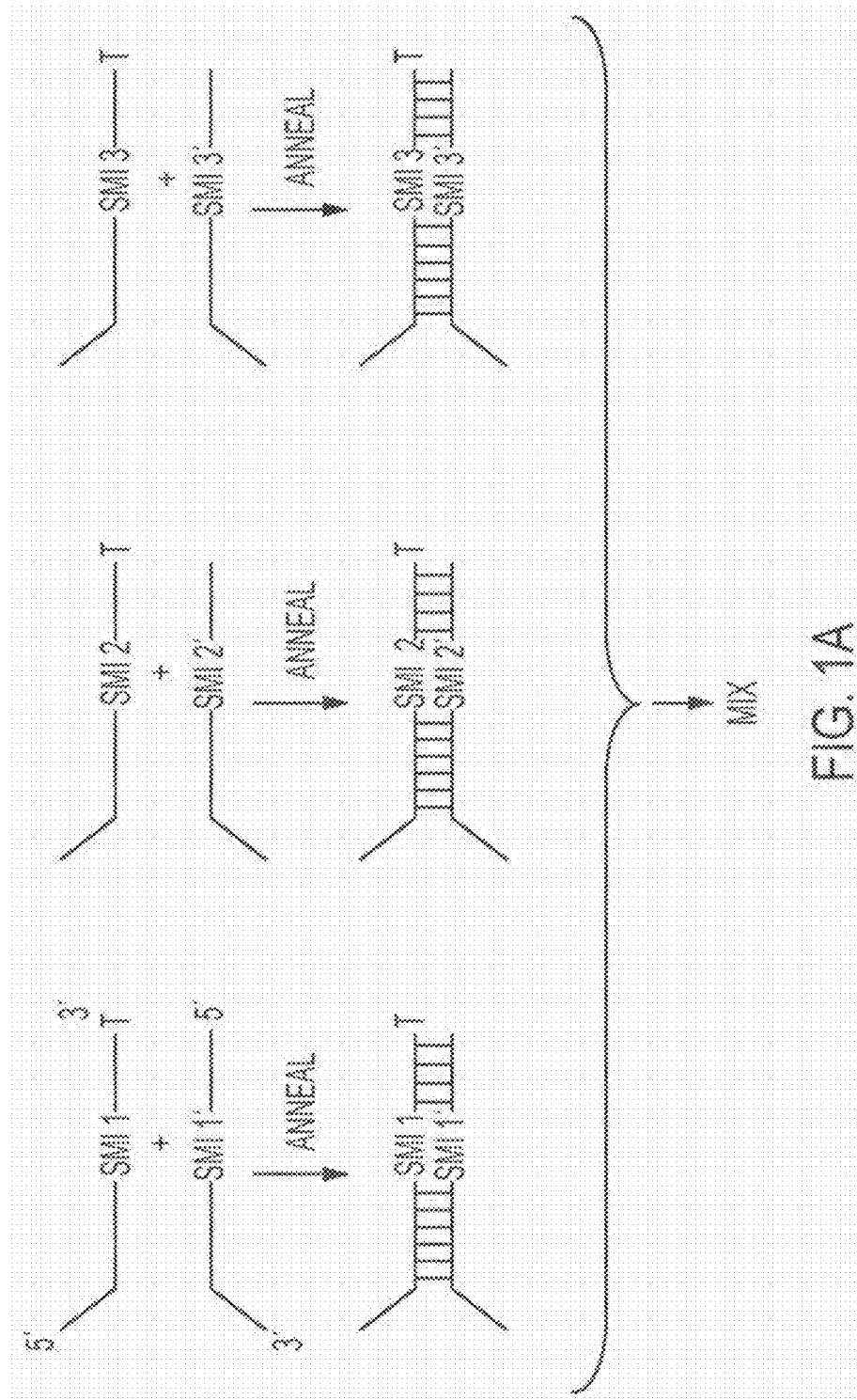
FIG. 1A illustrates direct annealing of at least partially complementary adapter strands to form a pool of adapters with substantially unique, complementary single molecule identifier (SMI) sequences.

In order for the present disclosure to be more readily understood, certain terms are first defined below. Additional definitions for the following terms and other terms are set forth throughout the specification.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; (iv) the terms "about" and "approximately" may be understood to permit standard variation as would be understood by those of ordinary skill in the art; and (v) where ranges are provided, endpoints are included. As used in this application, the term "comprise" and variations of the term, such as "comprising" and "comprises," are not intended to exclude other additives, components, integers or steps.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present technology. Alternatively, or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, hexose or Locked Nucleic acids) as compared with those in commonly occurring natural nucleic acids. In some embodiments, a nucleic acid has a nucleotide sequence that encodes a functional gene product such as an RNA or protein. In some embodiments, a nucleic acid includes one or more introns. In some embodiments, a nucleic acid may be a non-protein coding RNA product, such as a microRNA, a ribosomal RNA, or a CRISPER/Cas9 guide RNA. In some embodiments, a nucleic acid serves a regulatory purpose in a genome. In some embodiments, a nucleic acid does not arise from a genome. In some embodiments, a nucleic acid includes intergenic sequences. In some embodiments, a nucleic acid derives from an extrachromosomal element or a non-nuclear genome (mitochondrial, chloroplast etc.), In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double-stranded. In some embodiments a nucleic acid has a nucleotide sequence comprising at least one element that encodes, or is the complement of a sequence that encodes, a polypeptide. In some embodiments, a nucleic acid has enzymatic activity. In some embodiments the nucleic acid serves a mechanical function, for example in a ribonucleoprotein complex or a transfer RNA. In some embodiments a nucleic acid function as an aptamer. In some embodiments a nucleic acid may be used for data storage. In some embodiments a nucleic acid may be chemically synthesized in vitro.

Strand Defining Element (SDE): As used herein, the term "Strand Defining Element" or "SDE", refers to any material which allows for the identification of a specific strand of a double-stranded nucleic acid material and thus differentiation from the other/complementary strand (e.g., any material that renders the amplification products of each of the two single-stranded nucleic acids resulting from a target double-stranded nucleic acid substantially distinguishable from each other after sequencing or other nucleic acid interrogation). In some embodiments, a SDE may be or comprise one or more segments of substantially non-complementary sequence within an adapter sequence. In particular embodiments, a segment of substantially non-complementary sequence within an adapter sequence can be provided by an adapter molecule comprising a Y-shape or a "loop" shape. In other embodiments, a segment of substantially non-complementary sequence within an adapter sequence may form an unpaired "bubble" in the middle of adjacent complementary sequences within an adapter sequence. In other embodiments a SDE may encompass a nucleic acid modification. In some embodiments a SDE may comprise physical separation of paired strands into physically separated reaction compartments. In some embodiments a SDE may comprise a chemical modification. In some embodiments a SDE may comprise a modified nucleic acid. In some embodiments a SDE may relate to a sequence variation in a nucleic acid molecule caused by random or semi-random damage, chemical modification, enzymatic modification or other modification to the nucleic acid molecule. In some embodiments the modification may be deamination of methylcytosine. In some embodiments the modification may entail sites of nucleic acid nicks. Various embodiments of SDEs are further disclosed in International Patent Publication No. WO2017/100441, which is incorporated by reference herein in its entirety.

Single Molecule Identifier (SMI): As used herein, the term "single molecule identifier" or "SMI", (which may be referred to as a "tag" a "barcode", a "molecular barcode", a "molecular identifier", an "identifier sequence", a "Unique Molecular Identifier", or "UMI", among other names) refers to any material (e.g., a nucleotide sequence, a nucleic acid molecule feature) that is capable of distinguishing an individual molecule in a large heterogeneous population of molecules. In some embodiments, a SMI can be or comprise an exogenously applied SMI. In some embodiments, an exogenously applied SMI may be or comprise a degenerate or semi-degenerate sequence. In some embodiments, substantially degenerate SMIs may be known as Random Unique Molecular Identifiers (R-UMIs). In some embodiments an SMI may comprise a code (for example a nucleic acid sequence) from within a pool of known codes. In some embodiments pre-defined SMI codes are known as Defined Unique Molecular Identifiers (D-UMIs). In some embodiments, a SMI can be or comprise an endogenous SMI. In some embodiments, an endogenous SMI may be or comprise information related to specific shear-points of a target sequence, or features relating to the terminal ends of individual molecules comprising a target sequence. In some embodiments an SMI may relate to a sequence variation in a nucleic acid molecule caused by random or semi-random damage, chemical modification, enzymatic modification or other modification to the nucleic acid molecule. In some embodiments the modification may be deamination of methylcytosine. In some embodiments the modification may entail sites of nucleic acid nicks. In some embodiments, an SMI may comprise both exogenous and endogenous elements. In some embodiments an SMI may comprise physically adjacent SMI elements. In some embodiments SMI elements may be spatially distinct in a molecule. In some embodiments an SMI may be a non-nucleic acid. In some embodiments an SMI may comprise two or more different types of SMI information. Various embodiments of SMIs are further disclosed in International Patent Publication No. WO2017/100441, which is incorporated by reference herein in its entirety.

Elongation strand: As used herein, the term "elongation strand" or "elongation molecule" refers to a polynucleic acid molecule used for adapter synthesis. In some embodiments, the elongation strand is a synthesized oligonucleotide of defined sequence. In other embodiments the elongation strand is a synthesized oligonucleotide having one or more undefined (e.g., random or semi-random) nucleotides. In some embodiments, the elongation strand is comprised of four or more nucleotides. In some embodiments, the elongation strand comprises a SDE. For example, the elongation strand may include one or more portions that are not complementary with respect to a template strand. In some embodiments, the elongation strand comprises a SMI. In some embodiments, the elongation strand comprises an index sequence (e.g., index barcode, index tag) or other identification tag. In some embodiments, the elongation strand comprises a primer binding site. In some embodiments, the elongation strand comprises a primer binding site within the SDE. In some embodiments, the template strand comprises a read primer sequence. In some embodiments, the elongation strand comprises one or more regions complementary to a template strand.

Template strand: As used herein, the term "template strand" or "template molecule" refers to a polynucleic acid molecule used for adapter synthesis. In some embodiments, the template strand is comprised of about 10 or more, but preferably 20 or more nucleotides. In some embodiments, the template strand is a synthesized oligonucleotide of defined sequence. In other embodiments the template strand is a synthesized oligonucleotide having one or more undefined (e.g., random or semi-random) nucleotides. In some embodiments, the template strand has regions of self-complementarity. In some embodiments, the template strand comprises a SDE. For example, the template strand may include one or more portions that are not complementary with respect to an elongation strand. In some embodiments, the template strand comprises a SMI. In some embodiments, the template strand comprises an index sequence (e.g., index barcode, index tag) or other identification tag. In some embodiments, the template strand comprises a primer binding site. In some embodiments, the template strand comprises a primer binding site within the SDE. In some embodiments, the template strand comprises a read primer sequence. In some embodiments, the template strand comprises one or more regions complementary to an elongation strand. In some embodiments, the template strand comprises one or more modified or non-standard nucleotides. In some embodiments, such modified or non-standard nucleotides are enzymatically cleavable. In some embodiments, a template strand comprises a ligation domain. In some embodiments, the ligation domain comprises a cleavable portion or recognition site. In some embodiments, a template strand comprises a capture label configured to bind a binding partner moiety.

Capture label: As used herein, the term "capture label" (which may also be referred to as a "capture tag", "capture moiety", "affinity label", "affinity tag", "epitope tag", "tag", "prey" moiety or chemical group, among other names) refers to a moiety that can be integrated into, or onto, a target molecule, or substrate, for the purposes of purification. In some embodiments, the capture label is selected from a group comprising a small molecule, a nucleic acid, a peptide, or any uniquely bindable moiety. In some embodiments, the capture label is affixed to the 5' of a nucleic acid molecule. In some embodiments, the capture label is affixed to the 3' of a nucleic acid molecule. In some embodiments, the capture label is conjugated to a nucleotide within the internal sequence of a nucleic acid molecule not at either end. In some embodiments, the capture label is a sequence of nucleotides within the nucleic acid molecule. In some embodiments, the capture label is selected from a group of biotin, biotin deoxythymidine dT, biotin NHS, biotin TEG, desthiobiotin NHS, digoxigenin NHS, DNP TEG, thiols, among others. In some embodiments, capture labels include, without limitation, biotin, avidin, streptavidin, a hapten recognized by an antibody, a particular nucleic acid sequence and magnetically attractable particles. In some embodiments, chemical modification (e.g., Acridite™-modified, adenylated, azide-modified, alkyne-modified, I-Linker™-modified etc.) of nucleic acid molecules can serve as a capture label.

Extraction moiety: As used herein the term "extraction moiety" (which may also be referred to as a "binding partner", an "affinity partner", a "bait" moiety or chemical group among other names) refers to an isolatable moiety or any type of molecule that allows affinity separation of nucleic acids bearing the capture label from nucleic acids lacking the capture label. In some embodiments, the extraction moiety is selected from a group comprising a small molecule, a nucleic acid, a peptide, an antibody or any uniquely bindable moiety. The extraction moiety can be linked or linkable to a solid phase or other surface for forming a functionalized surface. In some embodiments, the extraction moiety is a sequence of nucleotides linked to a surface (e.g., a solid surface, bead, magnetic particle, etc.). In some embodiments, the extraction moiety is selected from a group of avidin, streptavidin, an antibody, a polyhistadine tag, a FLAG tag or any chemical modification of a surface for attachment chemistry. Non-limiting examples of these latter include azide and alkyne groups which can form 1,2,3-triazole bonds via "Click" methods, or thiol an azide and terminal alkyne, thiol-modified surfaces can covalently react with Acrydite-modified oligonucleotides and aldehyde and ketone modified surfaces which can react to affix I-Linker™ labeled oligonucleotides.

Functionalized surface: As used herein, the term "functionalized surface" refers to a solid surface, a bead, or another fixed structure that is capable of binding or immobilizing a capture label. In some embodiments, the functionalized surface comprises an extraction moiety capable of binding a capture label. In some embodiments, an extraction moiety is linked directly to a surface. In some embodiments, chemical modification of the surface functions as an extraction moiety. In some embodiments, a functionalized surface can comprise controlled pore glass (CPG), magnetic porous glass (MPG), among other glass or non-glass surfaces. Chemical functionalization can entail ketone modification, aldehyde modification, thiol modification, azide modification, and alkyne modifications, among others. In some embodiments, the functionalized surface and an oligonucleotide used for adapter synthesis are linked using one or more of a group of immobilization chemistries that form amide bonds, alkylamine bonds, thiourea bonds, diazo bonds, hydrazine bonds, among other surface chemistries. In some embodiments, the functionalized surface and an oligonucleotide used for adapter synthesis are linked using one or more of a group of reagents including EDAC, NHS, sodium periodate, glutaraldehyde, pyridyl disulfides, nitrous acid, biotin, among other linking reagents.

Cut site: Also called "cleavage site" and "nick site", is the bond, or pair of bonds between nucleotides in a nucleic acid molecule. In the case of double stranded nucleic acid molecules, such as double stranded DNA, the cut site can entail bonds (commonly phosphodiester bonds) which are immediately adjacent from each other in a double stranded molecule such that after cutting a "blunt" end is formed. The cut site can also entail two nucleotide bonds that are on each single strand of the pair that are not immediately opposite from each other such that when cleaved a "sticky end" is left, whereby regions of single stranded nucleotides remain at the terminal ends of the molecules. Cut sites can be defined by particular nucleotide sequence that is capable of being recognized by an enzyme, such as a restriction enzyme, or another endonuclease with sequence recognition capability such as CRISPER/Cas9. The cut site may be within the recognition sequence of such enzymes (i.e. type 1 restriction enzymes) or adjacent to them by some defined interval of nucleotides (i.e. type 2 restriction enzymes). Cut sites can also be defined by the position of modified nucleotides that are capable of being recognized by certain nucleases. For example, abasic sites can be recognized and cleaved by endonuclease VII as well as the enzyme FPG. Uracil based can be recognized and rendered into abasic sites by the enzyme UDG. Ribose-containing nucleotides in an otherwise DNA sequence can be recognized and cleaved by RNAseH2 when annealed to complementary DNA sequences.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION

The present technology is directed to reagents and adapters for nucleic acid sequencing applications, such as Duplex Sequencing. Other aspects of the technology are directed to methods for making and using such reagents and adapters. In particular, some embodiments of the technology are directed to making a purified duplex adapter having a unique identifier sequence (e.g., an SMI) on each adapter strand. For example, various embodiments of the present technology include synthesizing and purifying a set of duplex sequencing adapters for preparing a sequence library suitable for performing Duplex Sequencing methods. Various aspects of the present technology are suitable for preparing double-stranded adapters for use in Duplex Sequencing as well as other sequencing applications.

Specific details of several embodiments of the technology are described below with reference to FIGS. 1A-13D. The embodiments can include, for example, methods for preparing a duplex adapter and associated reagents for use in such methods. Some embodiments of the technology are directed to preparing a purified duplex adapter for improving aspects of Duplex Sequencing. Although many of the embodiments are described herein with respect to synthesizing and generating adaptors and other reagents for use with Duplex Sequencing methods, other applications and uses of the adapters and reagents in addition to those described herein are within the scope of the present technology. Additionally, several other embodiments of the technology can have different configurations or procedures than those described herein. A person of ordinary skill in the art, therefore, will accordingly understand that the technology can have other embodiments with additional elements and that the technology can have other embodiments without several of the features shown and described below with reference to FIGS. 1A-13D. Various aspects of the present technology are described in detail in the following sections. The use of sections is not meant to limit the present technology.

Duplex Sequencing is a method for producing error-corrected DNA sequences from double stranded nucleic acid molecules, and which was originally described in International Patent Publication No. WO 2013/142389 and in U.S. Pat. No. 9,752,188, both of which are incorporated herein by reference. In certain embodiments, methods incorporating Duplex Sequencing may include ligation of one or more sequencing adapters to a target double stranded nucleic acid molecule, comprising a first strand target nucleic acid sequence and a second strand target nucleic sequence, to produce a double-stranded target nucleic acid complex. In various embodiments, resulting target nucleic acid complex in Duplex Sequencing can include at least one Single Molecular Identifier (SMI) sequence, which may entail an exogenously applied degenerate or semi-degenerate sequence (which may be referred to as a "tag" a "barcode", a "Unique Molecular Identifier", or "UMI", among other names), endogenous information related to the specific shear-points of the target double-stranded nucleic acid molecule, or a combination thereof. The SMI can render the target-nucleic acid molecule substantially distinguishable from the plurality of other molecules in a population being sequenced. The SMI element's substantially distinguishable feature can be independently carried by each of the single strands that form the double-stranded nucleic acid molecule such that the derivative amplification products of each strand can be recognized as having come from the same original substantially unique double-stranded nucleic acid molecule after sequencing. In other embodiments the SMI may include additional information and/or may be used in other methods for which such molecule distinguishing functionality is useful, such as those described in the above-referenced publications.

In some embodiments, each double-stranded target nucleic acid sequence complex in Duplex Sequencing can further include an element that renders the amplification products of the two single stranded nucleic acids that form the target double-stranded nucleic acid substantially distinguishable from each other after sequencing. In some embodiments this element may be called a Strand Defining Element (SDE). In one embodiment, the SDE may comprise asymmetric primer sites comprised within the sequencing adapters, or, in other arrangements, sequence asymmetries may be introduced into the adapter molecules not within the primer sequences, such that at least one position in the nucleotide sequences of the first strand target nucleic acid sequence complex and the second stand of the target nucleic acid sequence complex are different from each other following amplification and sequencing. In other embodiments, the SMI may comprise another biochemical asymmetry between the two strands that differs from the canonical nucleotide sequences A, T, C, G or U, but is converted into at least one canonical nucleotide sequence difference in the two amplified and sequenced molecules. In yet another embodiment, the SDE may be a means of physically separating the two strands before amplification, such that the derivative amplification products from the first strand target nucleic acid sequence and the second strand target nucleic acid sequence are maintained in substantial physical isolation from one and other for the purposes of maintaining a distinction between the two. Other such arrangements or methodologies for providing an SDE function that allows for distinguishing the first and second strands may be utilized, such as those described in the above-referenced publications, or other methods that serves the functional purpose described.

Various methods for synthesizing Duplex Sequencing adapters have been previously described and are further disclosed in U.S. Pat. No. 9,752,188 and in International Patent Publication No. WO2017/100441, which are both incorporated herein by reference.

Figure 1B:
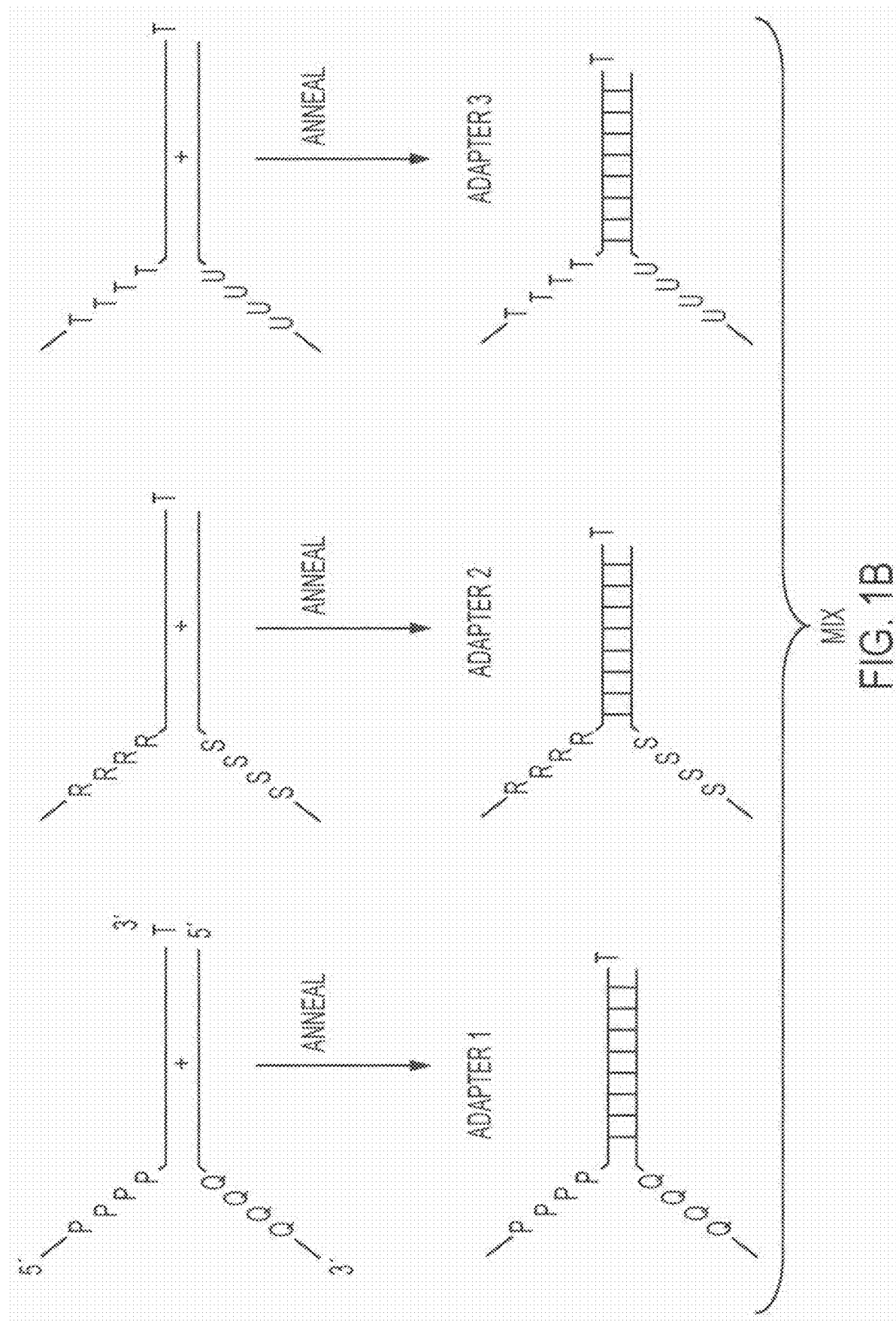
FIG. 1B illustrates direct annealing of complementary adapter strands to form a pool of adapters with unique non-complementary SMI sequences.

One method for making SMIs in Duplex Adapters includes hybridization of oligonucleotides comprising known sequences (inclusive of chemically linked oligonucleotides or two portions of single continuous oligonucleotide loop). Non-limiting examples of an Oligonucleotide Annealing (OA) method for making duplex adapters having an SMI in each strand are shown in FIG. 1A and FIG. 1B. In this approach, oligonucleotides of pre-determined known sequence and the corresponding complement sequences can be synthesized. In one embodiment shown in FIG. 1A, an oligonucleotide and its complement oligonucleotide can be annealed to form an adapter complex having a duplex SMI of predetermined sequence. Two or more adapters with different SMI sequences can then be combined to form a pool of adapters comprising two or more SMIs. Multiple adapters bearing different SMI sequences can be mixed to generate an adapter set that can be suitable for some applications of Duplex Sequencing. As illustrated, the direct annealing of complementary adapter strands to form a pool of adapters with unique complementary SMI sequences provides a set of adapters suitable for nucleic acid library preparation.

However, the SMI sequences created in the OA method of adapter synthesis do not need to be complementary. For example, FIG. 1B illustrates direct annealing of complementary adapter strands to form a pool of adapters with unique non-complementary SMI sequences. For example, oligonucleotides of predetermined known sequence can be annealed such that a single-stranded SMI in one strand can be informatically related to that on the opposite strand in such a way that amplification products derived from the two strands can be recognized as having been derived from the same starting double-stranded Duplexes. Two or more different versions of these adapters can then be combined to form a pool of two or more types of adapters comprising two or more SMIs. One non-limiting example of this Oligonucleotide Annealing (OA) method for making SMIs in Duplex Adapters is shown in FIG. 1B. Accordingly, such adapters would comprise SMI sequences in non-complementary regions (e.g., on Y-shaped arms, within a bubble, etc.). In the example illustrated in FIG. 1B, different SMIs are represented by different series of four letters (i.e. "PPPP" and "QQQQ"), that are recorded at the time of mixing as belonging together, but are at least partially non-complementary.

In both examples, substantially knowing the sequence of the individual strands that are being annealed together provides important information for later use. For example, at least in part, the SMI tag can be used to relate sequence reads that are derived from one strand to those of the other strand of the original DNA duplex. Accordingly, the adapters provide an ability to substantially distinguish those strands of a particular founding double-stranded molecule from those derived from other original double-stranded molecules in the population being sequenced.

In some instances, the OA method for making SMIs in Duplex Adapters provides simplicity of synthesis. For example, a pool of 96 different adapters can be generated by individually annealing 96 "top" strands with 96 corresponding "bottom" strands in 96 individual wells followed by mixing of the individually annealed adapters. In a non-limiting example, although synthesis of 196 individual oligonucleotides is required, the preparation of the 96 SMI tag adapter pool requires little effort beyond simply annealing oligonucleotides and mixing. If present in approximately equimolar adapter amounts, and with a Duplex SMI-containing adapter ligated to both ends of every library fragment, with use of only information from these SMI tags, there are 96×96=9216 different ways a given fragment could be labeled. Although in some applications where a large number of library fragments are sequenced, 9216 tag combinations is inadequate to substantially distinguish every library fragment from each other (i.e. if 100,000 fragments were sequenced, roughly 10 independent fragments would be expected to be tagged identically), when combined with SMI information encoded in random, semi-random or otherwise heterogeneous shear points of library molecules, the cumulative diversity from the exogenous plus endogenous SMI elements is sufficient for each library fragment to be substantially uniquely marked in such a way that it can be substantially differentiated from other molecules in the same library pool.

For applications where the nucleic acid fragments being sequenced have no, or a lesser degree of shear point diversity, less or no reliance can be placed on SMI-information related to endogenous library shear points to contribute to the aggregate SMI information. If no shear point diversity exists, the probability of a "tag clash" (i.e. where two independent molecules carry the same SMI information) becomes high when using small SMI adapter pool produced by the OA method for a typical sized sequencing run. For example, when sequencing library fragments are generated by sequence-specific enzymatic digestion, essentially all the Duplex SMI information must be contained within the adapter tags themselves. If sequencing depth exceeds the number of tag variants, tag clashes will necessarily occur, and the efficacy of duplex sequencing may decrease.

In some instances, an enzymatic extension (EE) approach to making Duplex Adapters provides a much larger number of generated SMI sequences. For example, and in one embodiment, one oligonucleotide can be hybridized to another oligonucleotide containing a degenerate or semi-degenerate nucleotide sequence on a region of non-complementarity. The hybridized oligonucleotides may then be chemically linked or may be two portions of a continuous oligonucleotide that when hybridized forms a "loop" or a "U" shape. An enzyme capable of polymerizing nucleotides can then be used to copy a single-stranded degenerate or semi-degenerate region such that a complement is synthesized. A complementary double-stranded degenerate or semi-degenerate sequence is thus produced which may serve as the at least one SMI element during Duplex Sequencing. The ligation site on the adapter molecule may be modified from this extension product by enzymatic or chemical manipulation, for example by restriction digestion, terminal transferase activity of a polymerase or other enzyme or any other method known in the art.

Although more steps are required in the EE approach, as few as two batches of oligonucleotides are needed to generate a much larger number of SMI sequences. In a particular example, for EE Duplex Adapters with a 10 base pair fully degenerate sequence, theoretically $4^{10}=\sim$sixty million SMI tags will exist. When these adapters are ligated to both ends of library fragments there are $4^{20}=\sim3.6E15$ different SMI combinations. Even when sequencing billions of library fragments where no shear point diversity exists, the probability of tag clashes are exceedingly low. One non-limiting example of an EE method for producing Duplex Sequencing adapters is illustrated in FIG. 2. With reference to FIG. 2A, the top strand, or the elongation strand, is annealed to a degenerate or semi-degenerate SMI sequence-containing bottom strand, or template strand, thereby forming a pre-adapter complex. The 3' end of the elongation strand is then extended to render both the SMI sequence and a ligation domain double-stranded, creating an un-cut adapter complex (FIG. 2B). The ligation domain cut-site of the adapter is then cleaved with a restriction endonuclease enzyme to leave a 3' "T" overhang which is compatible for ligation with a 3' "A" overhang in a prepared library fragment (FIG. 2C). In certain embodiments the resulting ligation domain is a single base pair thymine (T) overhang on the 3' end of the extended extension strand, but in other embodiments, it can be a blunt end, or a different type or 3' or 5' overhang "sticky" end. In this particular example "CUT" implies use of a sequence-specific endonuclease, such as a restriction enzyme, to cleave in a way that inherently creates the ligateable end. In other embodiments, after cleavage, further enzymatic or chemical processing, such as with a terminal transferase, can create the ligateable end.

Figure 3:
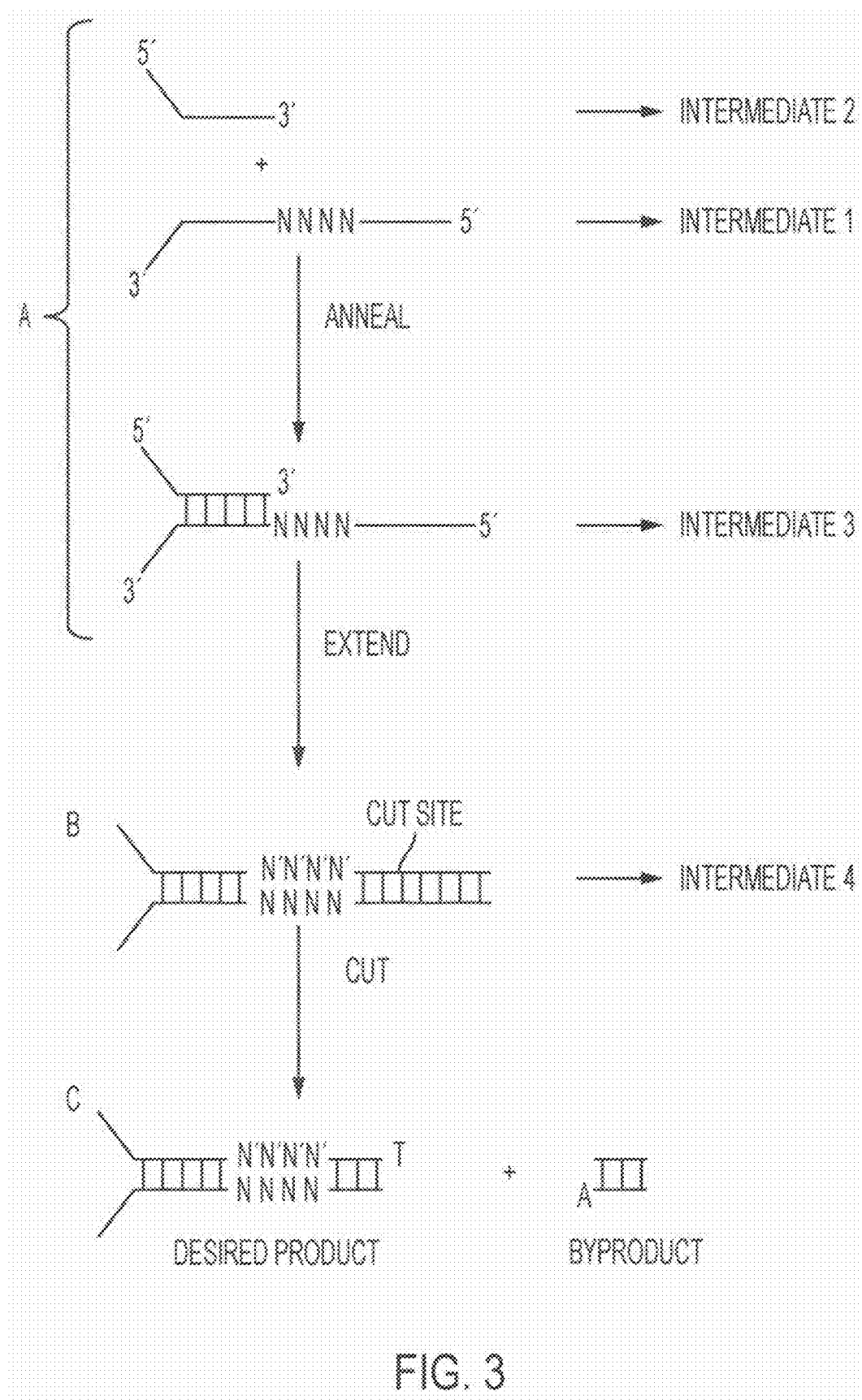
FIG. 3 depicts incomplete intermediates of adapter synthesis at each step of synthesis. Panel A illustrates annealing of the elongation strand and template strand during one form of EE adapter synthesis. Residual template strands and residual elongation strands not annealed during this step (Intermediates 1 and 2, respectively) can remain in the reaction mixture. After annealing, the elongation strands and template strands form pre-adapter complexes which must be enzymatically extended to create a double-stranded adapter sequence. Subsequently, residual non-extended, or incompletely extended, pre-adapter complexes (Intermediate 3) can be also be left over in the reaction mixture after the extension step. Another source of incomplete intermediates during adapter synthesis occurs when a double-stranded 3' region cut-site is either not cut, or is incompletely cut, resulting in residual uncut adapter complexes (Intermediate 4), as illustrated in Panel B. Panel C illustrates a final processing step of adapter synthesis, which also produces an undesirable reaction byproduct, a cleaved fragment, along with a desired adapter product.

In addition to the final desired adapter product, other incomplete products can remain in in the reaction. For example, excess single-stranded oligonucleotides (e.g. elongation strand and template strand), un-extended or incompletely extended pre-adapter complex, un-cut adapter complex, and cleaved fragment intermediates and byproducts are impurities that can decrease adapter ligation efficiency. FIG. 3 is a scheme that illustrates the formation of such intermediates and byproducts during the adapter synthesis process. Referring to FIG. 3A, residual single-stranded template strand and elongation strand that are not hybridized or in complex can form "Intermediate 1 and 2" products, respectively. Further referring to FIG. 3A, residual un-extended, or incompletely extended, pre-adapter complex can form "Intermediate 3" products that remain in solution. Further processing of double-stranded pre-adapter products include cutting a 3' end of the complex to generate a ligateable end (e.g., within a ligation domain). Referring to FIG. 3B, uncut double stranded pre-adapter complexes can form "Intermediate 4" products that remain in solution. Even when successfully cut, a cleaved fragment ("Byproduct") is generated along with the desired duplex adapter.

The intermediate and byproducts can serve to simply contaminate the larger adapter pools being generated potentially reducing adapter efficiency and overall performance.

Figure 4:
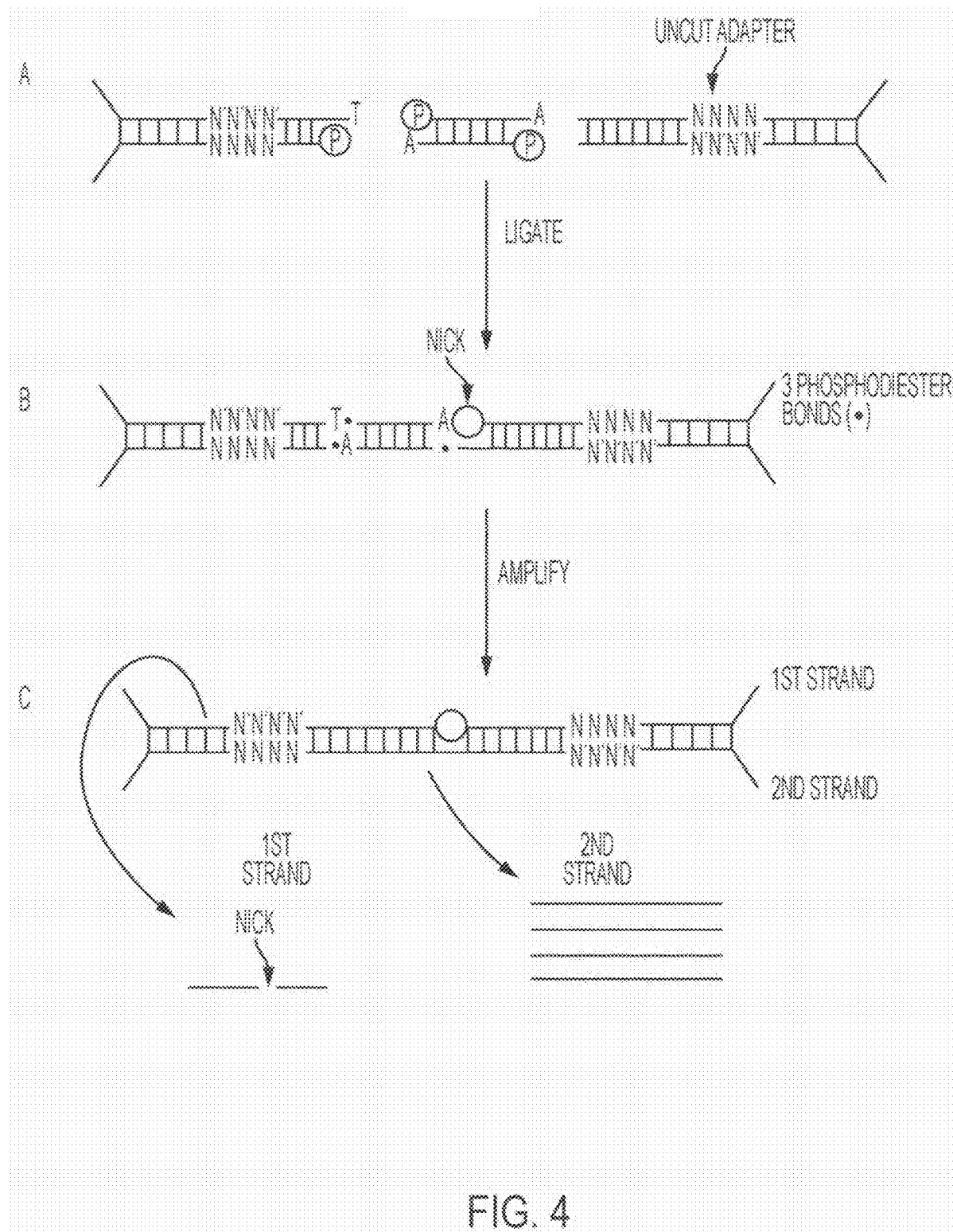
FIG. 4 depicts an example of incomplete intermediates of adapter synthesis leading to aberrant Duplex Sequencing results. Panel A illustrates a library DNA fragment with 3' A-overhangs on each terminus (center) flanked by a fully processed adapter (left) and an uncut adapter (right). Panel B illustrates the ligation of both adapters to the library DNA fragment, wherein ligation of the uncut adapter (right) leaves an open nick on a $1^{st}$ strand of the library DNA fragment. Panel C illustrates asymmetric PCR amplification resulting from the open nick where only the $2^{nd}$ strand is amplified.

Beyond simply decreasing the availability of correct, fully-formed adapter products, some incomplete intermediates and byproducts may be actively harmful to various steps of the Duplex Sequencing process. For example, and as illustrated in FIG. 4, an un-cut adapter complex intermediate with a 3' overhanging "A" from the terminal transferase activity of the polymerase can be forced to ligate to an A-tailed library fragment under certain conditions. Because the 5' end of the un-cut bottom strand is not typically phosphorylated, it cannot ligate whereas the top strand can. Ligation of such an adapter to one end of a library fragment will create a product where only three of the four intended phosphodiester bonds have formed (FIG. 4B). FIG. 4C illustrates that PCR amplification of this product will only make sequenceable copies of one strand and Duplex Sequencing is no longer possible in this scenario.

A variety of optimizations can be undertaken to improve the completeness of the synthesis reaction, but not all incomplete byproducts can be avoided. Purification of complete EE adapter products may improve Duplex Sequencing efficiency, but they can be difficult to manufacture based solely on the differing molecular size properties of the complete versus incomplete products. However, and in accordance with various aspects of the present technology, certain modifications to the oligonucleotides used for the synthesis can significantly alter the chemical properties of the complete versus incomplete adapter products and facilitate the purification.

A. Various Embodiments of Methods and Reagents for Solution-Phase Adapter Synthesis The present disclosure, among other things, provides methods and reagents for solution-phase adapter synthesis. In some embodiments including such methods, one or more capture labels may be used for enrichment/selection of desired adapter product(s) from crude synthesis products, for example, via positive enrichment/selection of desired products or negative enrichment/selection to exclude or reduce the abundance of non-desired products/by-products/side-products.

For example, in some embodiments including positive enrichment, an adapter oligonucleotide can have a capture label that is or comprises an affixed chemical moiety (e.g. biotin) that may be used to purify desired adapter product(s) via capture in one or more subsequent purification steps, for example, via an extraction moiety (e.g. streptavidin) bound to a functionalized surface. In some embodiments including negative enrichment, a capture label that is or comprises an affixed chemical moiety (e.g. biotin) may be used to purify out or separate undesired byproducts of a reaction (e.g., cleaved byproducts bound to a capture label post cutting of pre-adapter product, pre-adapter intermediates, unannealed strands, etc.) via capture in one or more subsequent purification steps, for example, via an extraction moiety (e.g. streptavidin) bound to a functionalized surface.

Single Capture Agent Example

Figure 5:
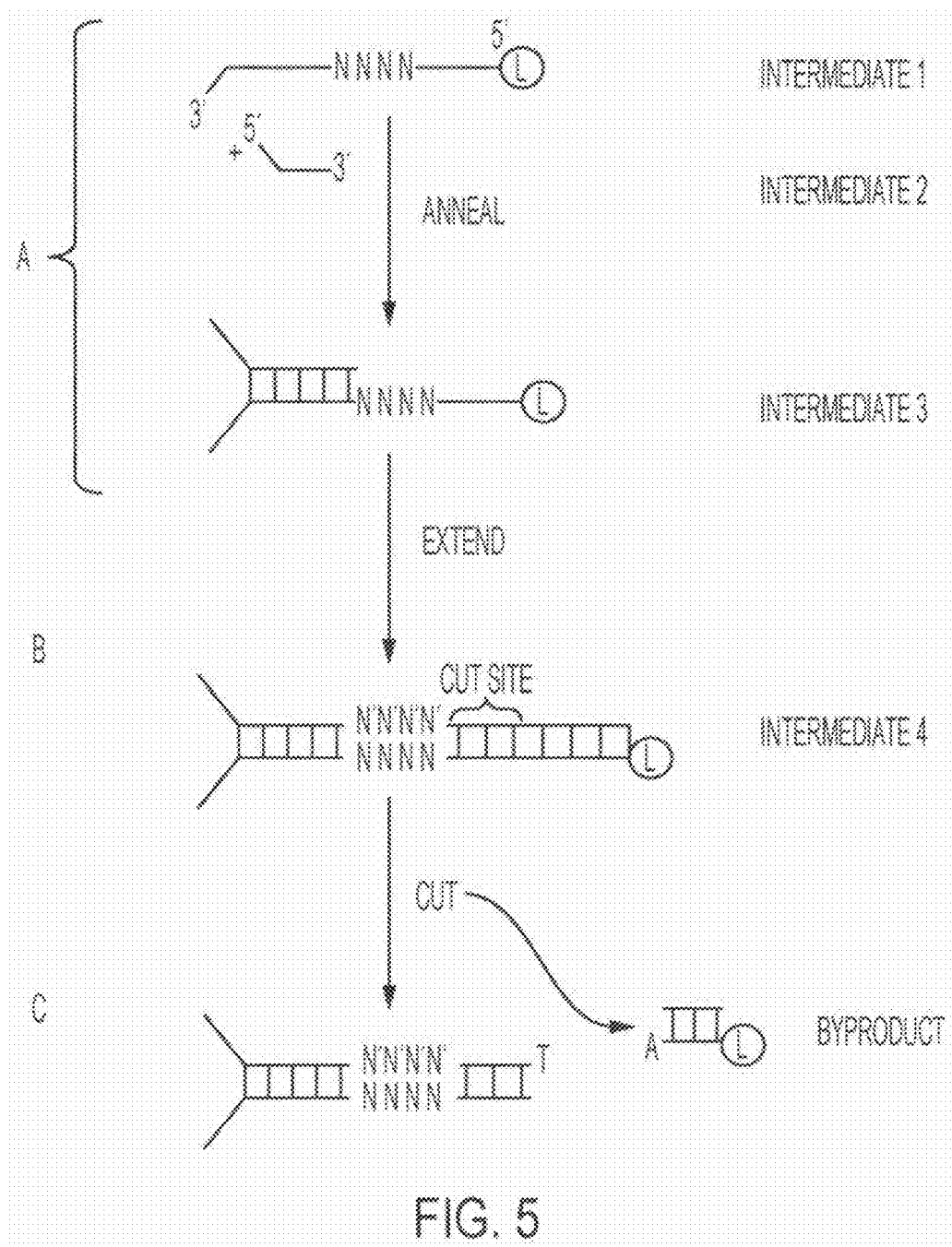
FIG. 5 depicts an embodiment of a method for a solution-phase adapter synthesis scheme using a capture label. Panel A illustrates annealing of a template strand and an elongation strand at an at least partially complementary region to form a pre-adapter complex, wherein the template strand comprises a 5' capture label. Incomplete intermediates during this step include excess template strands and elongation strands (Intermediates 1 and 2, respectively). Enzymatic extension of the elongation strand of the pre-adapter complex produces an uncut adapter complex comprising a double-stranded sequence having a SMI in both strands. Subsequent incomplete intermediates during this step include non-extended, or incompletely extended, pre-adapter complexes (Intermediate 3). During the next step, a double-stranded 3' region (e.g., a ligation domain) cut-site is cut by treatment with, e.g., a restriction endonuclease enzyme thereby producing the desired adapter product and a cleaved fragment byproduct. Panel B illustrates uncut adapter complex that either failed to be cut, or was cut incompletely by treatment with enzyme (Intermediate 4). Panel C illustrates the desired adapter product and the cleavage fragment byproduct. Notably, the cleavage fragment byproduct retains the 5' capture label after cutting the 3' region cut-site. Panel D illustrates the negative selection process of adapter purification involving the addition of a functionalized surface that is capable of binding the capture label to the reaction mixture. The functionalized surface binds only to intermediates and byproducts that comprise capture label, including Intermediates 1, 3 and 4, and the byproducts. The unlabeled desired adapter product having a duplex SMI is purified by removal of the functionalized surface and bound intermediates/byproducts.
Figure 5:
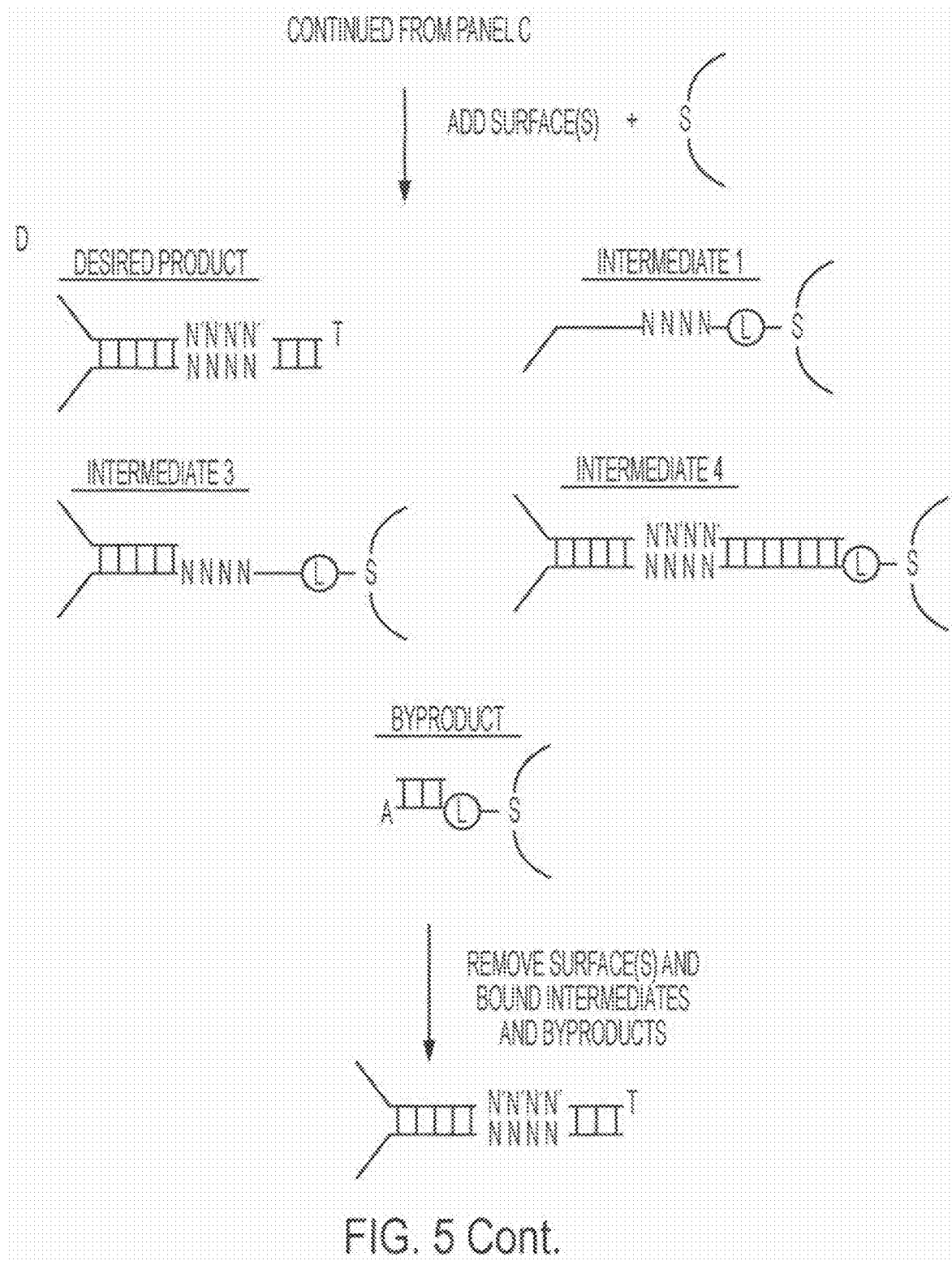

FIG. 5 illustrates an embodiment including negative enrichment/selection and the use of a single capture agent and Y-shaped adapters. Specifically, in FIG. 5, panel A an elongation strand and a template strand are annealed at an at least partially complementary region in a reaction mixture to create a pre-adapter complex. In some embodiments, the template strand and the elongation strand are synthesized oligonucleotides. In a particular embodiment, the elongation strand can include a pre-defined or known oligonucleotide sequence. In certain embodiments, the template strand can include portions of pre-defined sequence and include a region of random or semi-random nucleotide sequence (e.g., a degenerate or semi-degenerate sequence). Accordingly, such portions of sequence can be an identifier sequence or SMI. The template strand can also incorporate a capture label, such as at a 5' end in this example. In a particular example, a template strand can be synthesized (e.g., on controlled pore glass (CPG) fragments or the like) in a 3' to 5' direction such as via the phosphoramidite method, and a chemical moiety can be linked (e.g., covalently linked, non-covalently linked, ionically linked or other linking chemistry) to the 5' terminus following synthesis of the oligonucleotide, or as part of the synthesis of the oligonucleotide, such as via incorporation of a non-canonical phosphoramidite molecule at the 5' terminus, near the 5' terminus or at an internal position in the oligonucleotide. In the embodiment illustrated in FIG. 5, the template strand includes a SMI in a mid or central region of the sequence. Also shown, the template strand includes a capture label at the 5' end of the strand (e.g., biotin). In some embodiments, a cut site, such as a template sequence for generating a double-stranded restriction endonuclease recognition site, is included between the SMI and a capture label. Such a double-stranded restriction endonuclease recognition site can be enzymatically cut with the corresponding restriction endonuclease so as to separate the capture label from an adapter complex as described in more detail below. Further, cutting at the cut site can provide the adapter complex with a 3' ligateable end (e.g., a ligation domain). Similarly, a pair of single-stranded nuclease (i.e. a "nickase") recognition sites can serve a similar functional purpose for cleaving the backbone sequence of the double-stranded DNA strands.

The enzymes used for such cleavage events can include restriction endonucleases, such as type I restriction endonucleases or type II restriction endonucleases or other restriction endonucleases, including nickases or any modified endonuclease that has been modified chemically or via genetic engineering of the structure from the derivative organism. The endonuclease site of cleavage may be recognized by the sequence nature of the polynucleotide (i.e. the recognition motif) or the endonuclease could be one that recognizes and cleaves modified or non-canonical nucleotides or components of the sugar-phosphate backbone, directly or indirectly. The endonuclease can involve systems that are specific to long recognition sites such as TALENs, Meganucleases/homing endonucleases, MegaTALENs, zinc-finger nucleases or the alike. The endonuclease can be an easily customizable system involving a guide RNA sequence such as CRISPER/Cas9 or CPF1 or similar. The recognition site can include both a complementary region of a guide RNA and a PAM motif. It will be recognized by one experienced in the art that a large number of similar enzymes or enzymatic systems for directly or indirectly cleaving the backbone could be applied to a similar purpose. It will also be apparent that combinations of enzymes, ribozymes or other targeted molecular cleavage catalysts could be combined with, or entirely substituted for other chemical methods of cleavage, such as photocleavable linkers or the alike.

Optionally, the elongation strand includes a region of non-complementarity with respect to the template strand that can function as an SDE during Duplex Sequencing analysis. Optionally, the template strand contains a region of non-complementarity with respect to the elongation strand that can function as an SDE during Duplex Sequencing analysis. The region(s) of non-complementarity can include, in some embodiments, a primer binding site, a read primer sequence, an SMI, an index sequence or other tag sequence, modified or non-nucleotide molecules, and/or one or more cut sites.

Annealing of the elongation and the template strands can be carried out in the presence of excess template strand and/or excess elongation strand, or using equimolar amounts of both template strand and elongation strand. In some embodiments, it is appreciated that some amount residual elongation strand and/or template strand may remain unannealed in the reaction mixture. Residual template strand is referred to as Intermediate 1 and residual elongation strand is referred to as Intermediate 2 in FIG. 5, panel A. In the present embodiment, utilizing solution-phase adapter synthesis, a molar ratio of excess template strand to elongation strand can ensure that the reaction mixture comprises all or mostly template strand, and that free/unhybridized template strand (Intermediate 1) may be removed, for example, via negative enrichment/selection as described herein.

Upon annealing of the elongation strand and the template strand to create a pre-adapter complex (FIG. 5, panel A), the elongation strand is enzymatically extended from the 3' end to produce an elongated double-stranded portion of the pre-adapter complex (FIG. 5, panel B). The double-stranded portion includes a duplex SMI (e.g., an SMI sequence in both strands) and a double-stranded cut site (e.g., a restriction endonuclease recognition site), thereby creating a double-stranded uncut adapter complex (see FIG. 5, panel B). In some embodiments, it is appreciated that some of the pre-adapter complexes may fail to be extended during this step, or be incompletely extended, and remain in the reaction mixture. These residual pre-adapter complex(es) are referred to as Intermediate 3 in FIG. 5, panel A, and these undesired entities may be removed, for example, via negative enrichment/selection as described herein.

Next, as shown in FIG. 5, panel C, the double-stranded uncut adapter complex is treated with an appropriate enzyme to interact with the pre-adapter complex at the cut site. For example, a restriction endonuclease enzyme that cuts a restriction endonuclease recognition cut site (e.g., within a ligation domain 3' to the SMI) to produce a 3' ligateable end on the desired adapter product can be provided to the reaction mixture. In FIG. 5, panel C, the ligateable end is shown as a T-overhang, however, it will be apparent to one of skill in the art that the ligateable end can be any of a variety of forms, for example, a blunt end, an A-3' overhang, a "sticky" end comprising a one nucleotide 3' overhang, a two nucleotide 3' overhang, a three nucleotide 3' overhang, a 4, 5, 6, 7, 8, 9, 10, 11, 12, 13, 14, 15, 16, 17, 18, 19, 20 or more nucleotide 3' overhang, a one nucleotide 5' overhang, a two nucleotide 5' overhang, a three nucleotide 5' overhang, a 4, 5, 6, 7, 8, 9, 10, 11, 12, 13, 14, 15, 16, 17, 18, 19, 20 or more nucleotide 5' overhang, among others. The 5' base of the ligation site can be phosphorylated and the 3' base can have a hydroxyl group, or either can be, alone or in combination, dephosphorylated or dehydrated or further chemically modified to either facilitate enhanced ligation or one strand to prevent ligation of one strand, optionally, until a later time point. The cutting of the ligation domain also produces a cleaved fragment, referred to as the byproduct in FIG. 5, panel C. The melting temperature of this by product may be low and the cleaved fragment may melt apart under certain temperature and salt conditions, or may remain annealed under certain temperature and salt conditions. In this way, the desired adapter product is separated from (e.g., released from) the capture label. Said another way, as the cleaved fragment contains the affixed capture label, the desired adapter product no longer includes a capture label after the cutting step.

In some embodiments, it is appreciated that some of the pre-adapter complexes may fail to be cut during this step and remain in the reaction mixture. These residual uncut pre-adapter complex(es) are referred to as Intermediate 4 in FIG. 5, panel B, and these undesired entities may be removed, for example, via negative enrichment/selection as described herein.

Post cutting, as is shown in FIG. 5, panel D, the reaction mixture is brought into contact with a functionalized surface with one or more extraction moieties bound thereto. The provided extraction moieties are capable of binding to the capture label (e.g. a streptavidin bead where the capture label is biotin) for immobilization and separation of molecules bearing the capture label. In particular, the extraction moiety can be any member of a binding pair, such as biotin/streptavidin or hapten/antibody or complementary nucleic acid sequences (DNA/DNA pair, DNA/RNA pair, RNA/RNA pair, LNA/DNA pair, etc.). In the illustrated embodiment, a capture label that is attached to intermediate products and byproducts of the adapter manufacturing process is captured by its binding pair (e.g., the extraction moiety) which is attached to an isolatable moiety (e.g., such as a magnetically attractable particle or a large particle that can be sedimented through centrifugation). Accordingly, the capture label can be any type of molecule/moiety that allows affinity separation of nucleic acids bearing the capture label from nucleic acids lacking the capture label. An example of a capture label is biotin which allows affinity separation by binding to streptavidin linked or linkable to a solid phase or an oligonucleotide, which in turn allows affinity separation through binding to a complementary oligonucleotide linked or linkable to a solid phase.

As illustrated in FIG. 5, panel D, undesired intermediates (e.g., Intermediate 1, Intermediate 3, Intermediate 4) and byproducts containing the capture label are bound by the functionalized surface and the desired adapter product is left free in solution. In accordance with various embodiments, undesired intermediates and byproducts may be or comprise any or all of: cleaved fragments, excess template strands, non-extended or incompletely extended pre-adapter complexes, and/or uncut or only partially cut adapter complexes and can also include constituent oligonucleotides that were incompletely or improperly chemically synthesized prior to ligation, such as incomplete length products, products with damaged nucleotides, products with insertions or deletions relative to the desired synthesis sequence, products that have erroneously been ligated or cross-linked to other products or other chemical moieties such as enzymes or other types of molecules or surfaces, products with undesired nucleotide adducts, those with damage such as oxidation, deamination, phosphorylation, dephosphorylation, sumoylation, glycosylation, deglycosylation, putrescinylation, carboxylation, halogenation, formylation, hydrolysis damage, nuclease damage, photodamage such as pyrimidine dimers, or with any other form of incomplete or erroneous synthesis or damage thereafter, or any by products, intermediate products, side products, such as those enumerated above, which contain one or more such oligonucleotides with incomplete or erroneous synthesis or damage to them thereafter. Similarly, undesired products containing errors (such as mismatches, insertions or deletions) introduced by polymerase extension, misincorporated natural or damaged nucleotides or as a consequence of unintended terminal transferase activity or exonuclease activity, can all entail undesired products and contribute to non-extended or incompletely extended pre-adapter complexes, and/or uncut or only partially cut adapter complexes.

In some embodiments, provided methods allow for removal of all or substantially all undesired intermediates and or byproducts or substantially reduce their abundance. Collection of the desired adapter product(s) may be accomplished in any application-appropriate manner. By way of specific example, in some embodiments, collection of desired adapter product(s) may be accomplished via one or more of removal of the functionalized surface via size filtration, magnetic methods, electrical charge methods, centrifugation density methods or any other methods or, collection of elution fractions if using column-based purification methods or similar, or by any other commonly understood purification practice.

Multiple Capture Agent Example

In some embodiments, a method may include the use of two or more capture labels (e.g., 2, 3, 4, 5, 6, 7, 8, 9, 10 or more). In some embodiments, at least two capture labels used in a method are different from one another (e.g., a small molecule and a peptide). In some embodiments, inclusion of two or more different capture labels allows for the use of both positive enrichment/selection as well as negative enrichment/selection. Inclusion of two or more capture labels can be helpful, inter alia, in cases where there is a desire to control for instances when a capture label is unintentionally unincorporated into the original oligo synthesis of the template strand and/or where there is concern that non-labelled molecules (e.g., elongation strand) may pass through to the final collected adapter product.

Figure 6:
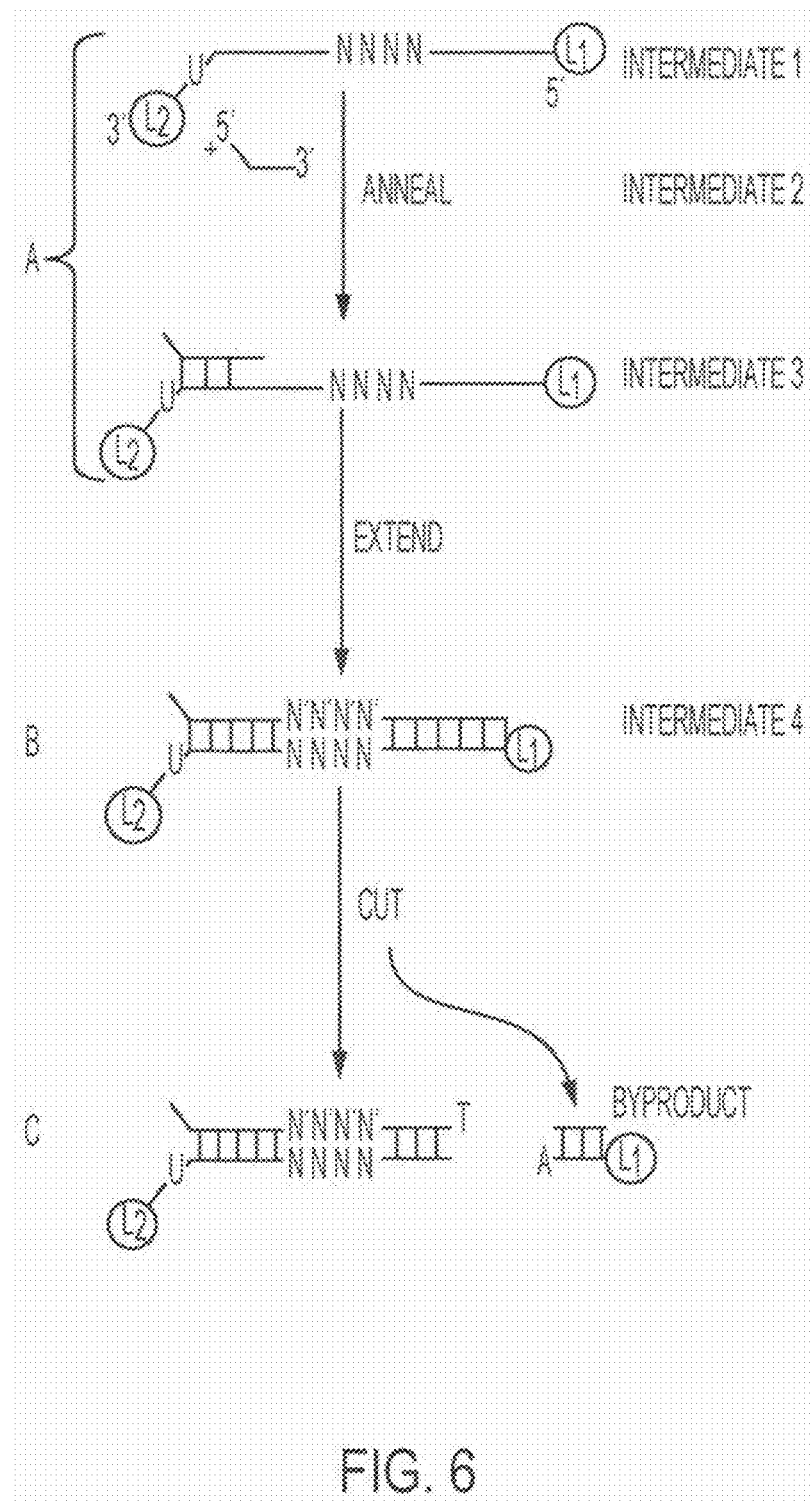
FIG. 6 depicts an embodiment of a method for a solution-phase adapter synthesis scheme using two-capture labels. Panel A illustrates annealing of a template strand and an elongation strand at an at least partially complementary region to form a pre-adapter complex, wherein the template strand comprises a 3' cleavable capture label and a 5' capture label. Incomplete intermediates during this step include excess template strands and elongation strands (Intermediates 1 and 2, respectively). Enzymatic extension of the elongation strand of the pre-adapter complex produces an uncut adapter complex comprising a double-stranded sequence having a SMI in each strand. Subsequent incomplete intermediates during this processing include non-extended, or incompletely extended, pre-adapter complexes (Intermediate 3). During the next step, the ligation domain cut-site is cut by treatment with, e.g., a restriction endonuclease enzyme thereby producing the desired adapter product and a cleaved fragment byproduct. Panel B illustrates uncut adapter complex that either failed to be cut or was cut incompletely by treatment with enzyme (Intermediate 4). Panel C illustrates the desired adapter product and the cleavage fragment byproduct. Following treatment with the restriction enzyme, the desired adapter product retains the 3' cleavable capture label and the cleavage fragment byproduct retains the 5' capture label. Panel D illustrates negative enrichment/selection and positive enrichment/selection processes of adapter purification involving the step-wise addition of functionalized surfaces that are capable of binding the 5' capture label, or binding the 3' cleavable capture label. During the negative enrichment/selection process, a first functionalized surface binds to intermediates and byproducts bearing the 5' capture label, including Intermediates 1, 3 and 4, and the byproducts. The adapter complex comprising a 3' cleavable affinity label is initially purified by separation of the first functionalized surface with bound intermediates/byproducts from the remaining reaction mixture. During the positive enrichment/selection process, a second functionalized surface is introduced to the reaction mixture and binds to the adapter complex via the 3' cleavable capture label. Following a wash step or the like, the adapter-bound functionalized surface is then enzymatically treated to cut the cleavable 3' capture label thereby releasing the desired adapter product in solution. The desired adapter product having a duplex SMI is then purified by separation from the second functionalized surface.
Figure 6:
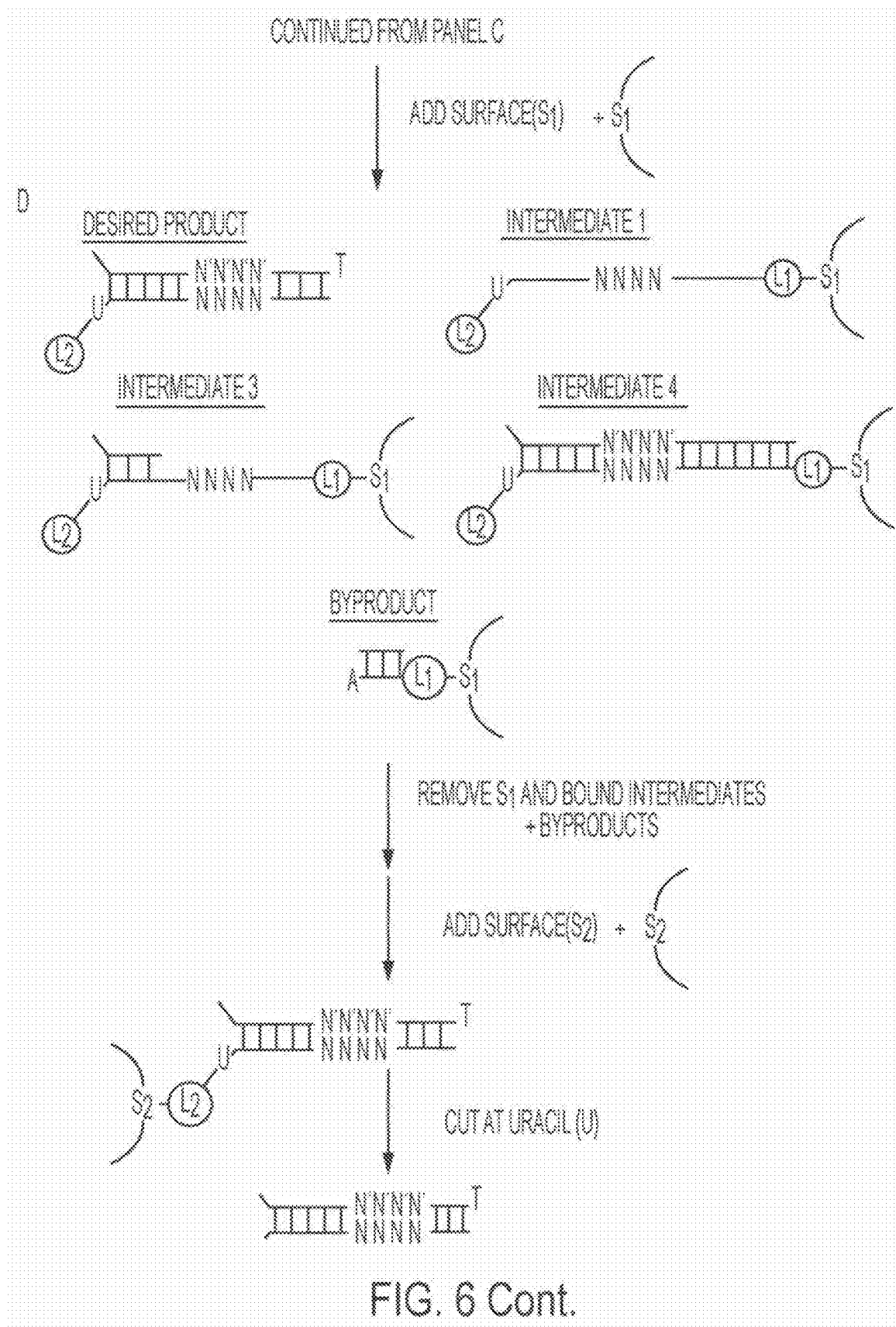

In instances where additional purification of a desired adapter product is appropriate, a negative enrichment scheme can be combined with a positive enrichment scheme by using a double-affinity tag method, for example, as exemplified in FIG. 6. Particular to methods including two or more-capture agents, a template strand may also include a capture label at a 3' end of the strand along with the capture label at the 5' end as is shown in FIG. 6. The capture label at the 3' end of the template strand may be linked to the template strand via an optional cleavable moiety. A cleavable moiety can be a uracil group, as shown in FIG. 6, or any other enzymatically, chemically or photo-electrically cleavable group.

As is shown in FIG. 6, panel A, and similar to some embodiments including a single capture label (see FIG. 5), an elongation strand and a template strand are annealed at an at least partially complementary region in a reaction mixture to create a pre-adapter complex. The elongation strand and/or the template strand may have regions of non-complementarity that, as discussed above, can include primer binding site(s), a read primer sequence, an SMI, an index sequence or other tag sequence, modified or non-nucleotide molecules, and/or one or more cut sites. In some embodiments, the region of non-complementarity can function as an SDE.

In the embodiment illustrated in FIG. 6, the template strand includes a SMI in a mid or central region of the sequence. Also shown, the template strand includes a first capture label at the 5' end of the strand (e.g., biotin) and a second capture label, which can be the same or different from the first capture label, at a 3' end of the strand. In some embodiments, first a cut site, such as a template sequence for generating a double-stranded restriction endonuclease recognition site, is included between the SMI and the first capture label. Additionally, a second cut site, such as a modified nucleotide or a non-nucleotide molecule, is positioned 5' to the second capture label via a cleavable linkage such that the second capture label is a cleavable capture label. In some embodiments, the cleavable linkage is a photocleavable linkage. In some embodiments, the cleavable linkage comprises a uracil nucleotide. In another embodiment, the second capture labels comprise biotin linked to nucleic acid strands including one or more modified residues. In one embodiment, a modified nucleotide can comprise a ribose nucleotide. In yet another embodiment, the second cut site can be a photocleavable desthiobiotin-TEG or uracil residue cleavable with a combination of uracil DNA glycosylase (UDG) and an enzyme with abasic site DNA lyase activity such as endonuclease VIII or formamidopyrimidine [fapy]-DNA glycosylase (FPG) or commercial premixed combinations (for example USER™ enzyme. In certain embodiments, the one or more modified nucleotide or non-nucleotide molecule may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine.

As with the embodiments including a single capture label (see FIG. 5), annealing of an elongation and a template strand can be carried out in the presence of excess template strand and/or excess elongation strand, or using equimolar amounts of both template strand and elongation strand. In the present embodiment, utilizing solution-phase adapter synthesis with both negative enrichment/selection and positive enrichment/selection steps, excess template strand (Intermediate 1) and excess elongation strand (Intermediate 2) can be removed during processing. Free/unhybridized template strand (Intermediate 1) may be removed, for example, via negative enrichment/selection and free/unhybridized elongation strand (Intermediate 2) may be removed, for example, via positive enrichment/selection as described herein.

FIG. 6, panel B shows that the pre-adapter complex may be enzymatically extended, and FIG. 6, panel C shows that un-cut adapter complex is treated enzymatically (e.g., with a restriction endonuclease enzyme) to cut at the cut-site. AS shown in FIG. 6, panel C, the cutting step produces both cut adapter complexes having a second capture label 3' to the double-stranded region comprising the SMI and, optionally, linked to the 3' end of the template strand via a cleavable linker, and cleaved fragments including the first capture label. As indicated in FIG. 6 panels A-C, Intermediates 1, 3 and 4, and cleavage fragment byproducts are also formed during this process substantially as described for some single capture agent embodiments as described in FIG. 5.

A step of negative enrichment/selection may be performed next, for example, via introduction of the reaction mixture to a functionalized surface ($S_1$) that is capable of binding the 5'-positioned first capture label (and, in the illustrated embodiment, not the 3'-positioned second capture label) (FIG. 6, panel D). Binding interaction between the first capture label and the functionalized surface ($S_1$) through an associated extraction moiety/binding partner will immobilize undesired intermediates and byproducts that include the 5'-positioned first capture label, while the desired adapter product with the 3'-positioned second capture label will remain free in solution (FIG. 6, panel D). The removal of the functionalized surface ($S_1$) provides a first step of adapter purification.

In a positive enrichment/selection step, a functionalized surface ($S_2$) capable of binding the 3'-positioned second capture label is introduced to the reaction mixture. Binding interaction between the second capture label and the functionalized surface ($S_2$) through an associated extraction moiety/binding partner will immobilize desired adapter products. Once desired adapter products are immobilized, the reaction mixture can be washed, and/or the immobilized adapter products can be separated from the remaining reaction mixture. Beneficially, free/unhybridized elongation strand (Intermediate 2), which does not bear any capture label, can be effectively removed/separated from the desired adapter product. In further embodiments, the functionalized surface ($S_2$) maybe washed to remove residual intermediates, byproducts, or other contaminants. In further steps, the reaction mixture comprising the functionalized surface ($S_2$) with bound adapter products may be treated with a reagent (e.g., an enzyme) that cleaves and separates the 3'-positioned (cleavable) capture label from the desired adapter product, thereby freeing the desired adapter product into solution. For example, a reaction mixture comprising the functionalized surface ($S_2$) can be treated with USER (Uracil-Specific Excision Reagent) enzyme (a commercial combination of UDG and Endonuclease VIII), or any other treatment that can cleave at an incorporated linker group (for example, a uracil group as shown in FIG. 6 or RNAseH2 that cleaves sugar phosphate backbone at ribose bases). The desired adapter product may then be collected as eluate, or separated by removing the (secondary) functionalized surface ($S_2$).

While embodiments comprising a first capture label and a second (cleavable) capture label that is different from the first capture label are described with reference to FIG. 6, it will be understood by those of skill in the art that the first capture label and second capture label can be the same capture label. In such instances, introduction of a functionalized surface bearing an extraction moiety that is the binding partner for the first and second capture labels can be introduced following the cutting step. The first and second capture labels will be immobilized via interaction between the capture labels and the functionalized surface(s) (not shown). Following immobilization, the first cut site can be targeted (e.g., via restriction enzyme) such that double-stranded pre-adapter molecules can be cut and released from first capture label immobilization. At this stage, undesired intermediate and byproducts remain bound to the functionalized surface. Additionally, at this stage, desired adapter products remain bound to the functionalized surface via the second capture label. Unbound or free molecules not bearing the first or second capture labels can be removed or otherwise separated from those bearing the capture labels. In a next step, a cleavable linker proximate to or 5' to the second capture label can be targeted for cleavage to initiate release of the desired adapter product into solution. Removal and/or separation of the functionalized surface from the unbound desired product in solution provides a purified adapter product both negatively enriched/selected (removal of undesired intermediates and byproducts) and positively enriched/selected.

As with some embodiments including a single capture agent, some embodiments including two or more capture agents allow for the removal of undesired intermediates and byproducts that may be or comprise any or all of: cleaved fragments, excess template strands, excess elongation strands, non-extended or incompletely extended pre-adapter complexes, and/or uncut or only partially cut adapter complexes or others enumerated above. In some embodiments, provided methods allow for removal of all or substantially all undesired intermediates and or byproducts to provide a purified duplex adapter product.

Additional Aspects

Adapter Types

While the majority of examples in the present disclosure depict Y shaped or loop adapters, any known adapter structure may be used in accordance with various embodiments, such as those described in WO2017/100441, which is incorporated herein by reference in its entirety. For example, various adapter shapes comprising bubbles (e.g., internal regions of non-complementarity) are further contemplated.

Separation

As is described herein, various methods include at least one separation step. It is specifically contemplated that any of a variety of separation steps may be included in various embodiments. For example, in some embodiments, separation may be or comprise physical separation, size separation, magnetic separation, solubility separation, charge separation, hydrophobicity separation, polarity separation, electrophoretic mobility separation, density separation, chemical elution separation, SBIR bead separation etc. For example, a physical group can have a magnetic property, a charge property, or an insolubility property. In embodiments, when the physical group has a magnetic property and a magnetic field is applied, the associated adapter nucleic acid sequences including the physical group is separated from the adapter nucleic acid sequences not including the physical group. In another embodiment, when the physical group has a charge property and an electric field is applied, the associated adapter nucleic acid sequences including the physical group is separated from the adapter nucleic acid sequence not including the physical group. In embodiments, when the physical group has an insolubility property and the adapter nucleic acid sequences are contained in a solution for which the physical group is insoluble, the adapter nucleic acid sequences comprising the physical group is precipitated away from the adapter nucleic acid sequence not including, the physical group which remains in solution.

Any of a variety of physical separation methods may be included in various embodiments. By way of specific example, a non-limiting set of methods includes: size selective filtration, density centrifugation, HPLC separation, gel filtration separation, picking out each bead with itsy bitsy tweezers one by one, FPLC separation, density gradient centrifugation and gel chromatography, among others.

Any of a variety of magnetic separation methods may be included in various embodiments. Typically, magnetic separation methods will encompass the inclusion or addition of one or more physical groups having a magnetic property such that, when a magnetic field is applied, molecules including such physical group(s) are separated from those that do not. By way of specific example, physical groups that include exhibit a magnetic property include, but are not limited to ferromagnetic materials such as iron, nickel, cobalt, dysprosium, gadolinium and alloys thereof. Commonly used paramagnetic beads for chemical and biochemical separation embed such materials within a surface that reduces chemical interaction of the materials with the chemicals being manipulated, such as polystyrene, which can be functionalized for the affinity properties discussed above.

Extension

With regard to extension, for example, of an elongation strand, any known method may be used. In some embodiments where one or more enzymes are used, such enzyme(s) may be selected from DNA polymerases with varying degrees of strand-displacement activity that extend nucleic acid sequences from a 3'OH group in a 5' to 3' direction. Examples of DNA polymerases include T4, T7, phi29, Bst DNA Polymerase, Taq polymerase, Pol I polymerase, and many others. In general, polymerases lacking strand displacement activity can be used in such gap-filling reactions described further herein. Non-limiting examples of commercially available non-strand-displacing polymerases include T4 and T7 DNA polymerases.

Capture Labels

As is described herein, in some embodiments, a capture label may be present in any of a variety of configurations along a template strand. For example, in some embodiments, a capture label may be present on the 5' ends, the 3' ends, or both ends of a template strand. In other embodiments, a capture label can be incorporated or affixed to a template strand in a region 5' of the identifier sequence. In some embodiments, a capture label may be present somewhere in the middle of a template strand (i.e., not on the 5' or 3' end of the template strand). In embodiments including two or more capture labels, each capture label may be present at a different location along the template strand.

In some embodiments, a capture label is selected from a group of biotin, biotin deoxythymidine dT, biotin NHS, biotin TEG, Biotin-6-Aminoaliyl-2'-deoxyuridine-S'-Triphosphate, Biotin-16-Aminoallyl-2-deoxycytidine-5'-Triphosphate, Biotin16-Aminoallylcytidine-5'-Triphosphate, N4-Biotin-OBEA-2'-deoxycytidine-5'-Triphosphate, Biotin-16-Aminoallyluridine-5'-Triphosphate, Biotin-16-7-Deaza-7-Aminoallyl-2'-deoxyguanosine-5'-Triphosphate, 5'-Biotin-G-Monophosphate, 5'-Biotin-A-Monophosphate, 5'-Biotin-dG-Monophosphate, 5'-Biotin-dA-Monophosphate, desthiobiotin NHS, Desthiobiotin-6-Aminoallyl-2'-deoxycytidine-5'-Triphosphate, digoxigenin NHS, DNP TEG, thiols, Colicin E2, Im2, glutathione, glutathione-s-transferase (GST), nickel, polyhistidine, FLAG-tag, myc-tag, among others. In some embodiments, capture labels include, without limitation, biotin, avidin, streptavidin, a hapten recognized by an antibody, a particular nucleic acid sequence and/or magnetically attractable particle. In some embodiments, one or more chemical modifications of nucleic acid molecules (e.g., Acridite™-modified among many other modifications, some of which are described elsewhere in the application) can serve as a capture label.

Extraction Moieties

Extraction moieties can be a physical binding partner or pair to targeted capture label and refers to an isolatable moiety or any type of molecule that allows affinity separation of nucleic acids bearing the capture label from nucleic acids lacking the capture label. Extraction moieties can be directly linked or indirectly linked (e.g., via nucleic acid, via antibody, via aptamer, etc.) to a substrate, such as a solid surface. In some embodiments, the extraction moiety is selected from a group comprising a small molecule, a nucleic acid, a peptide, an antibody or any uniquely bindable moiety. The extraction moiety can be linked or linkable to a solid phase or other surface for forming a functionalized surface. In some embodiments, the extraction moiety is a sequence of nucleotides linked to a surface (e.g., a solid surface, bead, magnetic particle, etc.). In some embodiments, wherein the capture label is biotin, the extraction moiety is selected from a group of avidin or streptavidin. It will be appreciated by one of skill in the art, any of a variety of affinity binding pairs may be used in accordance with various embodiments.

In certain embodiments, extraction moieties can be physical or chemical properties that interact with the targeted capture label. For example, an extraction moiety can be a magnetic field, a charge field or a liquid solution in which a targeted capture label is insoluble. Such physical or chemical properties can be applied and adapter nucleic acids bearing the capture label can be immobilized within/against a vessel (surface) or column. Depending on the desired negative enrichment/selection or positive enrichment/selection outcome, the non-immobilized molecules can be retained (negative enrichment) or the immobilized molecules can be retained (positive enrichment) for further purification/processing or use.

Solid Surfaces

When the affinity partner/extraction moiety is attached to a solid surface or substrate and bound to the capture label, the adapter nucleic; acid sequences including the capture label is capable of being separated from the adapter nucleic acid sequence not including the affinity label. A solid surface or substrate may be a bead, isolatable particle, magnetic particle or another fixed structure.

As is described herein and will be appreciated by one of skill in the art, any of a variety of functionalized surfaces may be used in accordance with various embodiments. For example, in some embodiments, a functionalized surface may be or comprise a bead (e.g., a controlled pore glass bead, a macroporous polystyrene bead, etc.). However, it will be understood to one of skill in the art that many other chemical moiety/surface pairs could be similarly used to achieve the same purpose. It will be understood that the specific functionalized surfaces described here are meant only as examples, and that any other appropriate fixed structure or substrate capable of being associated with (e.g., linked to, bound to, etc.) one or more extraction moieties may be used.

Cutting of Nucleic Acids

Various aspects of the present technology, including the synthesizing, making, processing and purification of duplex adapters incorporate enzymatic cleavage, enzymatic cleavage of one strand, enzymatic cleavage of both strands, incorporation of a modified nucleic acid followed by enzymatic treatment that leads to cleavage or one or both strands, incorporation of a photocleavable linker, incorporation of a uracil, incorporation of a ribose base, incorporation of an 8-oxo-guanine adduct, use of a restriction endonuclease, use of site-directed cutting enzymes, and the like. In other embodiments, endonucleases, such as a ribonucleoprotein endonuclease (e.g., a Cas-enzyme, such as Cas9 or CPF1), or other programmable endonuclease (e.g., a homing endonuclease, a zinc-fingered nuclease, a TALEN, a meganuclease (e.g., megaTAL nuclease), an argonaute nuclease, etc.), and any combination thereof can be used.

As is described herein, various embodiments include the use of one or more endonucleases which recognize unique nucleotide sequences or modifications or other entities that recognizes base or other backbone chemical modifications for cutting and/or cleaving a double stranded nucleic acid (e.g., DNA or RNA) at a specific location in one or moth strands. Examples include Uracil (recognized and can be cleaved with a combination of Uracil DNA glycosylase and an abasic site lyase such as Endonuclease VIII or FPG, and ribose nucleotides, which can be recognized and cleaved by RNAseH2 when these are paired with DNA base. The nucleic acid may be DNA, RNA, or a combination thereof, and optionally, including a peptide-nucleic acid (PNA) or a locked nucleic acid (LNA) or other modified nucleic acid. In some embodiments, cutting may be performed via use of one or more restriction endonucleases. In some embodiments, cleaving may be performed using a cleavable linker, for example, uracil desthiobotin-TEG, ribose cleavage, or other methods. In some embodiments the cleavable linked may be a photocleavable linker or a chemical cleavable linker not requiring of enzymes, or partially In some embodiments, for example, when using a restriction endonuclease to cut a double stranded nucleic acid, one or more restriction endonuclease recognition template sequences can be included in a template strand. When the elongation strand is extended, the resultant double-stranded restriction endonuclease recognition sequence is recognizable by its corresponding restriction endonuclease. In some embodiments, a restriction endonuclease recognition template sequence is added prior to initiation of an annealing step. In some embodiments, a restriction endonuclease recognition template sequence is added after one or more extending, cutting or removing steps as described herein. In some embodiments, a restriction endonuclease recognition sequence may be or may be generated 3' of an SMI. In some embodiments, a restriction endonuclease recognition sequence may be or may be generated 5' of an SMI. In some embodiments, a restriction endonuclease recognition sequence may be 3' of an SDE. In some embodiments, a restriction endonuclease recognition sequence may be 5' of an SDE. In some embodiments, a restriction endonuclease recognition sequence may be 3' of a capture label. In some embodiments, a restriction endonuclease recognition sequence may be 5' of a capture label. In some embodiments, a restriction endonuclease recognition sequence may be within or proximal a ligation domain. In some embodiments, a restriction endonuclease recognition sequence may be provided such that subsequent treatment with a corresponding restriction endonuclease generates a 3' ligateable end of the duplex adapter.

In some embodiments, a template strand will include 2 or more (e.g., 3, 4, 5, 6, 7, 8, 9, 10 or more) restriction endonuclease recognition sites. It will be appreciated by one of ordinary skill in the art that a variety of restriction endonucleases (i.e., restriction enzymes) that cleaves DNA at or near recognition sites (e.g., EcoRI, BamHI, XbaI, HindIII, AluI, AvaII, BsaJI, BstNI, DsaV, Fnu4HI, HaeIII, MaeIII, N1aIV, NSiI, MspJI, FspEI, NaeI, Bsu36I, NotI, HinF1, Sau3AI, PvuII, SmaI, HgaI, AluI, EcoRV, etc.) may be in accordance with various embodiments of the present technology. Listings of several restriction endonucleases are available both in printed and computer readable forms, and are provided by many commercial suppliers (e.g., New England Biolabs, Ipswich, Mass.). A non-limiting list of restriction endonucleases and associated recognition sites may be found at: www.neb.com/tools-and-resources/selection-charts/alphabetized-list-of-recognition-specificities.

In some embodiments, modified or non-nucleotides can provide a cleavable moiety. For example, uracil bases (can be cleaved with combination of UGD and endonuclease VIII or FPG as one example), abasic sites (can be cleaved by Endonuclease VIII as one example), 8-oxo-guanine (can be cleaved by FPG or OGG1 as examples) and ribose nucleotides (can be cleaved by RNAseH2 in when paired with DNA in one example) as described above.

Ligateable Ends

In some embodiments, adapter products are generated with a ligateable 3' end suitable for ligation to target double-stranded nucleic acid sequences (e.g., for sequencing library preparation). In some embodiments, a template strand comprises a 3' ligation domain that comprises a template sequence for generating a double-stranded cut site. Such a cut site may be a restriction endonuclease recognition sequence, or in another embodiment, can be cleavable non-standard nucleotides. Following extension of the elongation strand and further processing at the cut site(s), the resultant ligation domains present in each of the double-stranded adapter product may be capable of being ligated to one corresponding strand of a double-stranded target nucleic acid sequence. In some embodiments, one of the ligation domains includes a T-overhang, an A-overhang, a CG-overhang, a blunt end, or another ligateable nucleic acid sequence. In some embodiments, a double-stranded 3' ligation domain comprises a blunt end. In certain embodiments, at least one of the ligation domain sequences includes a modified or non-standard nucleic acid. In some embodiments, a modified nucleotide may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. In some embodiments, at least one strand of the ligation domain includes a dephosphorylated base. In some embodiments, at least one of the ligation domains includes a dehydroxylated base. In some embodiments, at least one strand of the ligation domain has been chemically modified so as to render it unligateable (e.g., until a further action is performed to render the ligation domain ligateable). In some embodiments a 3' overhang is obtained by use of a polymerase with terminal transferase activity. In one example Taq polymerase may add a single base pair overhang. In some embodiments this is an "A".

Non-Standard Nucleotides

In some embodiments, provided template and/or elongation strands may include one or more non-standard/non-canonical nucleotides. In some embodiments, a non-standard nucleotide may be or comprise a uracil, a methylated nucleotide, an RNA nucleotide, a ribose nucleotide, an 8-oxo-guanine, a biotinylated nucleotide, a desthiobiotin nucleotide, a thiol modified nucleotide, an acrydite modified nucleotide an iso-dC, an iso dG, a 2'-O-methyl nucleotide, an inosine nucleotide Locked Nucleic Acid, a peptide nucleic acid, a 5 methyl dC, a 5-bromo deoxyuridine, a 2,6-Diaminopurine, 2-Aminopurine nucleotide, an abasic nucleotide, a 5-Nitroindole nucleotide, an adenylated nucleotide, an azide nucleotide, a digoxigenin nucleotide, an I-linker, a 5' Hexynyl modified nucleotide, an 5-Octadiynyl dU, photocleavable spacer, a non-photocleavable spacer, a click chemistry compatible modified nucleotide, a fluorescent dye, biotin, furan, BrdU, Fluoro-dU, Ioto-dU, and any combination thereof.

B. Various Embodiments of Methods and Reagents for Solid-Phase Adapter Synthesis The present disclosure also provides methods and reagents for solid-phase adapter synthesis. In some embodiments, one or more capture labels may be used for enrichment/selection of desired adapter product(s), for example, via positive enrichment/selection or negative enrichment/selection, similar to such methods used in solution-based adapter synthesis methods.

In some embodiments, methods including a solid-phase synthesis process include an initial step of associating a template strand with a functionalized surface. In some embodiments, a template strand will include one or more capture labels, and the functionalized surface will include one or more extraction moieties capable of binding or otherwise associating with the one or more capture labels on the template strand in either the presence or absence of a specific chemical reaction whereby the capture label moiety and the functionalized surface moiety are chemically linked or associated.

Figure 7:
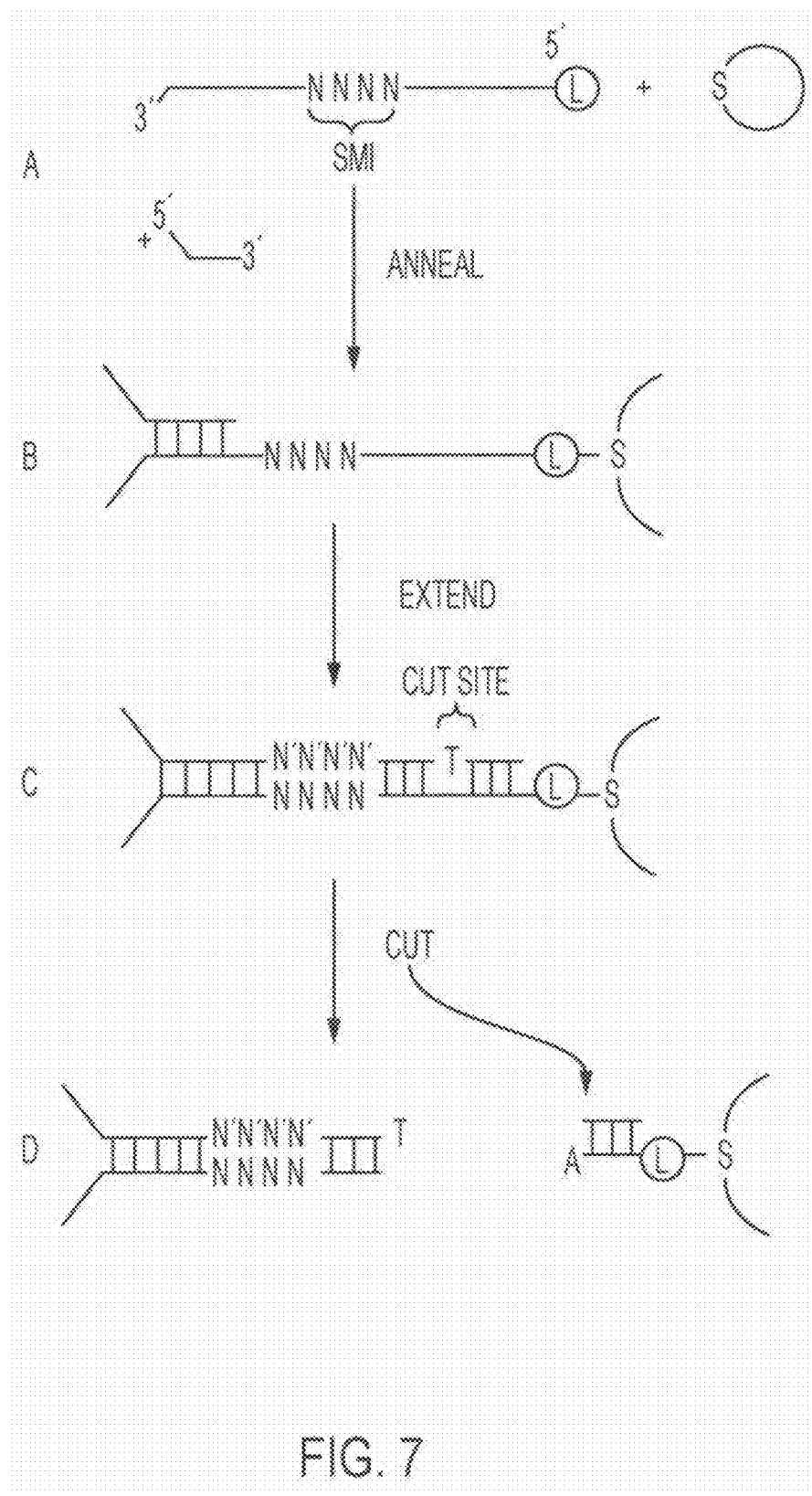
FIG. 7 depicts an embodiment of a method for a solid-phase adapter synthesis scheme using a capture label. Panel A illustrates the addition of a template strand comprising a 5' capture label and a functionalized surface capable of binding the capture label to a reaction mixture. The template strand binds to the functionalized surface via the capture label, and an elongation strand is added to facilitate annealing. Panel B illustrates the annealing of the template strand and the elongation strand at an at least partially complementary region forming a pre-adapter complex. The pre-adapter complex is then enzymatically extended to form a double-stranded sequence having a SMI in each strand. Panel C illustrates the enzymatically extended uncut adapter complex containing a double-stranded SMI. After cutting a 3' region of the double-stranded sequence (e.g., the ligation domain) at a cut-site using, e.g., a restriction endonuclease enzyme, the desired adapter product is separated from the cleaved fragment bound to the functionalized surface as illustrated in Panel D. The unlabeled desired adapter product is then purified by separating the functionalized surface with bound intermediates/byproducts from the desired adapter product having a duplex SMI.

The embodiment exemplified in FIG. 7 encompasses an enrichment/selection scheme wherein pre-adapter products are retained on a functionalized surface (e.g., or otherwise immobilized) during processing. In each step of the process, undesired intermediates and/or byproducts not bearing the capture label are washed away or removed at various phases of the synthesis process. In some embodiments, solid-phase synthesis methods allow for use of an excess of the elongation strand, at least in part because free/unhybridized elongation strand can be removed during processing while excess template strand and all intermediates/byproducts bearing the capture label remain bound. In some embodiments, a duplex adapter product is released from the functionalized surface (e.g., immobilization) in a final processing step while process intermediates and byproducts bearing the capture label remain bound. Accordingly, a double-stranded cut recognition site can be included in the adapter product to ensure that extension has been completed before release of the adapter from the functionalized surface can occur.

In the solid-phase adapter synthesis method described in FIG. 7, a template strand comprising a SMI and a capture label at the 5' end of the strand is associated (e.g., linked, bound, immobilized, conjugated, chemically reacted with, covalently bonded to, ionically bound to etc.) via its 5' end with a functionalized surface, for example, via interaction between a capture label on the template strand and an extraction moiety on the functionalized surface (FIG. 7, panel A). In some embodiments, such association may occur prior to, or substantially simultaneously with, an annealing step. In some embodiments, the template strand may also include a template sequence for a ligation domain (e.g., for forming a double-stranded cut site), for example, 3' to the 5' capture label. Optionally, the template strand includes features such a primer binding site, read primer sequence and/or a region of non-complementarity or another feature for providing an SDE.

Then, the elongation strand (optionally, including a primer binding site, a read primer sequence and/or a region of non-complementarity or other feature for providing an SDE) and the template strand are annealed at an at least partially complementary region in a reaction mixture to create a pre-adapter complex (FIG. 7, panel B). Because the pre-adapter complex is associated with the functionalized surface, excess elongation strand can then be washed away through successive wash steps reducing the presence of residual intermediates without substantial loss of pre-adapter complex. The elongation strand may then be enzymatically extended from the 3' end to include an SMI and a cut site for creating a double-stranded uncut adapter complex. A double-stranded cut site can provide both a mechanism of purification of desired adapter products (e.g., separation from capture label-bound entities) and manner of generating a 3' ligateable end of the adapter product. One of ordinary skill in the art will appreciate that a cut site can be provided to accomplish one or more of these processing aspects and/or multiple cut sites can be provided to accomplish different processing aspects.

FIG. 7, panel C illustrates the bound double-stranded uncut adapter complex after enzymatic extension, wherein double-stranded SMI and restriction enzyme cut sites are created. In some embodiments, the desired adapter product is released into solution by treatment with a restriction endonuclease that cuts at the restriction enzyme cut-site while remaining intermediate products, if any, and byproducts are retained by the functionalized surface via the capture label (FIG. 7, panel D). The desired adapter product can be isolated by any of a variety of methods, for example, elution, or removal of the functionalized surface from the reaction mixture. In some embodiments, an alternative method to the scheme illustrated in FIG. 7, may include introduction of the functionalized surface after the enzymatic extension step to capture uncut adapter complexes (see, e.g., FIG. 9).

Figure 8:
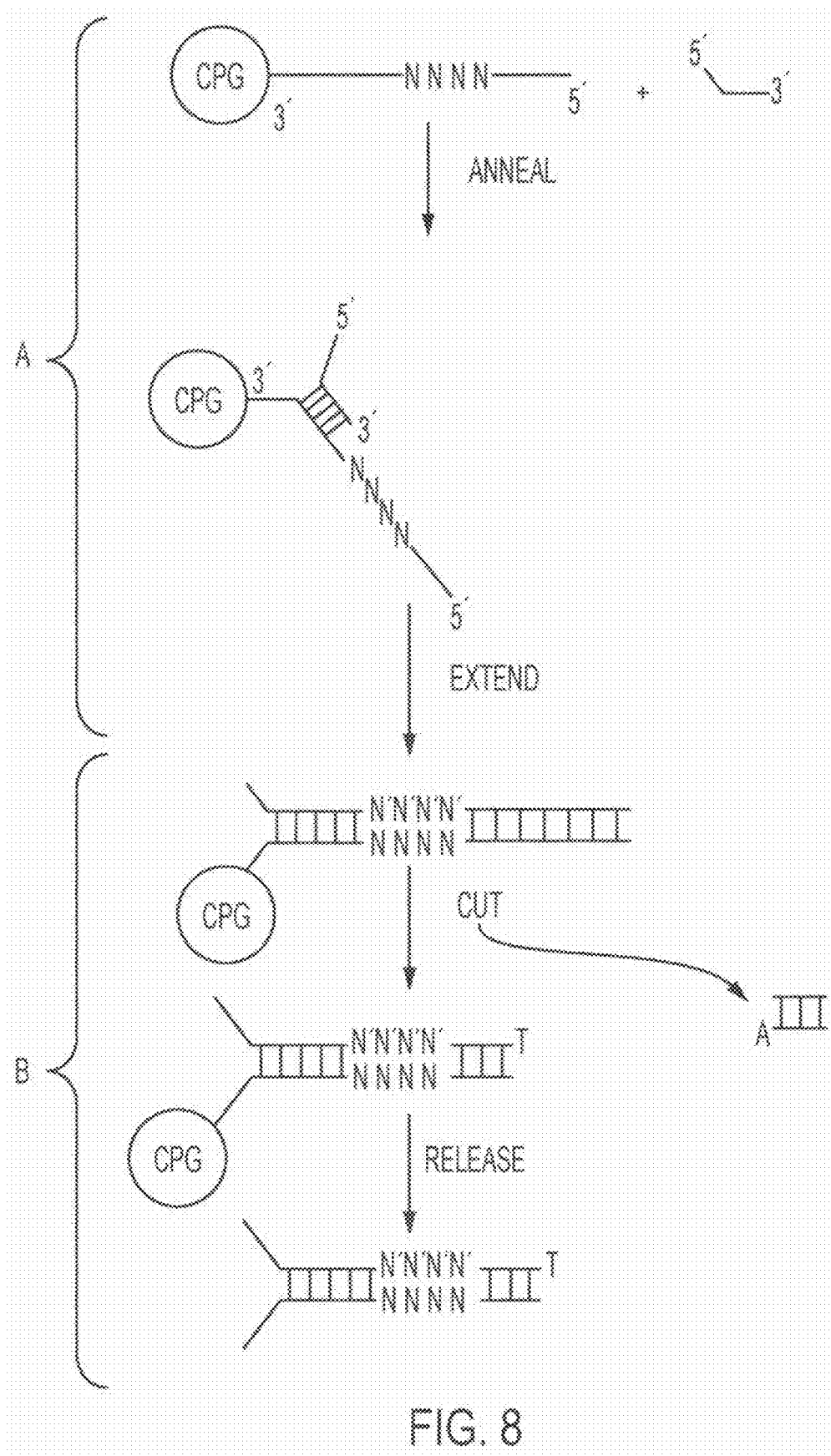
FIG. 8 depicts another embodiment of a method for a solid-phase adapter synthesis scheme. Panel A illustrates a template strand pre-bound to an oligonucleotide synthesis solid support (e.g., controlled pore glass beads) at a 3' terminal end and extending from the solid support to a 5' terminal end in a reaction mixture. An elongation strand is added to the reaction mixture where it anneals to the template strand at an at least partially complementary region to form a pre-adapter complex. Panel B illustrates enzymatic extension of the elongation strand followed by cleavage at a cut site to form a ligateable end of the adapter complex. Following cleavage, the desired adapter product having a duplex SMI is released from the oligonucleotide synthesis solid support and retrieved.

In some embodiments, it may be desirable to associate a template strand comprising a SMI with a functionalized surface via the template strand's 3' end. Without wishing to be held to a particular theory, it is contemplated that certain polymerases may not be optimally suited to properly elongate a desired adapter product when the template strand is attached at the 5' end. Accordingly, in some embodiments, solid-phase adapter synthesis can be further enabled through immobilization of the template strand at the 3' end, as is shown in FIG. 8. In some embodiments, template strands may optionally include a restriction endonuclease cut site on the 5' end for, e.g., generating a 3' ligateable end of the adapter product. In certain arrangements, not shown, a capture label at the 5' end of the strand may also be included such that introduction of a functionalized surface suitable for extracting nucleotide molecules bearing the 5' capture label can be removed (e.g., negative selection scheme for adapter products that have been properly cut with ligateable 3' ends).

In one embodiment, and as illustrated in FIG. 8, the 3' end of the template strand can be covalently linked to a surface, such as result of oligonucleotide synthesis. Once processing is complete, the covalent bond can be broken, and the desired adapter product can be released. In an alternative embodiment, the template strand can comprise a 3' capture label and a cleavable moiety positioned 5' to the 3' capture label.

As illustrated in FIG. 8, a template strand can be associated with controlled pore glass (CPG) beads at a 3' end of the strand, such as following a conventional protocol for synthesizing an oligonucleotide (e.g., the template strand synthesis) (see FIG. 8, panel A). The artisan skilled in oligonucleotide manufacturing and nucleic acid purification methods will appreciate that other surfaces and/or beads (e.g., microporous polystyrene (MPPS) beads) can be used for oligo synthesis and/or otherwise providing a template strand pre-bound to a surface (e.g., via chemical bond).

Following template strand synthesis, for example, free/unhybridized elongation strand can be introduced to the reaction mixture and the template strand is annealed with an elongation strand at an at least partially complementary region to form a pre-adapter complex similarly to the other embodiments outlined above (FIG. 8, panel A). Also similar to other embodiments described herein and above, enzymatic extension may be used to generate a double-stranded adapter complex containing a SMI sequence in both strands and a 5' cut site (FIG. 8, panel B). In some embodiments, for example, embodiments including a ligation domain, a cleaving event (e.g., cutting with a restriction enzyme) at the 5' end may result in formation of a ligateable end. In some embodiments, the ligateable end is free, so potential problems, such as those associated with large polymerases, for example, knocking the adapter product from the functionalized surface prematurely, are reduced or eliminated. A byproduct cleavage fragment can be washed away in next step, or alternative, can be negatively selected for via affinity purification (if a capture label was provided; not shown). Subsequent to extension and cutting, the desired adapter product can be released from the CPG beads (such as via chemical or thermolytic means) and recovered resulting in a purified adapter product (see FIG. 8, panel B). As discussed above, and in some embodiments, the template strand can have a 3' capture label with associated cleavable moiety and be captured by a different functionalized surface (not pre-bound).

C. Additional Embodiments of Methods and Reagents for Adapter Synthesis

Figure 9:
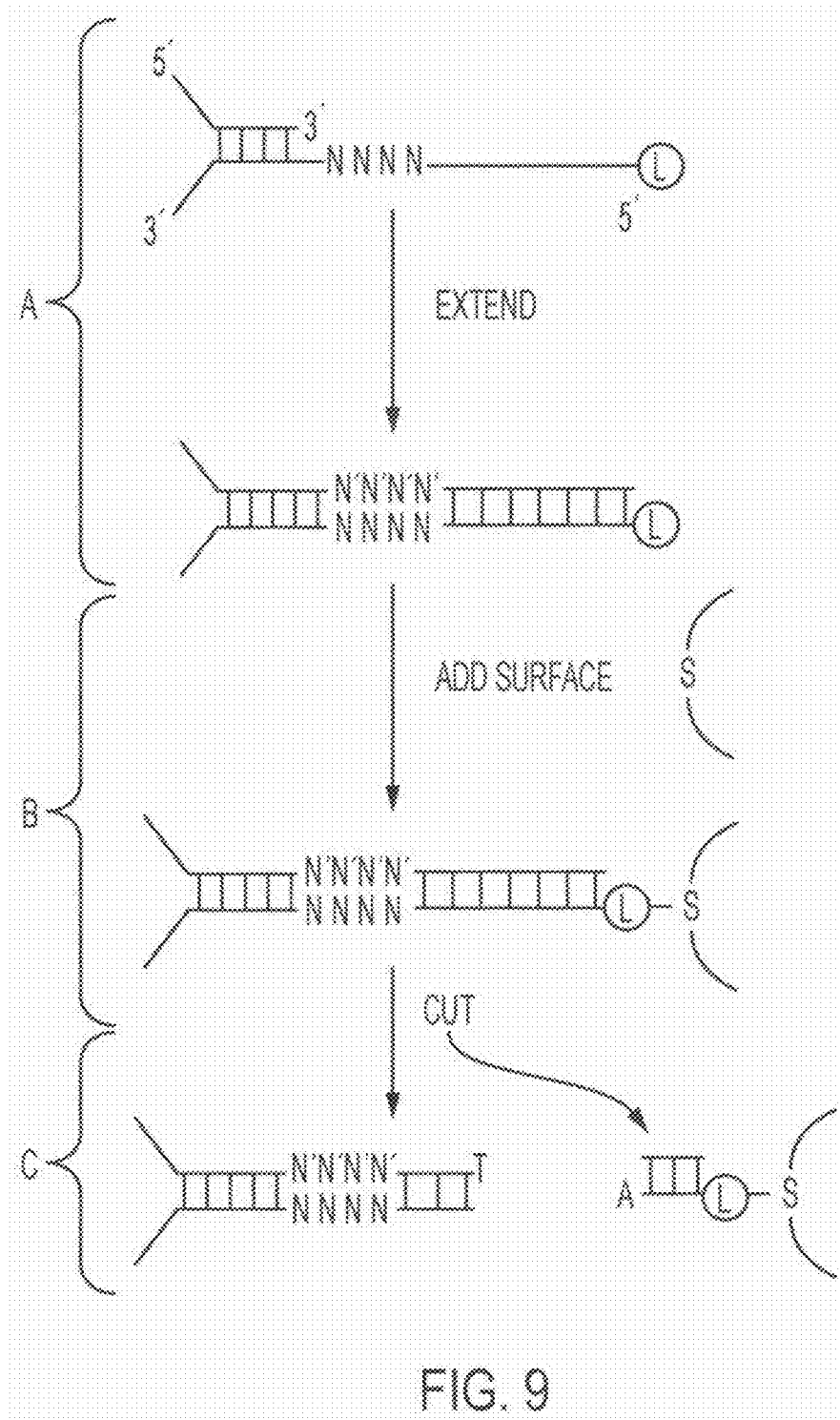
FIG. 9 depicts an embodiment of a method for a hybrid solution-phase/solid-phase adapter synthesis scheme using a capture label. Panel A shows enzymatic extension of the elongation strand of the pre-adapter complex in solution. Following enzymatic extension, a functionalized surface is introduced to interact with a 5' capture label on the template strand of the uncut adapter complex (Panel B). Panel C illustrates a cleavage event at a double-stranded 3' region (e.g., a ligation domain) cut-site, thereby releasing the purified adapter product having a duplex SMI into solution.

In addition to the solution-phase and solid-phase methods described above, it is also possible to combine the two in various hybrid schemes, for example, as is depicted in FIG. 9. In some embodiments, such a hybrid approach can include any portion of the steps in solution-phase and/or solid-phase methods, and in any application-appropriate order. In some embodiments, a hybrid approach may be advantageous in providing certain benefits not attainable using only a solution-phase or solid-phase synthesis method. For example, in some embodiments, a hybrid method may provide certain benefits of associating a template strand with a functionalized surface via the 5' end following extension of the elongation strand (e.g., preventing larger polymerases from disassociating the pre-adapter complex from a functionalized surface prior to completion). For example, a hybrid approach may include performing the annealing and extension steps in solution and the double-stranded pre-adapter complexes are then associated with a functionalized surface via a capture label on the 5' end of the template strand.

In the embodiment shown in FIG. 9, panel A, annealing of an elongation strand to a template strand at a region of at least partial complementarity, as well as extension (e.g., enzymatic extension) of the elongation strand (e.g., with a DNA polymerase) to produce an elongated double-stranded portion of the pre-adapter complex occurs in solution. Then, as illustrated in FIG. 9, panel B, the double-stranded pre-adapter complex can be associated with a functionalized surface, for example, via a capture agent on the 5' end of the template strand. As extension is already complete at this point, spatial constraints at or near the capture label can be avoided. Following association with the functionalized surface, a cleavage event, for example at a restriction endonuclease cut site, can be made to occur to release the desired adapter product only (FIG. 9, panel C), either immediately after association (e.g., immobilization) with the functionalized surface, or after the performance of one or more desired additional processing steps (e.g., wash or other purification or enrichment steps). In some embodiments, a cleavage event can be designed to be double-strand specific, thereby requiring extension to have substantially completed in order for release to occur.

In other embodiments, a template strand can comprise a region of self-complementarity such that the template strand provides an elongation portion and a separate elongation strand is not required. Said another way, an elongation strand may be associated with a template strand via linker domain (e.g., a loop comprising single-stranded nucleotides). The linker domain (e.g., the hairpin loop) can comprise one or more cleavable moieties. In such embodiments, a template strand comprising a 3' hairpin loop structure (e.g., as described further below with respect to FIGS. 12-13D) and a 5' capture label can be provided as pre-adapter complex suitable for further processing. The template and elongation strands/portions of the pre-adapter complex may be structured as described above for the solution-phase and/or solid-phase methods (e.g., may include one or more pre-defined sequences, one or more regions of degenerate or semi-degenerate sequence (e.g., an SMI, an identifier sequence), one or more capture labels, one or more cut sites, etc.). In some embodiments, any of the process steps, reagents, and designs described above for solution-phase and/or solid-phase methods may be equally applicable in embodiments including a cleavable moiety as described in FIGS. 10A-B. For example, one or more extension, cutting, associating, and/or removing steps may occur either as described for solution-phase and/or solid-phase.

Figure 10A:
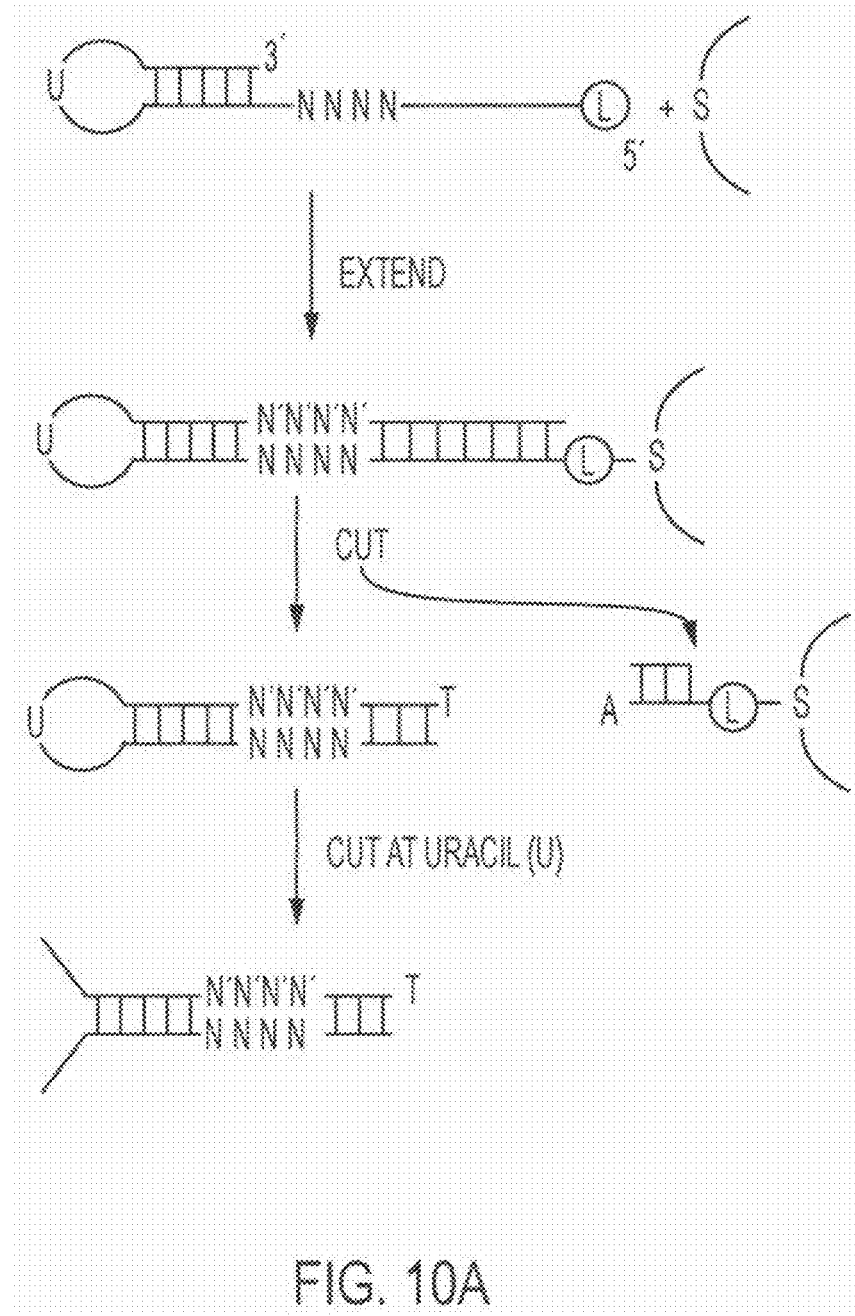
FIG. 10A illustrates a negative enrichment/selection method for adapter synthesis using a template strand comprising a 5' capture label to remove undesirable byproducts and/or undesirable intermediate adapter synthesis products, and a cleavable linker that can be cut to generate a Y-shaped duplex adapter structure.
Figure 10B:
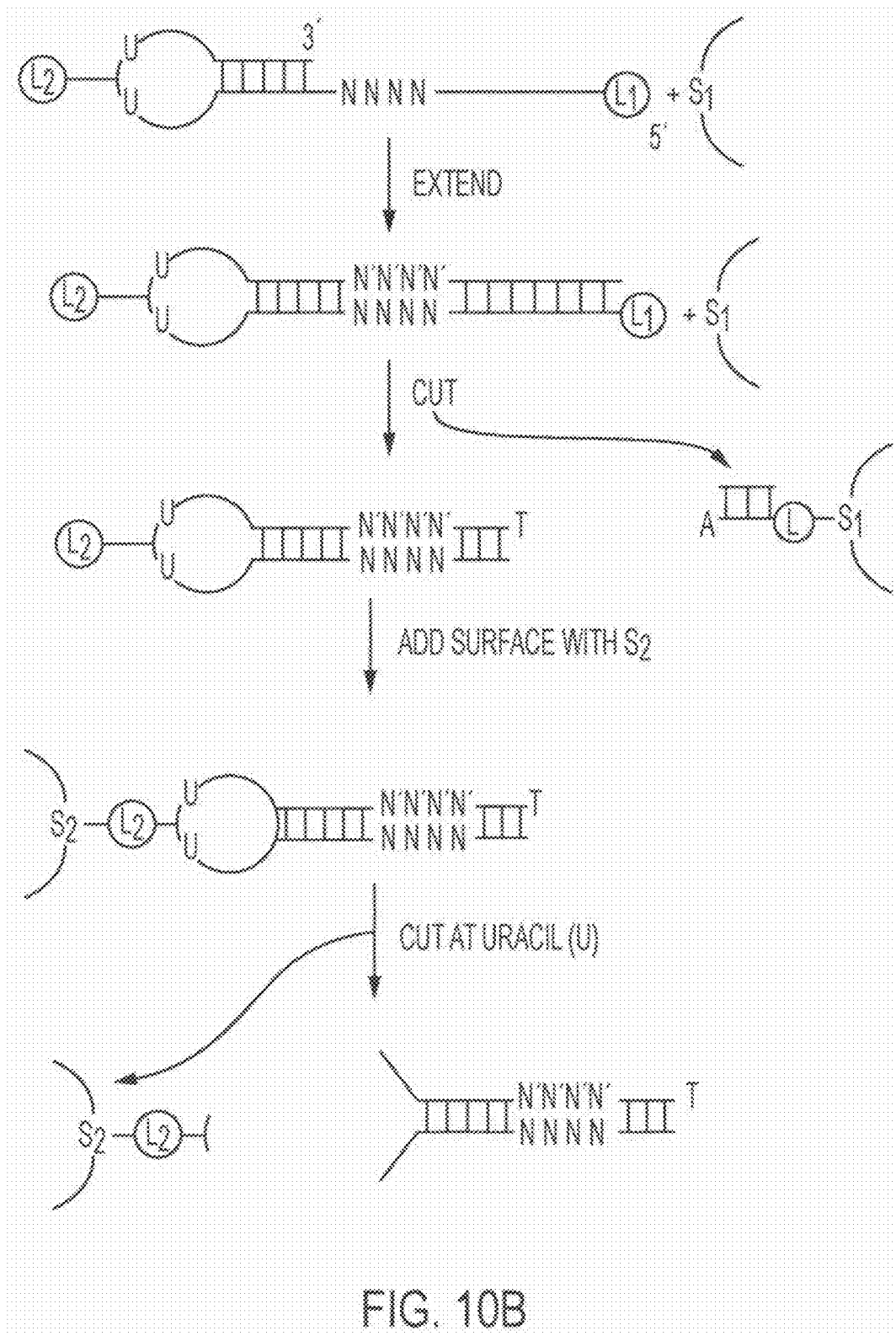
FIG. 10B illustrates a method of adapter synthesis comprising both negative and positive enrichment/selection schemes using a template strand comprising a 5' capture label to remove undesirable byproducts and/or undesirable intermediate adapter synthesis products, and a second capture label provided on a linker sequence of a hairpin loop structure configured to select for desired adapter products wherein the linker has successfully been cleaved to form a Y-shaped duplex adapter structure.

FIG. 10A depicts an embodiment incorporating both a cleavable moiety and a single capture agent into the pre-adapter complex. After formation of the pre-adapter complex, FIG. 10A depicts extension and cutting steps substantially similar to those depicted in FIG. 5 and described in the section entitled "Single Capture Agent Example" above, which allows for use of negative enrichment/selection techniques as described. Briefly, either before or after extension of the pre-adapter complex to form a double-stranded pre-adapter complex, the capture label may be associated (e.g., linked) to a functionalized surface. After association with the functionalized surface, a double-stranded uncut adapter complex can be cut at a designed cut site, for example, with an appropriate enzyme, or, if desired, one or more washing or other purification steps may be performed on the reaction mixture prior to cutting.

Upon treatment of the double-stranded uncut adapter complex with an appropriate enzyme to interact with the pre-adapter complex at the cut site, the cleaved fragment including the capture agent (byproduct) and other undesired intermediates comprising the capture label (e.g., free/unhybridized template strand, un-extended or partially extended pre-adapter complex, uncut double-stranded pre-adapter complex) may be removed via removal of the functionalized surface leaving the desired adapter product in solution. In some embodiments, a restriction endonuclease enzyme that cuts a restriction endonuclease recognition cut site (e.g., within a ligation domain 3' to the SMI) may produce a 3' ligateable end on the desired adapter product. In FIG. 10A, the ligateable end is shown as a T-overhang, however, similar to above described embodiments, it will be apparent to one of skill in the art that the ligateable end can be any of a variety of forms, for example, a blunt end, an A-overhang, a "sticky" end comprising more than one nucleotide overhang, among others. Regardless of whether or how a ligateable domain may be introduced to the desired adapter product, the cleavable moiety present in the linker domain is cleaved to open the hairpin loop to form a desired adapter product (depicted in FIG. 10A as a Y-shaped adapter).

Alternatively, in some embodiments, pre-adapter complexes including a hairpin loop structure linking the template and elongation strands (e.g., portions) can also incorporate two (or more) capture labels, for example, a first capture label being present on the 5' end of the template strand, and a second capture label being present in the linker domain of the hairpin loop structure. In some embodiments, such as that shown in FIG. 10B, the first capture label is positioned 5' to a cut site (e.g., a restriction endonuclease cut site) and the second capture label is positioned between two cleavable moieties in the single-stranded loop/linker sequence of the hairpin loop structure. In some embodiments, use of a double capture label approach allows for use of both negative and positive enrichment/selection techniques for producing a desired adapter product. Exemplary positive and negative selection approaches that are compatible with the inclusion of a hairpin loop structure are shown in FIG. 6 and described above in the section entitled "Multiple Capture Agent Example." Briefly, after extension of the pre-adapter complex, the first capture label may be associated (e.g., linked) to a first functionalized surface. After association with the first functionalized surface, the double stranded uncut adapter complex can be cut at a cut site, for example, with an appropriate enzyme to interact with the pre-adapter complex at the cut site, or, if desired, one or more washing or other purification steps may be performed on the reaction mixture prior to cutting.

After cutting, cleaved fragments (byproducts) and other undesired intermediates comprising the capture label (e.g., free/unhybridized template strand, un-extended or partially extended pre-adapter complex, uncut double-stranded pre-adapter complex) may then be removed via removal of the functionalized surface leaving the desired adapter product in solution. The second capture label may be associated (e.g., immobilized) to a second functionalized surface. In one embodiment the first and second capture labels are different and the first and second functionalized surfaces or extraction moieties can be introduced sequentially (e.g., in either order) or simultaneously. In other embodiments, the first and second capture labels are the same and/or are captured by the same functionalized surface (e.g., a functionalized surface comprising compatible affinity partners for both first and second capture labels, presentation of an extraction moiety that interacts with both first and second capture labels, etc.). After association with the second functionalized surface, one or more wash or other purification steps may be performed as desired in order to remove contaminants, intermediates or byproducts as described above. At a desired time, the cleavable moieties are cleaved to release the desired adapter product (shown as a Y-shaped adapter in FIG. 10B). In the example shown in FIG. 10B, a second capture moiety is immobilized by surface (S2). Non-standard nucleotides (e.g., uracil) flank the second capture label within the loop of the hairpin loop structure. Positive enrichment/selection is achieved when the desired adapter product is released completely from the second capture label following cleavage at both non-standard nucleotides. In the illustrated example, USER (UDG and Endonuclease VIII) can be introduced to the reaction mixture to cleave at both uracil bases, thereby releasing the desired adapter product having an identifier sequence (e.g. a SMI) in both strands.

Once the cleavable moieties have been cleaved, the desired adapter product may be collection, for example, via elution or other separation technique. Potential advantages to certain embodiments incorporating a hairpin loop structure as described include ensuring that substantially all products are double-stranded (e.g., no free/unhybridized byproducts pass through to the final adapter product), and the ability to ensure a substantially 1:1 molar ratio of the template and elongation strands (e.g., portions), which would reduce or eliminate the need to wash or otherwise purify excess template or elongation strands from the reaction mixture.

Index Sequences

In some embodiments, use of one or more indexing sequences (e.g., indexing barcodes) may be used. In accordance with various embodiments, an index sequence may be integrated at any application-appropriate position within an adapter complex (e.g., in a single stranded portion, a double stranded portion). By way of example, in some embodiments, an index sequence can be integrated 5' to an SMI in a double-stranded portion of the adapter. In some embodiments, an index sequence can be integrated 3' to an SMI in a double-stranded portion of the adapter. In some embodiments, an index sequence may be integrated within an SMI (e.g., between two degenerate or semi-degenerate sequences). Accordingly, in some embodiments, index sequences may be at least partially complementary between the two strands of double-stranded adapter. In other embodiments, index sequences may reside in a single-stranded portion (e.g., on an arm of an adapter, within a bubble formed in the adapter, etc.) In still further embodiments, an index sequence may partially reside within an uncomplimentary portion and within a complementary portion of the duplex adapter. Further, an adapter may include more than one index sequence in each strand of the adapter, and any index sequence may be present along with other barcodes or identifier sequences present in the duplex adapter.

Figure 11A:
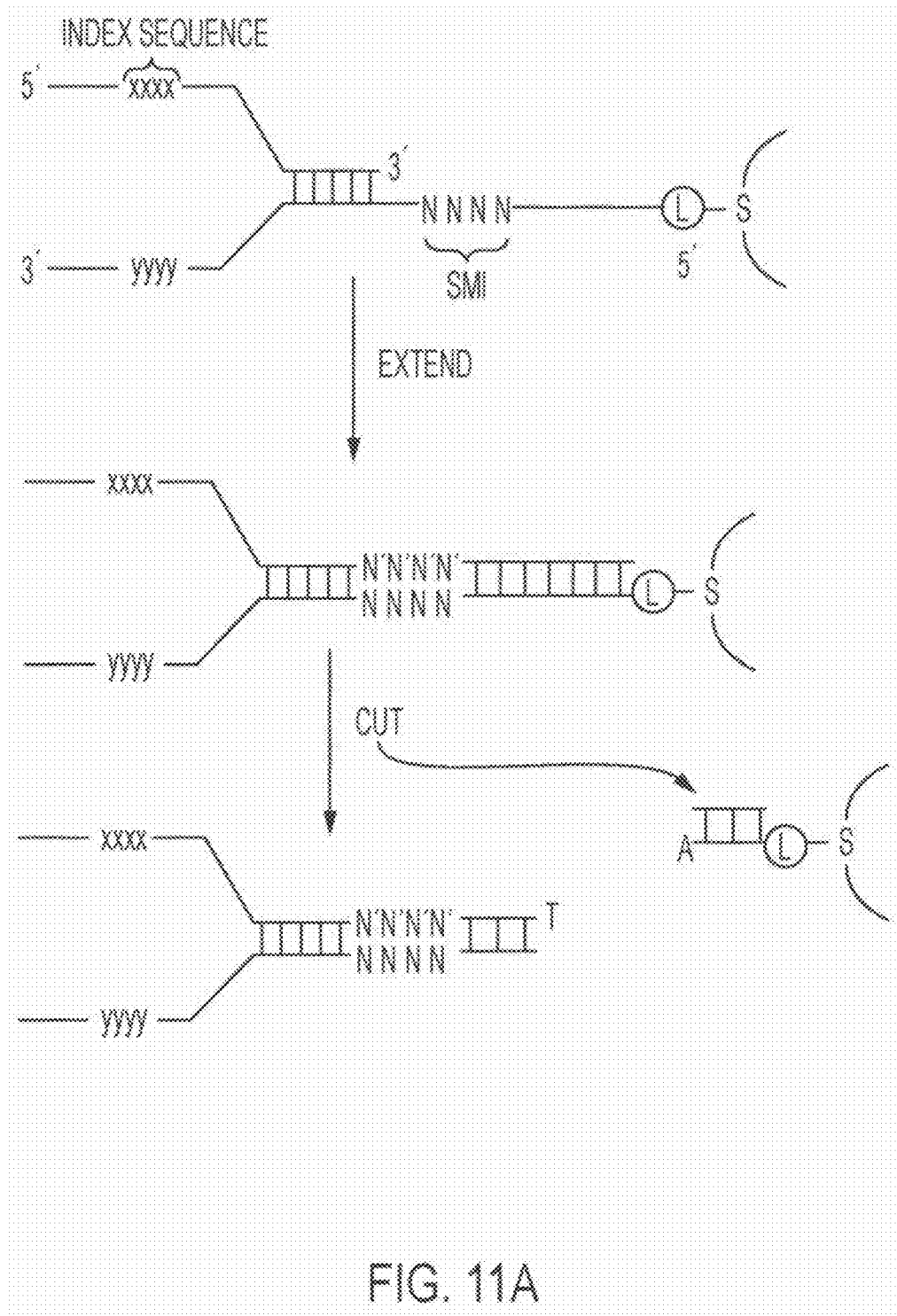
FIG. 11A illustrates an embodiment of a solid-phase adapter synthesis scheme having index sequences in the non-complementary regions of the elongation and template strands. The elongation and template strands can comprise the index sequences prior to the annealing step to generate a pre-indexed adapter complex suitable for sample-specific labeling of a nucleic acid library.
Figure 11B:
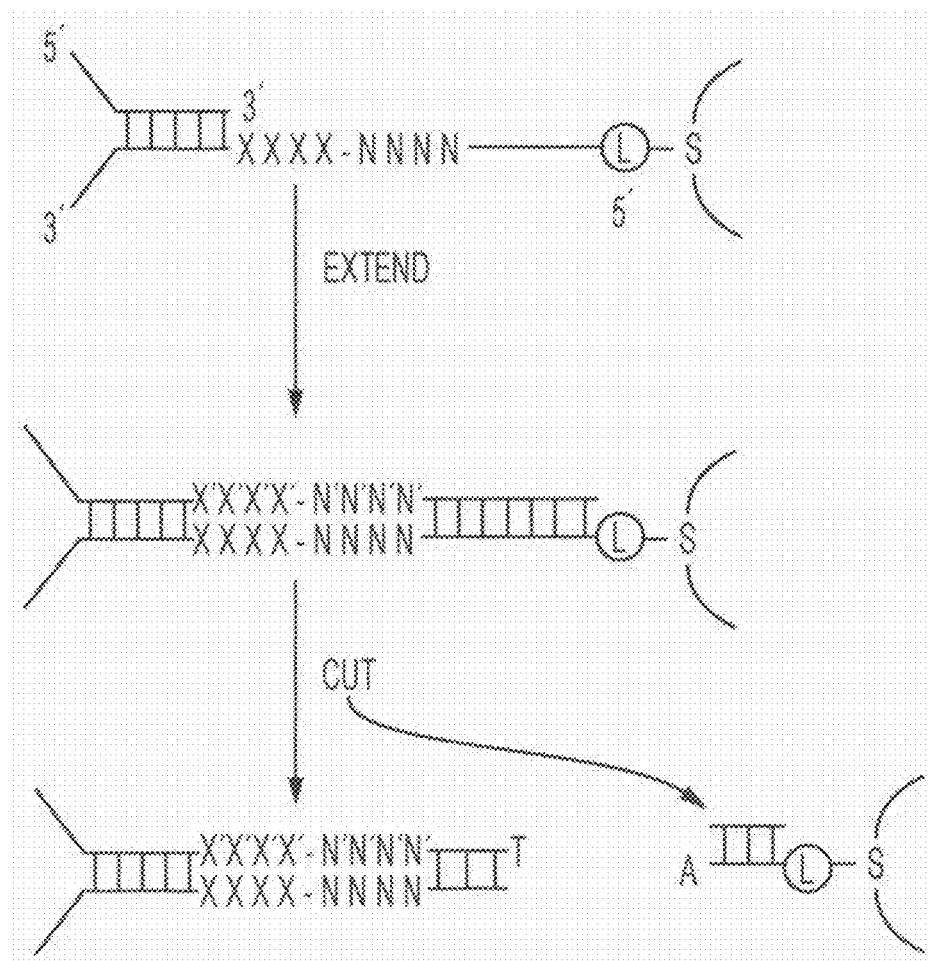
FIG. 11B illustrates an embodiment of a solid-phase adapter synthesis scheme having an index sequence (designated "XXXX") present in the template strand. Following annealing and extension steps of the adapter synthesis, the index sequence is present in the double-stranded region of the adapter sequence in both the elongation and template strands.

In some embodiments, indexing sequences can be used to label samples such that samples can be distinguishable from each other following sequencing, for example, on flow cells. In some embodiments, indexing sequences are incorporated into a sample library following a first round of amplification using index primers (e.g., index sequences are provided in the tails of primers). FIG. 11A and FIG. 11B illustrate embodiments of methods of synthesizing adapter complexes having index sequences so that indexing rounds of amplification are not necessary. It is specifically contemplated that the use of index sequences is compatible with solution-phase, solid-phase, and/or hybrid techniques as are described herein.

By way of specific example, FIG. 11A illustrates a solid-phase adapter synthesis scheme including index sequences "xxxx" and "yyyy" in non-complementary regions of the elongation and template strands (sometimes referred to as the "tail" or "arm" of a Y-shaped adapter). Though the index sequences shown in FIG. 11A are depicted as four nucleotides in length, any application-appropriate number of nucleotides may be used in a particular index sequence (e.g., between about 2 and 40 or more nucleotides). In some embodiments, elongation and/or template strands can be synthesized in a manner to include the index sequences (e.g., indexing barcodes) prior to the annealing step to generate a pre-indexed adapter complex suitable for sample-specific labeling of a nucleic acid library. The use of such pre-indexed adapter complexes is compatible with the methods described herein including, but not limited to single capture label techniques (which are depicted in FIG. 11A), multiple capture label techniques, and hairpin incorporation.

Briefly, FIG. 11A shows the inclusion of two index sequences "xxxx" and "yyyy" in non-complementary regions of the template and elongation strands, and formation of a pre-adapter complex. In using a solid-phase synthesis scheme as depicted, the template strand can be immobilized to a functional surface (S) via the 5' capture label either before, during or after an annealing step. Once annealed, the elongation strand then undergoes extension as described elsewhere herein, for example, via enzymatic extension from the 3' end to produce an extended double-stranded pre-adapter complex. After association with the functionalized surface and extension of the elongation strand, the double stranded uncut adapter complex can be cut at a cut site, for example, with an appropriate enzyme to interact with the pre-adapter complex at the cut site, or, if desired, one or more washing or other purification steps may be performed on the reaction mixture prior to cutting. Upon treatment of the double-stranded uncut adapter complex with an appropriate enzyme to interact with the cut site, the cleaved fragment (byproduct) including the capture agent remains bound to the functionalized surface. The functionalized surface may be separated from solution, thereby removing undesired intermediate products (e.g., free/unhybridized template strand, un-extended or partially extended pre-adapter complex, uncut double-stranded pre-adapter complex) and byproducts bearing the capture label. For accomplishing a negative enrichment/selection of the desired adapter product, the functionalized surface having one or more extraction moieties bound thereto is capable of binding to the capture label (e.g. a streptavidin bead where the capture label is biotin) for immobilization and separation of molecules bearing the capture label. Any capture label and compatible extraction moiety as described herein, or those known in the art, may be used.

As an addition or alternative to including one or more index sequences in a region of non-complementarity between a template strand and an elongation strand (as is shown in FIG. 11A), one or more index sequences may be integrated into the double-stranded portion of an adapter sequence (sometimes referred to as the "stem" of an adapter sequence).

FIG. 11B illustrates an embodiment of a solid-phase adapter synthesis scheme having an index sequence present in the template strand. Specifically, following annealing and extension steps of the adapter synthesis, substantially as described elsewhere herein, the index sequence is present in the double-stranded region of the adapter complex in both the elongation and template strands. In some embodiments, an advantage to including an index sequence in the double-stranded portion of the adapter complex is that the index sequence can be acquired in the same sequence read as the SMI/target nucleic acid sequence read, rather than requiring a separate read.

Extension in the Direction Away from the Ligateable End

The above examples illustrate methods that utilize a 5' to 3' polymerase to enzymatically extend the elongation strand using the template strand as a template. The following examples illustrate embodiments of methods for forming adapter complexes that use a 5' to 3' polymerase to enzymatically extend from an extendable 3' end in such a way that the polymerase travels in the direction away from the ultimate litigable end of the adapter molecule. As shown in examples of =certain embodiments this can be facilitated by a hairpin structure whereby a portion of the template strand self-folds on itself to also serve as the extension strand to generate a double-stranded region of the complex from which an extension can occur from which to generate a double stranded SMI. In some embodiments, such methods are particularly amenable to incorporation of one or more modified or non-standard bases into the template strand (inclusive of the portion that self-anneals to form the extension strand, for example, to generate cleavage sites for removing 3' complex byproducts, release desired adapter products from a functionalized surface for enrichment purposes, and to generate a ligateable (e.g., sticky) 3' end of the adapter without the use of restriction enzymes or sequence specific endonucleases.

Figure 12:
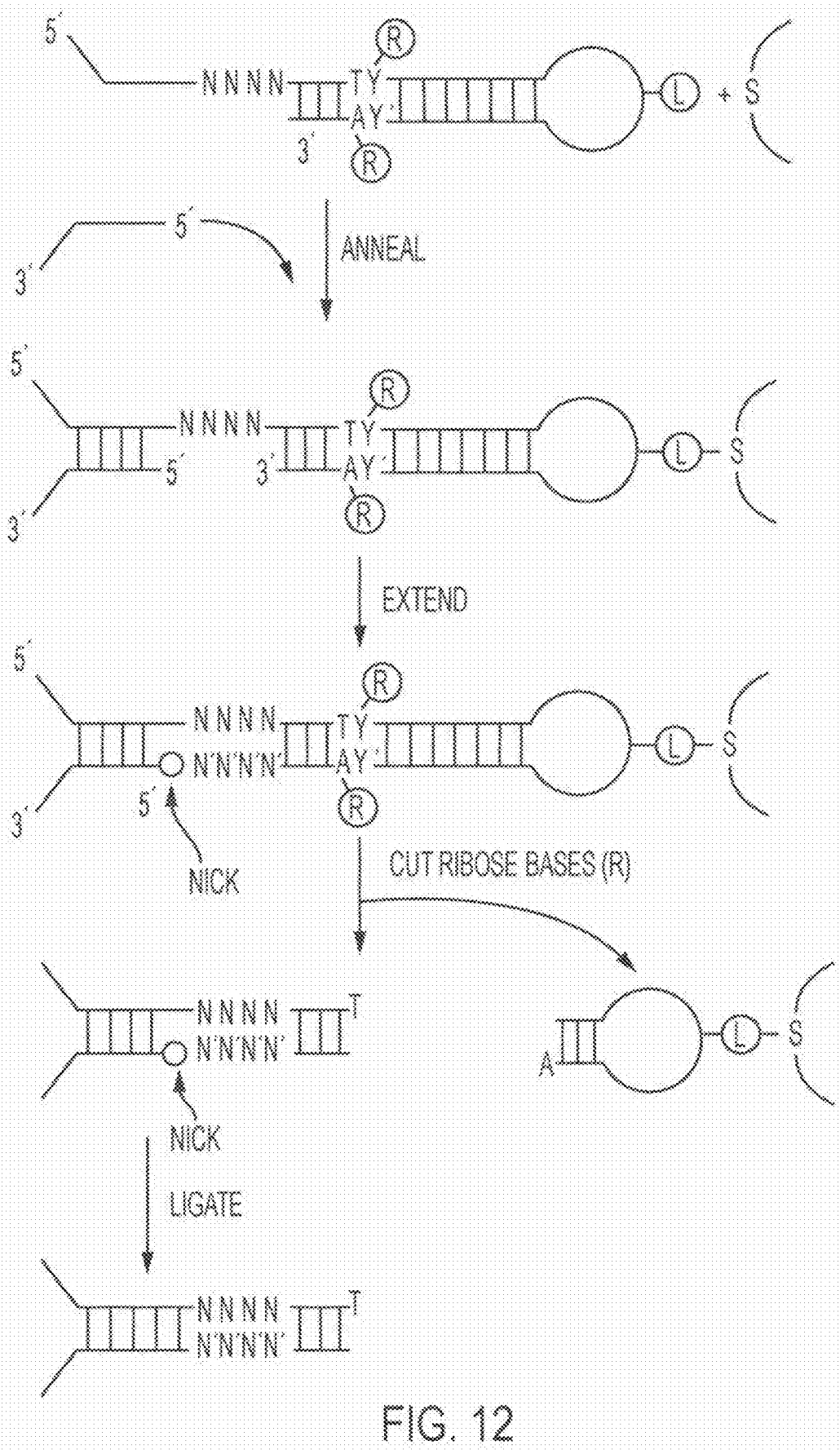
FIG. 12 depicts an embodiment of a method of a reverse adapter synthesis scheme. A template strand comprising a SMI sequence and a hairpin loop structure proximate a 3' end is annealed to an elongation strand at an at least partially complementary region. The hairpin loop structure includes a self-complementary stem portion and a single-stranded nucleotide linker portion. A polymerase extends the terminal 3' end of the template strand to meet the 5' end of the annealed elongation strand to form a double-stranded region of the adapter complex having the SMI sequence in both strands. A modified or non-standard base is incorporated into the template strand in the stem portion such that a directed cleavage event at the modified or non-standard base releases the desired adapter product while generating a ligateable end of the released duplex adapter. Further steps include nick repair (ligation) and separation of undesired products from the desired adapter product having a duplex SMI.

FIG. 12 depicts an embodiment of a method of adapter synthesis utilizing a reverse direction sequence extension scheme (i.e., wherein the template strand is enzymatically extended). In this embodiment, the template strand includes an SMI sequence and a hairpin loop structure that is proximal to the 3' end. In FIG. 12, the hairpin loop structure includes a self-complementary stem portion that includes one or more modified or non-standard bases, and a single stranded nucleotide linker portion which incorporates a capture label. The template strand self-anneals at a region of at least partial complementarity within the 3' region of the strand. Accordingly, following an annealing step, the template strand includes, in a 5' to 3' direction, a single stranded 5' region that includes a single stranded identifier sequence (e.g., a SMI sequence) and the 3' hairpin loop structure comprising a single-stranded nucleotide loop having the capture label and a 3' double-stranded stem portion.

Following annealing, a functionalized surface may be introduced. Alternatively, the functionalized surface may be introduced following additional annealing steps, an extension step or following the cutting step (e.g., consistent with solid-phase, solution-phase and hybrid approaches). Association with the functionalized surface can be provided via extraction moieties that are capable of binding to the capture label (e.g. a streptavidin bead where the capture label is biotin) for immobilization and separation of molecules bearing the capture label. Any capture label and compatible extraction moiety as described herein, or known in the art, may be used. Any time after association with the functionalized surface and throughout the synthesis process, one or more wash or other purification steps may be performed as desired in order to remove contaminants, undesired reagents, intermediates or byproducts as described elsewhere herein.

In a next step, a second strand is annealed to the template strand at an at least partially complimentary region located within the 5' single-stranded portion of the template strand. As shown, the SMI sequence resides between the at least partially complementary region and the 3' hairpin loop structure. Following hybridization of the template strand and the second strand, the template strand can be enzymatically extended via a non-strand displacing DNA polymerase (e.g., T4 DNA polymerase, T7 DNA polymerase) extend the double-stranded DNA sequence in the gap between the 3'hydroxyl group of the template strand and the 5' terminal end of the second strand. In this manner, the identifier (SMI) sequence is made double-stranded.

The extended double-stranded pre-adapter complex is immobilized on the functionalized surface via the 5' capture label interaction with one or more extraction moieties bound to the surface. Once desired wash or other purification steps have been completed, a cleavage event may be triggered, for example, at the region of modified or non-standard nucleotides (shown in FIG. 12 as a region including ribose bases) in order to release the desired adapter product from the functionalized surface. In the illustrated example, RNAseH (e.g., RNAseH2) can be introduced to the reaction mixture to cut at the ribose bases and release the desired adapter product having an identifier sequence (e.g., SMI) in both strands and having a ligateable end (e.g., a "T" overhang). Collection of the adapter product may occur at any time following release, including before or after nick repair as described below.

In some embodiments, one or more nicks will be introduced in this process, for example, at the end of an extension step. Such nicks can be repaired through use of an appropriate ligase to complete formation of the double-stranded adapter product.

It should be noted that although two oligonucleotides are shown being annealed in this process, one skilled in the art will appreciate that a similar outcome could be achieved with three distinct oligos, whereby the template strand, which is shown self-annealing to form a hairpin could be comprised of two separate oligonucleotides where the template strand and the extension portion of the strand are not linked together and are simply annealed. One of these strands could be linked to the surface and the other annealed to it, followed by annealing the third strand shown that forms a portion of the Y-shaped adapter in this non-limiting example. This approach also could apply to other examples discussed herein.

Figure 13A:
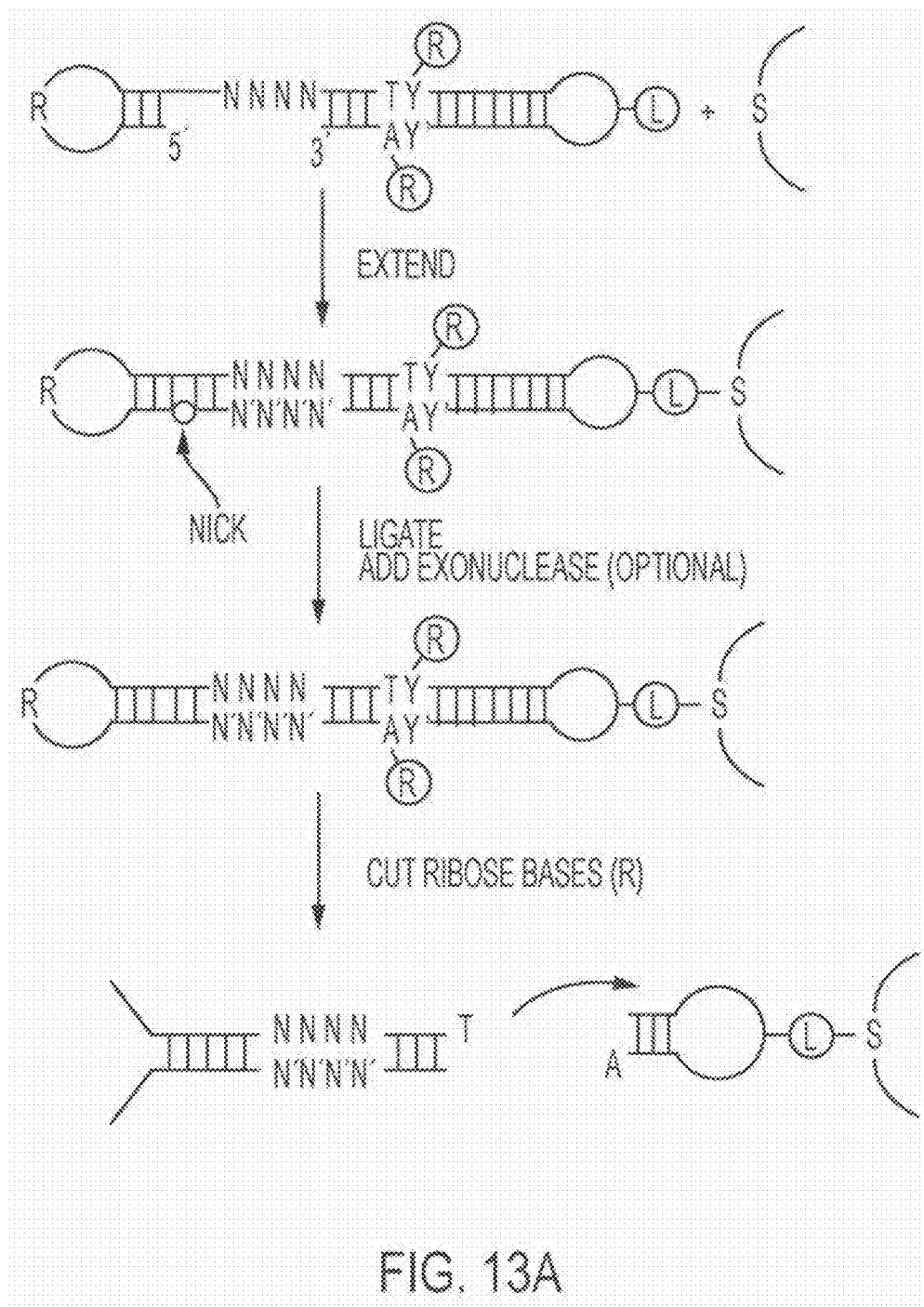
FIG. 13A illustrates a reverse adapter synthesis method using a single template strand having self-complementary regions at a 5' region and at a 3' region that are suitable to form hairpin loop structures. A polymerase is used to extend the complementary region between the 3' terminus and the 5' terminus of the template strand.
Figure 13B:
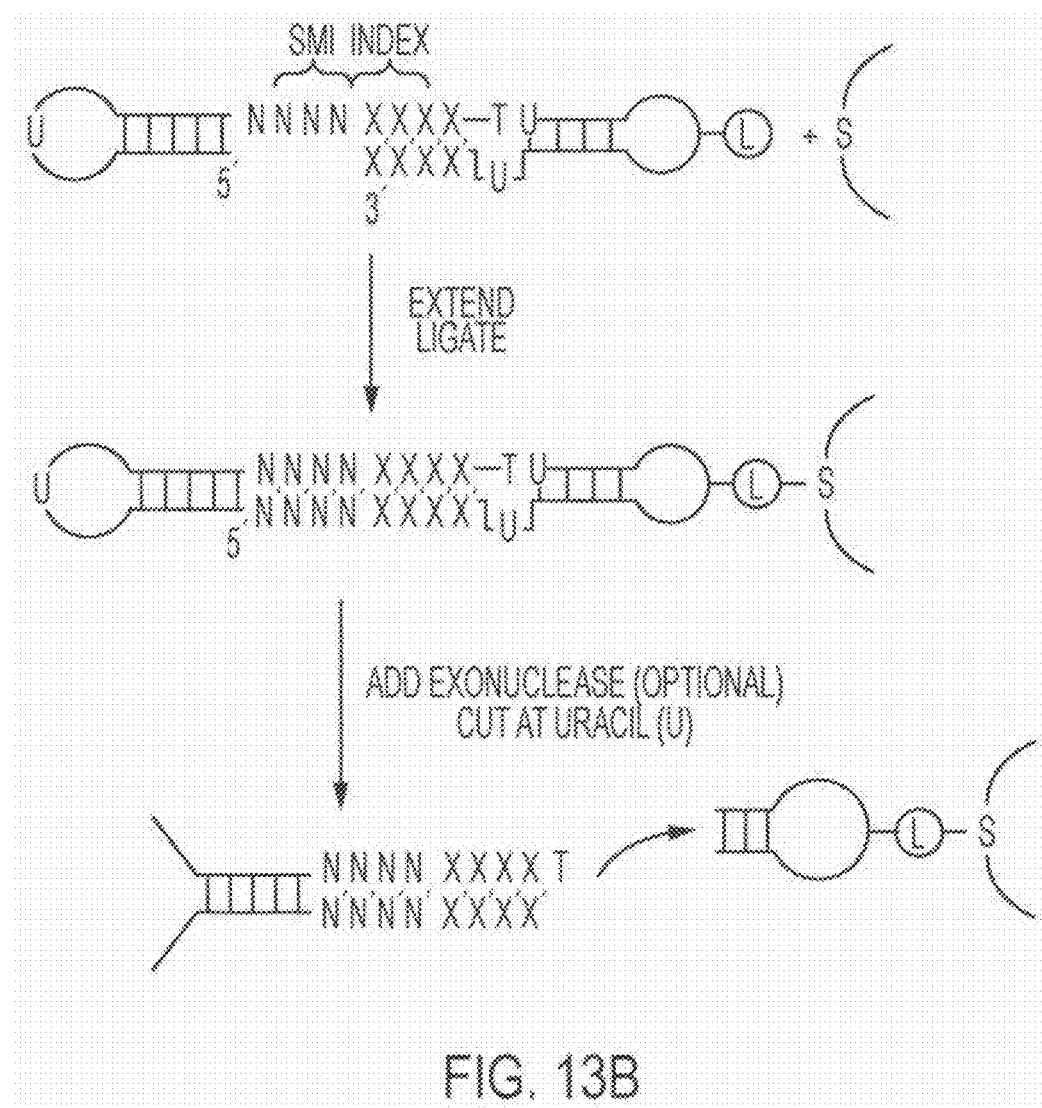
Figure 13C:
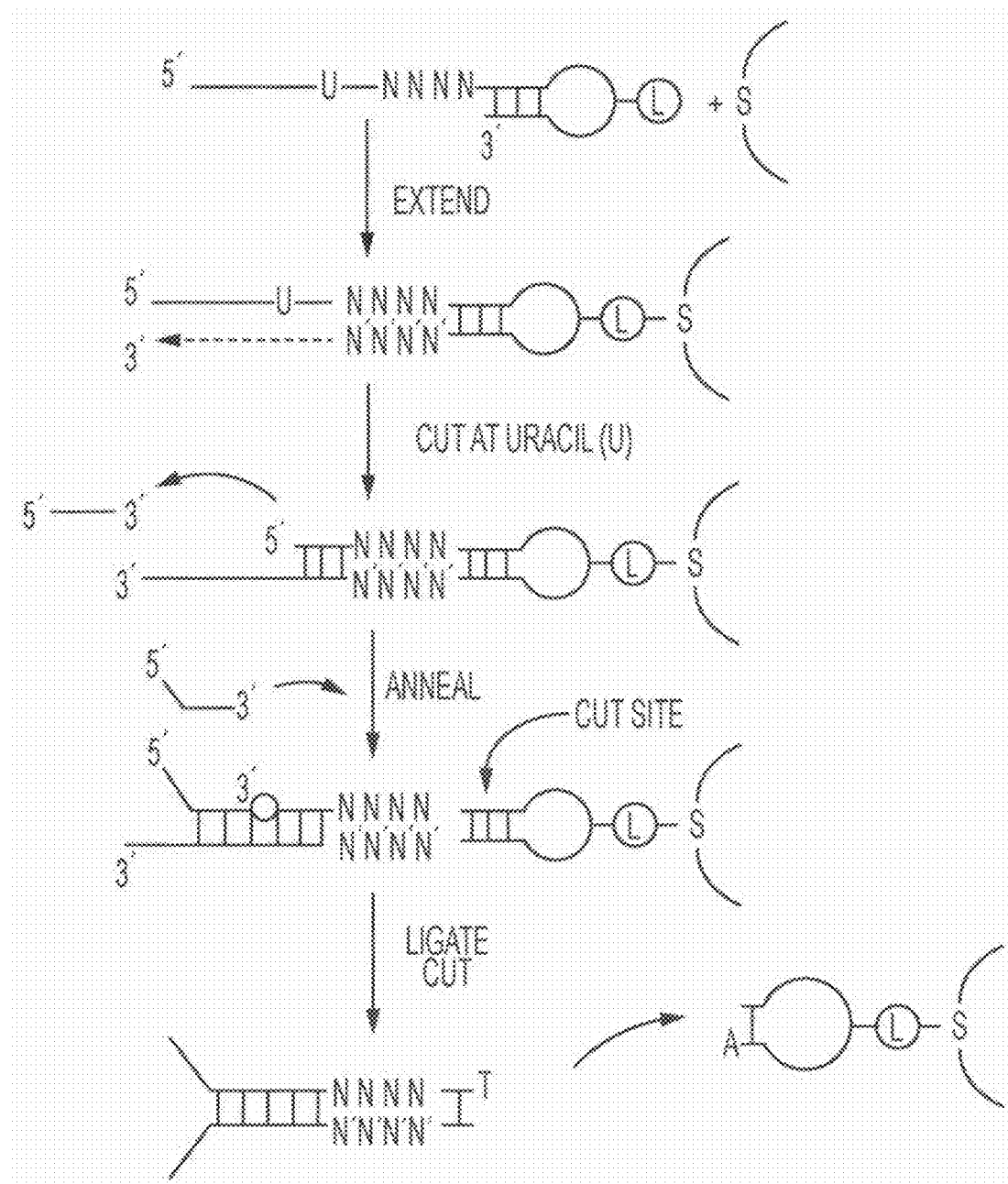
FIG. 13C illustrates an embodiment of reverse adapter synthesis in which a 5' asymmetric feature is generated following enzymatic extension to form a double-stranded SMI in the adapter complex.

FIGS. 13A-13C depict additional embodiments of methods using a reverse adapter synthesis scheme. Each of these additional embodiments incorporate concepts discussed above and it is specifically contemplated that those various concepts can apply to the embodiments below in any application-appropriate manner. For example, the nature, placement and/or orientation of capture label(s), hairpins, and modified or non-standard nucleotides may vary from the embodiments discussed below. One of skill in the art, upon exposure to this disclosure, will appreciate many permutations of the methods disclosed herein, each of which is contemplated as within the scope of the present disclosure.

FIG. 13A shows reverse adapter synthesis method using a single template strand having self-complementary sequences at both at a 5' region and at a 3' region. As illustrated, a first 5' sequence is complementary to a second 5' sequence, wherein the first 5' sequence is separated from the second 5' sequence with a non-complementary linker sequence which can include a first cleavable moiety, as shown in FIG. 13A. Following annealing of the first and second 5' sequences, the linker sequence forms a 5' hairpin. Likewise, a first 3' sequence is complementary to a second 3' sequence, wherein the first and second 3' sequences are separated by a non-complementary linker sequence. Following annealing of the first and second 3' sequences, the linker region forms a 3' hairpin. The non-complementary linker sequence in the 3' hairpin may include a capture label, and the complementary region of the 3' hairpin may further include a second cleavable moiety (e.g., one or more modified or non-standard nucleotides, such as a region of ribose bases as depicted in FIG. 13A).

Following annealing, a functionalized surface may be introduced. Alternatively, the functionalized surface may be introduced following additional steps including an extension step or following the cutting step (e.g., consistent with solid-phase, solution-phase and hybrid approaches discussed above). Association with the functionalized surface can be provided via extraction moieties that are capable of binding to the capture label (e.g. a streptavidin bead where the capture label is biotin) for immobilization and separation of molecules bearing the capture label. Any capture label and compatible extraction moiety as described herein, or known in the art, may be used. Any time after association with the functionalized surface and throughout the synthesis process, one or more wash or other purification steps may be performed as desired to remove contaminants, undesired reagents, intermediates or byproducts as described elsewhere herein.

A polymerase, such as a polymerase lacking strand-displacing activity (e.g., T4 or T7 DNA polymerase), is used to extend the complementary portions at the 5' and 3' regions thereby filling the gap therebetween. In particular, the polymerase can extend the template strand from the 3' hydroxyl group at the 3' end in a 5' to 3' direction to meet the 5' terminal end of the template strand. As such, an identifier sequence (e.g., an SMI containing degenerate or semi-degenerate nucleotides) is made double-stranded. Ligase is used to seal and repair nicks between the 3' and 5' ends (FIG. 13A). After extension and/or nick ligation, the circularized pre-adapter complexes may optionally be treated with exonuclease to destroy remaining nucleic acids in the reaction mixture. Because the desired pre-adapter complexes are bound via the capture label to the surface, the exonuclease can be washed/removed.

Next, a first cleaving event can be triggered to disrupt the first cleavable moiety in the 5' hairpin and create two tails to form a Y-shaped region. Either before, after, or at substantially the same time as the first cleavage event, a second cleavage event may be triggered at the second cleavable moiety (here a region comprising ribose bases within the complementary region of the 3' hairpin, as shown in FIG. 13A) to release the desired adapter product. In some embodiments, the second cleavage event yields a ligateable 3' end. In some embodiments, the first cleavable moiety and second cleavable moiety may be substantially the same, such that a single cleavage event may both release the adapter product from the capture label (and any associated cleaved sequence) as well as create a Y-shape (see the embodiment described in FIG. 13B below). Separation of the surface with bound byproduct and undesired intermediates from the desired adapter products in solution, provides a purified duplex adapter having an identifier (SMI) sequence in both strands.

FIG. 13B illustrates an embodiment similar to that in FIG. 13A, with two notable differences. First, the embodiment depicted in FIG. 13B includes a uracil as both the first cleavable moiety and second cleavable moiety. Second, an index sequence is integrated into the template strand 3' to the SMI. As illustrated, a uracil is used to force a mismatch near the 3' end of the intermediate adapter complex so that application of an appropriate enzyme, such as USER, cleaves to form a sticky end (e.g., T overhang) and also to form a Y-shaped adapter. Both FIG. 13A and FIG. 13B illustrate methods using incorporation of one or more modified or non-standard bases to form a ligateable end and/or to cleave the 5' hairpin feature to form a Y-shaped adapter complex.

FIG. 13C illustrates a variation of an embodiment of reverse adapter synthesis in which an asymmetric feature (e.g., a SDE) is generated. In this embodiment, a template strand having an incorporated modified base (e.g., uracil) followed by a single-stranded SMI sequence also has a complementary portion at a 3' region. As illustrated, a first 3' sequence is complementary to a second 3' sequence, wherein the first 3' sequence is separated from the second 3' sequence with a non-complementary linker sequence. Following annealing of the first and second 3' sequences, the linker sequence forms a 3' hairpin. In this embodiment, the 3' hairpin also includes a cut site and a capture label, which can be associated with a functionalized surface comprising one or more compatible extraction moieties as described elsewhere herein. A 5' to 3' polymerase is used to enzymatically extend the strand to form a double-stranded molecule with a 3' hairpin. Following extension, an enzyme (e.g., USER) may be used to form a nick at the modified base and the 5' portion of the template strand can be removed (e.g., via the application of elevated temperature). After removal of the 5' portion of the template strand, a partially complementary oligo (e.g., a second strand) can be annealed to a region of the single-stranded complex. The partially complementary oligo can have a non-complementary region such that following annealing and ligation of the nick, asymmetry is introduced in the adapter complex. A cleavage event may be triggered at the 3' end of the adapter complex (e.g., at the cut site) which can release the desired product from a functionalized surface (if using solid phase synthesis) while, in some embodiments, generating a ligateable end.

Figure 13D:
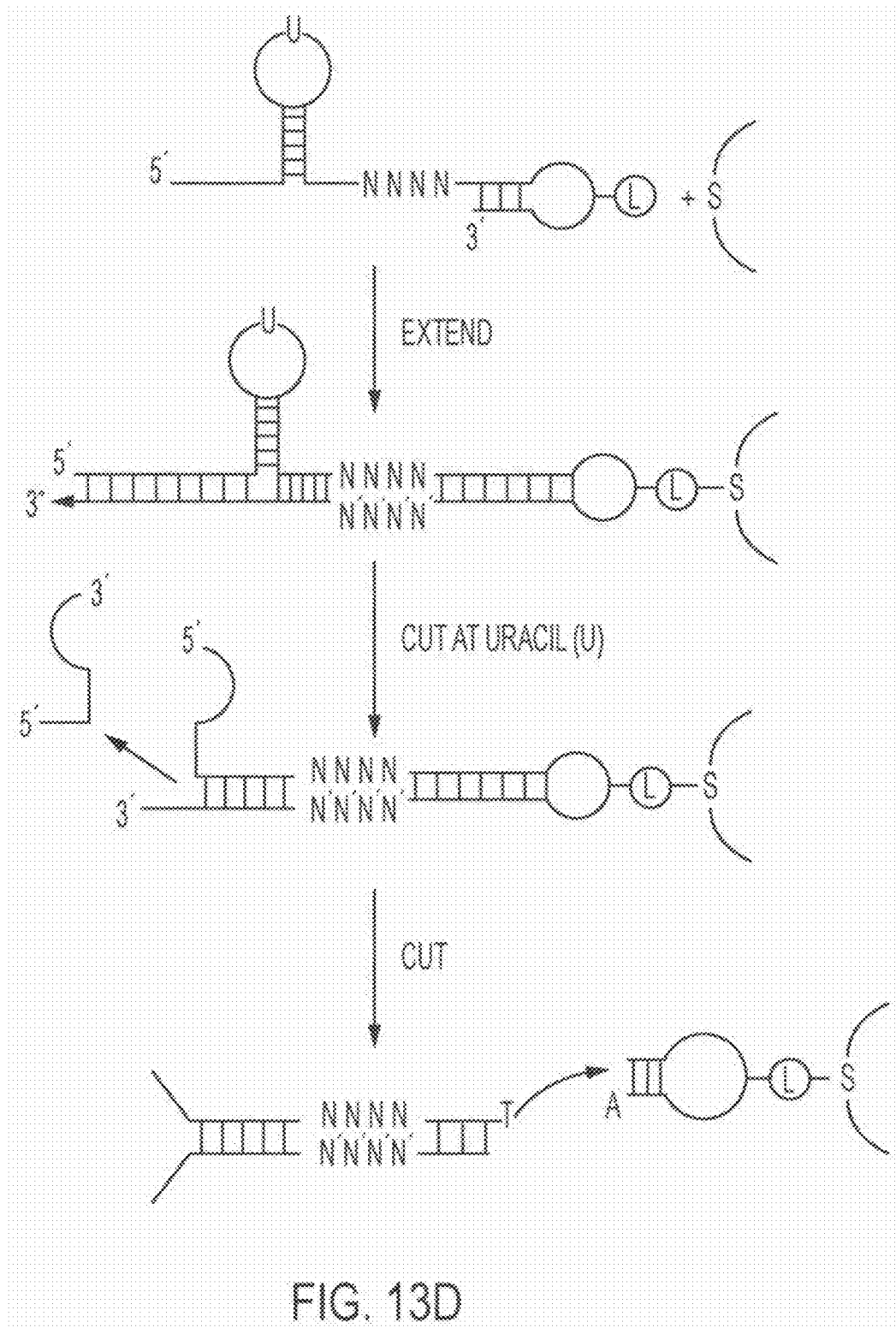
FIG. 13D illustrates a variation of an embodiment of reverse adapter synthesis using modified or non-standard base incorporation to form a Y-shaped adapter complex without using a ligation step.

FIG. 13D illustrates a variation of an embodiment of reverse adapter synthesis using modified or non-standard base incorporation to form a Y-shaped adapter complex without using a ligation step. As illustrated, FIG. 13D shows a reverse adapter synthesis method using a single template strand having complementary portion at a mid-region and at a 3' region. As illustrated, following a non-complementary 5' region, a first internal nucleotide sequence is complementary to a second internal nucleotide sequence, wherein the first internal nucleotide sequence is separated from the second internal nucleotide sequence with a non-complementary internal linker sequence. Following annealing of the first and second internal sequences, the linker sequence forms an internal hairpin. The internal linker sequence is provided with a modified/cleavable base (e.g., uracil).

Additionally, a first 3' sequence is complementary to a second 3' sequence, wherein the first and second 3' sequences are separated by a non-complementary linker sequence. Following annealing of the first and second 3' sequences, the linker region forms a 3' hairpin. In this embodiment, the 3' hairpin also includes a capture label which can be associated with a functionalized surface comprising one or more compatible extraction moieties as described elsewhere herein. A polymerase is used to extend the complementary portions at the 3' region. In this embodiment, the polymerase will cross a nucleotide gap formed by the internal hairpin structure formed in the mid-region of the template strand and continue to form double-stranded sequence complementary to the 5' region of the template strand. Following extension, cleavage at the modified base (e.g., uracil) located at/within the internal linker sequence and removal of the original 5' region of the template strand results in sequence asymmetry at the 5' end of the adapter. A digest/cleavage event at the 3' end of the adapter complex can release the desired product from a functionalized surface (if using solid phase synthesis) while, in some embodiments, generating a ligateable end. Following removal of the functionalized surface and associated intermediate and byproducts, a purified duplex adapter having an identifier (SMI) sequence in both strands is provided.

Examples

1. A method for preparing a duplex adapter, comprising:
annealing an elongation strand and a template strand at a complementary region, wherein the template strand comprises an identifier sequence and a capture label to form a first intermediate duplex adapter product;
extending the elongation strand to at least partially duplicate the identifier sequence to form a second intermediate duplex adapter product;
cutting the second intermediate duplex adapter product to form the duplex adapter and a cleaved by-product comprising the capture label; and
removing undesired products to form a duplex adapter.

2. The method of example 1, wherein the capture label is at a 5' end of the template strand such that non-annealed template strands, first and second intermediate duplex adapter products and by-products comprise the capture label.

3. The method of examples 1 or example 2, wherein the undesired products include non-annealed template strands, first and second intermediate duplex adapter products and by-products.

4. The method of any one of examples 1-3, further comprising providing a surface comprising an extraction moiety configured to bind the capture label.

5. The method of example 4, wherein the annealing, extending, and cutting steps occur in a liquid solution, and wherein the liquid solution is exposed to the surface following the cutting step.

6. The method of example 5, wherein prior to the annealing step the method comprises providing template strand and elongation strand and wherein the quantity of template strand exceeds the quantity of elongation strand.

7. The method of example 4, wherein the template strand is bound to the surface prior to the annealing step.

8. The method of example 4, wherein the template strand is bound to the surface via the capture label during the annealing and extending steps.

9. The method of example 4, wherein the capture label is bound to the extraction moiety on the surface following the annealing step and prior to the cutting step.

10. The method of examples 8 or 9, wherein the method further comprises providing an excess quantity of elongation strand compared to a quantity of template strand.

11. The method of example 4, wherein the removing step comprises separating the surface from a liquid solution, and wherein the non-annealed template strands, first and second intermediate duplex adapter products and by-products are bound to the surface via the capture label.

12. The method of any one of examples 1-11, further comprising collecting a purified duplex adapter product.

13. The method of any one of examples 1-12, wherein non-annealed template strands, first and second intermediate duplex adapter products and by-products are physically separated from the duplex adapters via the capture label.

14. The method of any one of examples 1-13, wherein the second intermediate duplex adapter product comprises a cut site comprising restriction endonuclease recognition sequence, and wherein the cutting step comprises providing a restriction endonuclease configured to cut the restriction endonuclease recognition sequence.

15. The method of example 14, wherein cutting the second intermediate duplex adapter product with the restriction endonuclease forms the duplex adapter having a ligateable 3' end.

16. The method of example 15, wherein the ligateable 3' end has a T-overhang.

17. The method of example 15, wherein the ligateable 3' end is a sticky end.

18. The method of any one of examples 1-17, wherein the capture label is a first capture label at a 5' end of the template strand, and wherein the template strand comprises a second capture label at a 3' end, and wherein the method further comprises:
providing a second surface comprising a second extraction moiety; and
cutting a 3' region of the template strand to release the duplex adapter from the second surface.

19. The method of example 18, wherein the first and second capture labels are different.

20. The method of example 18, wherein the first and second capture labels are the same.

21. The method of any one of examples 18-20, wherein the first and second surfaces are provided in the same step.

22. The method of any one of examples 18-21, wherein the first surface is provided and removed prior to providing the second surface.

23. The method any one of examples 18-20, wherein the 3' region of the template strand comprises a modified nucleotide or non-nucleotide molecule, and wherein cutting a 3' region of the template strand includes cutting at the modified nucleotide or non-nucleotide molecule.

24. The method of example 23, wherein the modified nucleotide is uracil, and wherein cutting the 3' region of the template strand comprises providing uracil-DNA glycosylase.

25. The method of any one of examples 18-24, wherein the 3' region of the template strand is non-complementary to the elongation strand.

26. The method of any one of examples 1-25, wherein extending the elongation strand to at least partially duplicate the identifier sequence comprises extending the elongation strand in a 5' to 3' direction.

27. The method of example 1, wherein the template strand and the elongation strand are linked by a linker domain.

28. The method of example 27, wherein the linker domain comprises nucleotides.

29. The method of examples 27 or 28, wherein the linker domain forms a loop comprising single-stranded nucleotides.

30. The method of any one of examples 27-29, wherein extending the elongation strand comprises extending the elongation strand from a 3' end of the elongation strand by enzymatic reaction.

31. The method of any one of examples 27-30, further comprising cutting the linker domain at any step following the annealing step to provide two single stranded arms at the 5' end of the adapter product.

32. The method of any one of examples 27-31, wherein the linker domain contains one or more modified nucleotides or non-nucleotide molecules.

33. The method of example 32, wherein the one or more modified nucleotides or non-nucleotide molecules is selected from 2-Aminopurine, 2,6-Diaminopurine (2-Amino-dA), 5-Bromo dU, deoxyUridine, Inverted dT, Inverted Dideoxy-T, Dideoxy-C, 5-Methyl dC, deoxylnosine, Super T®, Super G®, Locked Nucleic Acids, 5-Nitroindole, 2'-O-Methyl RNA Bases, Hydroxymethyl dC, Iso-dG, Iso-dC, Fluoro C, Fluoro U, Fluoro A, Fluoro G, 2-MethoxyEthoxy A, 2-MethoxyEthoxy MeC, 2-MethoxyEthoxy G, 2-MethoxyEthoxy T, 8-oxo-A. 5-hydroxymethyl-2'-deoxycytidine, iso-cytosine, Uracil, methylated nucleotide, RNA nucleotide, ribose nucleotide, 8-oxo-G, BrdU, Loto dU, Furan, fluorescent dye, azide nucleotide, abasic nucleotide, 5-nitroindole nucleotide, and digoxenin nucleotide.

34. The method of any one of examples 27-33, wherein the capture label is a first capture label at a 5' end of the template strand, and wherein the linker domain comprises a second capture label flanked by first and second cut sites.

35. The method of example 34, wherein the first and second cut sites comprise at least one of a modified nucleotide or non-nucleotide molecule, and a restriction endonuclease recognition site.

36. The method of examples 34 or 35, further comprising:
providing a first surface comprising a first extraction moiety configured to bind the first capture label;

providing a second surface comprising a second extraction moiety configured to bind the second capture label; and cutting at first and second cut sites within the linker domain to release the duplex adapter from the second surface.

37. The method of example 36, further comprising capturing molecules comprising the first capture label with the first surface, and capturing molecules comprising the second capture label with the second surface.

38. The method of examples 36 or 37, wherein the first and second capture labels are the same, and wherein the first and second extraction moieties are the same.

39. The method of examples 36 or 37, wherein the first and second capture labels are different.

40. The method of any of examples 36-37 or 39, wherein providing the second surface comprises providing the second surface following binding undesired products via the first surface.

41. The method of example 1, wherein the template strand comprises a hairpin loop structure having the capture label.

42. The method of example 41, further comprising providing a surface comprising an extraction moiety configured to bind the capture label, and capturing the template strand via binding the capture label by the extraction moiety.

43. The method of examples 41 or 42, wherein the template strand is bound to the surface prior the annealing step.

44. The method of any one of examples 41-43, wherein extending the elongation strand comprises extending the template strand from a 3' end by enzymatic reaction and ligating the extended template strand to a 5' end of the elongation strand.

45. The method of any one of examples 41-43, wherein the template strand comprises, in a 5' to 3' direction, a single-stranded portion having the identifier sequence, a double-stranded stem portion, and the hairpin loop structure, and wherein the stem portion comprises a region of complementary sequence between the 3' region of the template strand and a mid-region of the template strand, thereby forming the hairpin loop structure.

46. The method of example 45, wherein the stem portion comprises one or more modified nucleotides.

47. The method of example 46, wherein cutting the second intermediate duplex adapter product comprises cutting the stem portion at the one or more modified nucleotides or non-nucleotide molecules.

48. The method of example 47, wherein the one or more modified nucleotides or non-nucleotide molecules are selected from 2-Aminopurine, 2,6-Diaminopurine (2-Amino-dA), 5-Bromo dU, deoxyUridine, Inverted dT, Inverted Dideoxy-T, Dideoxy-C, 5-Methyl dC, deoxylnosine, Super T®, Super G®, Locked Nucleic Acids, 5-Nitroindole, 2'-O-Methyl RNA Bases, Hydroxymethyl dC, Iso-dG, Iso-dC, Fluoro C, Fluoro U, Fluoro A, Fluoro G, 2-MethoxyEthoxy A, 2-MethoxyEthoxy MeC, 2-MethoxyEthoxy G, 2-MethoxyEthoxy T, 8-oxo-A, 5-hydroxymethyl-2'-deoxycytidine, iso-cytosine, Uracil, methylated nucleotide, RNA nucleotide, ribose nucleotide, 8-oxo-G, BrdU, Loto dU, Furan, fluorescent dye, azide nucleotide, abasic nucleotide, 5-nitroindole nucleotide, and digoxenin nucleotide.

49. The method of examples 47 or 48, wherein cutting the stem portion comprises forming a duplex adapter having a 3' ligateable end.

50. The method of any one of examples 47-49, wherein cutting the stem portion releases the duplex adapter from the hairpin loop structure, and wherein removing the undesired products comprise separating the surface from the released duplex adapter.

51. The method of any one of examples 41-50, wherein the hairpin loop structure is a first hairpin loop structure, and wherein the template strand further comprises 52. A method for preparing a duplex adapter, comprising:
annealing an elongation strand and a template strand at a complementary region, wherein the template strand comprises an identifier sequence, a first capture label, a first cut site, a second capture label, and a second cut site to form a first intermediate duplex adapter product, wherein the first capture label is attached to the template strand via the first cut site;

extending the elongation strand to at least partially duplicate the identifier sequence to form a second intermediate duplex adapter product;

cutting the second intermediate duplex adapter product at the second cut site to form the duplex adapter and a cleaved by-product comprising the second capture label; and removing undesired products;

cutting the first cut site to release the duplex adapter;

removing additional undesired products.

53. The method of example 52, further comprising removing undesired products after the second cutting step, wherein undesired products comprise products having the first capture label.

54. The method of example 52 or 53, further comprising providing at least one extraction moiety configured to bind the first capture label, and capturing undesired products that include the first capture label.

55. The method of 54, wherein the extraction moiety is bound to a surface.

56. The method of example 54 or 55, wherein the extraction moiety is provided prior to the second cutting step.

57. The method of any one of examples 52-55, further comprising providing at least one extraction moiety configured to bind the second capture label, and capturing undesired products that include the second capture label.

58. The method of example 57, wherein the extraction moiety configured to bind the second capture label is bound to a surface.

59. The method of example 57 or 58, wherein the extraction moiety is provided prior to the first cutting step.

60. The method of any one of examples 52-59, wherein undesired products comprise one or more of excess template strand, excess elongation strand, non-extended or incompletely extended pre-adapter complexes, and cleavage fragment byproducts.

61. The method of any one of examples 52-60, wherein the template strand comprises an index sequence.

62. A method for preparing a set of duplex sequencing adapters having a double-stranded identifier sequence, comprising:

providing oligonucleotide synthesis solid supports comprising a plurality of template strands bound thereto, wherein the template strands comprise a nucleotide sequence extending from the oligonucleotide synthesis solid support to a 5' terminal end, and wherein a portion of the nucleotide sequence includes an identifier sequence that distinguishes each template strand from the other template strands;

annealing an elongation strand to each template strand at a complementary region to form a plurality of preliminary sequencing adapters;

extending each elongation strand in a 5' to 3' direction such that the identifier sequence is present on each strand of each preliminary sequencing adapter; and releasing the preliminary sequencing adapters from the oligonucleotide synthesis solid supports to provide a set of duplex sequencing adapters having a double-stranded identifier sequence.

63. The method of example 62, wherein each preliminary sequencing adapter comprises two single-stranded arms proximal to the oligonucleotide synthesis solid support.

64. The method of examples 62 or 63, further comprising enzymatically cutting a 3' end of the duplex sequencing adapters to form a 3' ligateable end.

65. The method of examples 62 or 63, further comprising enzymatically cutting a 3' end of the preliminary sequencing adapters to form a 3' ligateable end prior to the releasing step.

66. The method of examples 62-65, wherein the template strands are covalently bound to the oligonucleotide synthesis solid supports at a 3' end.

67. The method of examples 62-66, further comprising synthesizing the plurality of template strands on the oligonucleotide synthesis solid supports.

68. The method of any one of examples 62-67, wherein the oligonucleotide synthesis solid supports are controlled pore glass (CPG) beads or macroporous polystyrene (MPPS) beads.

69. A method for making a duplex adapter, comprising:
providing a template strand having an identifier sequence, a first hairpin loop structure at a 5' region and a second hairpin loop structure at a 3' region, wherein—
the first hairpin loop structure comprises a first single-stranded nucleotide loop having a first cut site and a 5' double-stranded stem portion,
the second hairpin loop structure comprises a second single-stranded nucleotide loop having a capture label and a 3' double-stranded stem portion having a second cut site, and
the template strand further comprises an identifier sequence in a mid-region between the 5' double-stranded stem portion and the 3' double-stranded stem portion;
enzymatically extending the template strand from a 3' terminal end to meet the 5' terminal end such that the identifier sequence is double-stranded; and
cutting the first and second cut sites to provide a duplex adapter having a single stranded portion at a 5' end of the duplex adapter, and having a ligation domain at a 3' end of the duplex adapter.

70. The method of example 69, further comprising separating the duplex adapter from undesired products.

71. The method of example 70, wherein undesired products comprise molecules having the second hairpin loop structure prior to the cutting step and after the cutting step.

72. The method of any one of examples 69-71, wherein the ligation domain comprises a T overhang, an A-overhang, a CG-overhang, a blunt end, a recombination sequence, a restriction digest overhang, or another ligateable region.

73. The method of any one of examples 69-72, wherein the first cut site is a nucleotide recognition site or modified nucleotide recognizable by an enzyme.

74. The method of example 73, wherein the first cut site comprises a uracil, and wherein the enzyme comprises a uracil-DNA glycosylase.

75. The method of example 73, wherein the second cut site comprises ribose nucleotides, and wherein the enzyme comprises an RNAse H enzyme.

76. The method of any one of examples 69-75, after the extending step, the method further comprises applying an exonuclease.

77. The method of any one of example 69-76, wherein the stem portions comprise self-complementary domains separated by a linker sequence, and wherein self-complementary domains anneal to form the stem portions and the linker sequence forms the single-stranded nucleotide loops.

78. A method for making a duplex adapter, comprising:
providing a template strand comprising, in a 5' to 3' direction, a single-stranded portion having a modified nucleotide or non-nucleotide molecule and an identifier sequence, a double-stranded stem portion having a cut site, and a single-stranded nucleotide loop having a capture label, wherein the stem portion comprises a region of complementary sequence between the 3' region of the template strand and a mid-region of the template strand, thereby forming the single-stranded nucleotide loop;
immobilizing the template strand via the capture label;
extending the single-stranded portion having the identifier sequence by from a 3' terminal end;
cleaving the template strand at the modified nucleotide; and
removing a 5' region of the template strand to generate a 3' single-stranded region of the template strand;
providing a second strand having a sequence at least partially complementary to the 3' single-stranded region of the template strand;
annealing the second strand to the 3' single-stranded region of the template strand to generate a pre-adapter complex; and
cutting the cut site to provide a duplex adapter having a double-stranded identifier sequence.

79. The method of example 78, further comprising separating the duplex adapter from a remaining immobilized sequence bearing the capture label to provide a purified duplex adapter.

80. The method of examples 78 or 79, further comprising repairing a single-stranded nick positioned between a 3' end of the second strand and the 5' end of the template strand.

81. The method of example 80, wherein repairing the single-stranded nick includes treating the immobilized pre-adapter complex with ligase.

82. The method of any one of examples 78-81, wherein the second strand and the template strand include regions of non-complementarity to provide a strand-defining element (SDE).

83. The method of example 82, wherein the SDE is two single-stranded arms at the 5' end of the pre-adapter complex.

84. The method of example 82, wherein the SDE is a bubble formed by a region of non-complementarity flanked by regions of complementarity between the second strand and the 3' single-stranded region of the template strand.

85. The method of any one of examples 78-84, wherein cutting the cut site provides a ligateable 3' end of the duplex adapter.

86. The method of example 85, wherein the ligateable 3' end comprises one of a T-overhang, an A-overhang, a blunt end, or a pre-determined sticky end.

87. The method of examples 85 or 86, wherein the cut site is a restriction endonuclease recognition sequence provided in the stem portion, and wherein cutting the cut site comprises providing a restriction endonuclease enzyme configured to recognize the restriction endonuclease recognition sequence.

88. The method of any one of examples 78-87, wherein immobilizing the template strand via the capture label comprises providing a functionalized surface configured to bind the capture label.

89. The method of any one of examples 78-88, wherein immobilizing the template strand via the capture label comprises providing an extraction moiety configured to bind the capture label.

90. The method of any one of examples 78-89, further comprising providing an excess of second strand compared to immobilized template strand.

91. The method of example 90, further comprising separating the excess second strand from the pre-adapter complex via selecting for molecules presenting the capture label.

92. A method for making a duplex adapter, comprising:
providing a template strand comprising, in a 5' to 3' direction, a single-stranded portion at a 5' region, a first hairpin loop structure, an identifier sequence, and a second hairpin loop structure, wherein—
the first hairpin loop structure comprises (a) a 5' double-stranded stem portion having a region of complementary sequence between the 5' region of the template strand and a mid-region of the template strand and forming a first single-stranded nucleotide loop between the region of complementarity sequence and (b) a single stranded nucleotide loop having a modified nucleotide or non-nucleotide molecule,
the second hairpin loop structure comprises (a) a 3' double-stranded stem portion having a region of complementarity sequence between the 3' region of the template strand a mid-region of the template strand and forming a second single-stranded nucleotide loop between the region of complementarity sequence, (b) a cut site, and (c) a single stranded nucleotide loop having a capture label, and
enzymatically extending the template strand from a 3' terminal end over the 5' double-stranded stem portion of the first hairpin loop structure such that the identifier sequence and the single-stranded portion are made double-stranded;
cutting the modified nucleotide or non-nucleotide molecule to create a single-stranded nick allowing for release of a single-stranded byproduct;
releasing the single-stranded byproduct; and
cutting the cut site to provide a duplex adapter having a single stranded portion at a 5' end of the duplex adapter, and having a ligation domain at a 3' end of the duplex adapter.

93. The method of example 92, further comprising separating the duplex adapter from undesired products.

94. The method of example 93, wherein undesired products comprise the first hairpin loop structure after cutting the modified nucleotide or non-nucleotide molecule.

95. The method of example 93 or 94, wherein undesired products comprise the capture label after cutting the cut site.

96. The method of any one of examples 92-95, wherein the modified nucleotide or non-nucleotide molecule is or comprises a uracil.

97. The method of example 92, wherein the duplex adapter further comprises a ligation domain.

98. The method of example 97, wherein the ligation domain is or comprises a T overhang, an A-overhang, a CG-overhang, a blunt end, a recombination sequence, a restriction digest overhang, or another ligateable region.

99. A method for making a purified duplex sequencing adapter having a physical unique molecular identifier (UMI) on each strand, comprising:
providing a preliminary sequencing adapter comprising a double-stranded hybridized region, two single-stranded arms, an overhang comprising the physical UMI at an end of the double-stranded hybridized region that is further away from the two single stranded arms, and a capture label at 5' end of the overhang;
extending one strand of the double-stranded hybridized region using the overhang as a template, thereby producing an extension product;
cutting the extension product in a double-stranded region 3' to the physical UMI at a cleavage site, thereby producing a duplex sequencing adapter and a byproduct comprising nucleotides 3' of the cleavage site and the capture label; and
separating the duplex sequencing adapter from undesired products to provide a purified duplex sequencing adapter having a physical UMI on each strand.

100. The method of example 99, wherein undesired products comprise products having the capture label following the cutting step.

101. The method of examples 99 or 100, wherein undesired products comprise the preliminary sequencing adapter, the extension product and the byproduct.

102. The method of any one of examples 99-101, further comprising capturing the undesired products with an extraction moiety configured to bind the capture label.

103. The method of any one of examples 99-102, wherein the preliminary sequencing adapter comprises an index sequence in each of the single stranded arms.

104. The method of any one of examples 99-102, wherein the preliminary sequencing adapter comprises an index sequence in the overhang.

105. The method of example 99, wherein the preliminary sequencing adapter comprises a read primer sequence on each strand.

106. The method of any one of examples 99-101, further comprising providing an extraction moiety configured to bind the capture label.

107. The method of example 106, wherein the extraction moiety is bound to a surface.

108. The method of example 107, wherein the extraction moiety is provided prior to the cutting step.

109. The method of any one of the above examples, wherein extending by enzymatic reaction comprises DNA polymerase activity.

110. The method of example 109, wherein the DNA polymerase is selected from Pol I, Pol II, Pol III, Pol IV, Pol V, Taq polymerase, polymerase alpha, polymerase beta, polymerase delta, polymerase lambda, polymerase sigma, polymerase epsilon, polymerase mu, polymerase zeta, polymerase nu, and polymerase theta.

111. The method of anyone of the above examples, further comprising ligating the duplex adapter to a double stranded nucleic acid molecule.

112. The method of example 111, wherein the ligating comprises ligase activity at a ligation domain.

113. The method of example 112, wherein the ligation domain is a nucleotide sequence from one or more degenerate or semi-degenerate nucleotides.

114. The method of any one of examples 111-113, wherein the ligation domain is a nucleotide sequence from one or more non-degenerate nucleotides.

115. The method of any one of examples 111-114, wherein the ligation domain contains one or more modified nucleotides.

116. The method of any one of examples 111-115, wherein the ligation domain comprises a T-overhang, an A-overhang, a CG-overhang, a blunt end, a recombination sequence, a restriction digest overhang, or another ligateable region.

117. The method of any one of examples 111-116, wherein at least one strand of the ligation domain is phosphorylated.

118. The method of any one of examples 111-117, wherein the ligation domain comprises a restriction endonuclease cleavage sequence.

119. The method of example 118, wherein the restriction endonuclease cleavage sequence is cleaved by a restriction endonuclease to yield a blunt end, or overhang ligateable region.

120. The method of any one of examples 111-119, wherein the ligation domain is 3' to the identifier sequence.

121. The method of any one of examples 111-119, wherein the ligation domain is 5' to the identifier sequence.

122. The method of example 111, wherein ligating comprises activity of at leak one ligase.

123. The method of example 122, wherein the at least one ligase is selected from a DNA ligase and a RNA ligase.

124. The method of any one of examples 111-123, wherein the double stranded nucleic acid molecule is a double stranded DNA molecule or a double stranded RNA molecule.

125. The method of any one of examples 111-124, wherein the double stranded nucleic acid molecule comprises at least one modified nucleotide or non-nucleotide molecule.

126. The method of any one of the above examples, wherein the identifier sequence is or comprises a single molecule identifier (SMI) sequence.

127. The method of example 126, wherein a SMI sequence is an endogenous SMI sequence.

128. The method of example 127, wherein the endogenous SMI sequence is related to shear point.

129. The method of any one of examples 126-128, wherein the SMI sequence comprises at least one degenerate or semi-degenerate nucleic acid.

130. The method of any one of examples 126-129, wherein the SMI sequence is non-degenerate.

131. The method of any one of examples 126-130, wherein the SMI sequence is a nucleotide sequence of one or more degenerate or semi-degenerate nucleotides.

132. The method of any one of examples 126-130, wherein the SMI sequence is a nucleotide sequence of one or more non-degenerate nucleotides.

133. The method of any one of examples 126-129, wherein the SMI sequence of the template strand and the SMI of the elongation strand are complementary.

134. The method of any one of examples 126-133, wherein the SMI sequence of the template strand and the SMI of the elongation strand are at least partially non-complementary.

135. The method of example 134, wherein the SMI sequence of the template strand and the SMI of the elongation strand are non-complementary.

136. The method of any one of examples 126-135, wherein the SMI sequence comprises at least one modified nucleotide or non-nucleotide molecule.

137. The method of any one of examples 126-136, wherein the SMI sequence comprises a primer binding domain.

138. The method of any one of the above examples, wherein at least one of the modified nucleotides or non-nucleotide molecules is selected from 2-Aminopurine, 2,6-Diaminopurine (2-Amino-dA), 5-Bromo dU, deoxyUridine, Inverted dT, Inverted Dideoxy-T, Dideoxy-C, 5-Methyl dC, deoxyInosine, Super T®, Super G®, Locked Nucleic Acids, 5-Nitroindole, 2'-O-Methyl RNA Bases, Hydroxymethyl dC, Iso-dG, Iso-dC, Fluoro C, Fluoro U, Fluoro A, Fluoro G, 2-MethoxyEthoxy A, 2-MethoxyEthoxy MeC, 2-MethoxyEthoxy 2-MethoxyEthoxy T. 8-oxo-A, 8-oxoG, 5-hydroxymethyl-2'-deoxycytidine, 5'-methylisocytosine, tetrahydrofuran, iso-cytosine, iso-guanosine, uracil, methylated nucleotide, RNA nucleotide, ribose nucleotide, 8-oxo-G, Loto dU, Furan, fluorescent dye, azide nucleotide, abasic nucleotide, 5-nitroindole nucleotide, and digoxenin nucleotide.

139. The method of any one of the above examples, wherein a cut site is or comprises a restriction endonuclease recognition sequence.

140. The method of any one of the above examples, wherein a capture label is or comprises at least one of Acrydite, azide, azide (NHS ester), digoxigenin (NHS ester), I-Linker, Amino modifier C6, Amino modifier C12, Amino modifier C6 dT, Unilink amino modifier, hexynyl, 5-octadiynyl dU, biotin, biotin (azide), biotin dT, biotin TEG, dual biotin, PC biotin, desthiobiotin TEG, thiol modifier C3, dithiol, thiol modifier C6 S-S, succinyl groups.

141. The method of any one of the above examples, wherein an extraction moiety is or comprises at least one of amino silane, epoxy silane, isothiocyanate, aminophenyl silane, aminpropyl silane, mercapto silane, aldehyde, epoxide, phosphonate, streptavidin, avidin, a hapten recognizing an antibody, a particular nucleic acid sequence, magnetically attractable particles (Dynabeads), photolabile resins.

In some embodiments, methods described herein may differ from previously described methods, inter alia, in allowing the use of excess template strand and avoiding the issue of having free elongation strand in solution which cannot readily be separated from the desired adapter product. Additionally, some embodiments of methods described herein may provide improved adapter purity, manufacturing efficiency, reproducibility, cost, and flexibility of adapter design.

One of skill in the art will appreciate that any portions of this disclosure may be used in a wide variety of combinations. While the present disclosure describes several of these combinations, the exemplified embodiments are not intended to be limiting.

Equivalents and Scope

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Those skilled in the art will recognize, or be able to ascertain using no more than routine experimentation, many equivalents to the specific embodiments of the disclosed technology described herein. The scope of the present technology is not intended to be limited to the above Description, but rather is as set forth in the following claims:

The invention claimed is:

1. A method for preparing a duplex adapter, comprising:
   annealing an elongation strand and a template strand at a complementary region to form a first intermediate duplex adapter product, wherein the template strand comprises:
   an identifier sequence,
   a first capture label attached to the template strand via a first cut site template, and
   a second capture label attached to the template strand via a second cut site;
   extending the elongation strand to at least partially duplicate the identifier sequence to form a second intermediate duplex adapter product comprising a first cut site between the identifier sequence and the first capture label;
   cutting the second intermediate duplex adapter product at the first cut site to form a third intermediate duplex adapter product and a first cleaved by-product comprising the first capture label;
   removing undesired products comprising the first capture label; and
   cutting at the second cut site to form the duplex adapter and a second cleaved by-product comprising the second capture label.

2. The method of claim 1, wherein the first capture label is at a 5' end of the template strand such that non-annealed template strands, first and second intermediate duplex adapter products and the first cleaved by-products comprise the first capture label.

3. The method of claim 1, further comprising providing at least one extraction moiety configured to bind the second capture label, and capturing undesired products that include the second capture label.

4. The method of claim 1, wherein the undesired products comprising the first capture label comprise one or more of excess template strand, non-extended first intermediate duplex adapter products, incompletely extended products formed during the extending step, uncut second intermediate duplex adapter products, and the first cleaved byproduct.

5. The method of claim 1, further comprising providing a surface comprising an extraction moiety configured to bind the first or second capture label.

6. The method of claim 5, wherein the template strand is bound to the surface prior to the annealing step.

7. The method of claim 5, wherein the extraction moiety is configured to bind the first capture label, and wherein the template strand is bound to the surface via the first capture label during the annealing and extending steps.

8. The method of claim 5, wherein the extraction moiety is configured to bind the first capture label, and wherein the first capture label is bound to the surface following the annealing step and prior to the first cutting step.

9. The method of claim 5, wherein the extraction moiety is configured to bind the first capture label, wherein the removing step comprises separating the surface from a liquid solution comprising the third intermediate duplex adapter product, and wherein the undesired products are bound to the surface via the first capture label.

10. The method of claim 1, wherein the template strand and the elongation strand are linked by a linker domain.

11. The method of claim 10, wherein the first capture label is at the 5' end of the template strand, and wherein the linker domain comprises the second capture label flanked by two second cut sites.

12. The method of claim 1, wherein cutting the third intermediate duplex adapter product comprises cutting at one or more modified nucleotides or non-nucleotide molecules.

13. The method of claim 3, wherein the extraction moiety configured to bind the second capture label is provided before or following the second cutting step.

14. The method of claim 1, wherein the first capture label is different from the second capture label.

15. The method of claim 1, wherein following the second cutting step, the method further comprises removing undesired products comprising the second capture label.

* * * * *